United States Patent
Kitamura et al.

(10) Patent No.: US 11,414,474 B2
(45) Date of Patent: *Aug. 16, 2022

(54) LONG-ACTING ADRENOMEDULLIN DERIVATIVES

(71) Applicant: University of Miyazaki, Miyazaki (JP)

(72) Inventors: Kazuo Kitamura, Miyazaki (JP); Johji Kato, Miyazaki (JP); Keishi Kubo, Miyazaki (JP); Kenji Kuwasako, Miyazaki (JP); Shigeru Kubo, Ibaraki (JP); Kumiko Kumagaye, Ibaraki (JP)

(73) Assignee: University of Miyazaki, Miyazaki (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/127,202

(22) PCT Filed: Mar. 20, 2015

(86) PCT No.: PCT/JP2015/058416
§ 371 (c)(1),
(2) Date: Sep. 19, 2016

(87) PCT Pub. No.: WO2015/141819
PCT Pub. Date: Sep. 24, 2015

(65) Prior Publication Data
US 2018/0170991 A1  Jun. 21, 2018

(30) Foreign Application Priority Data
Mar. 20, 2014 (JP) .............................. JP2014-058225

(51) Int. Cl.
*C07K 14/575* (2006.01)
*A61K 38/22* (2006.01)
*A61K 47/54* (2017.01)
*A61K 47/60* (2017.01)
*A61P 9/00* (2006.01)
*A61P 29/00* (2006.01)
*A61K 38/00* (2006.01)

(52) U.S. Cl.
CPC .......... *C07K 14/575* (2013.01); *A61K 47/542* (2017.08); *A61K 47/60* (2017.08); *A61P 9/00* (2018.01); *A61P 29/00* (2018.01); *A61K 38/00* (2013.01); *A61K 38/22* (2013.01)

(58) Field of Classification Search
CPC ....... C07K 14/575; A61K 47/60; A61K 38/22
See application file for complete search history.

(56) References Cited

U.S. PATENT DOCUMENTS

| 5,639,855 | A | 6/1997 | Kitamura |
| 2009/0028790 | A1 | 1/2009 | Dupuis et al. |
| 2009/0252703 | A1 | 10/2009 | Gragg, Jr. et al. |
| 2013/0296260 | A1 | 11/2013 | Kitamura et al. |
| 2014/0155329 | A1* | 6/2014 | Hsu .................. A61P 9/02 514/15.6 |
| 2014/0287984 | A1 | 9/2014 | Flamme et al. |
| 2018/0170991 | A1 | 6/2018 | Kitamura et al. |

FOREIGN PATENT DOCUMENTS

| CN | 103458916 | 12/2013 | |
| JP | 2774769 | 7/1998 | |
| JP | 4830093 | 10/2006 | |
| JP | 6685046 | 4/2020 | |
| WO | 02/098446 | 12/2002 | |
| WO | 2005/028516 | 3/2005 | |
| WO | 2005/044846 | 5/2005 | |
| WO | 2008/051383 | 5/2008 | |
| WO | 2012/096411 | 7/2012 | |
| WO | 2012/138867 | 10/2012 | |
| WO | WO-2012138867 A2 * | 10/2012 | ............. A61K 38/22 |
| WO | 2013/064508 | 5/2013 | |

OTHER PUBLICATIONS

Innovagen (Adrenomedullin (1-52) human peptide) (Year: 2018).*
Wong (Analysis of disulfide bonds in protein structures, Journal of Thrombosis and Haemostasis 2010, 8: 2345) (Year: 2010).*
Innovagen (Adrenomedullin (1-52) human peptide, of record) (Year: 2018).*
Wong (Analysis of disulfide bonds in protein structures, Journal of Thrombosis and Haemostasis 2010, 8: 2345, of record) (Year: 2010).*
Roberts (Chemistry for peptide and protein PEGylation, Advanced Drug Delivery Reviews 2002, 54: 459-476) (Year: 2002).*
Banerjee et al., "Poly(ethylene glycol)-Prodrug Conjugates: Concept, Design, and Applications", Journal of Drug Delivery, 2012, 17 pages (Year: 2012).*
Greenwald et al. "Effective drug delivery by PEGylated drug conjugates", Advanced Drug Delivery Reviews, 2003, pp. 217-250 (Year: 2003).*
Mero et al. "Chapter 8: Covalent Conjugation of Poly(Ethylene Glycol) to Proteins and Peptides: Strategies and Methods", Bioconjugation Protocols: Strategies and Methods, Methods in Molecular Biology, vol. 751,2011, pp. 95-129 (Year: 2011).*

(Continued)

*Primary Examiner* — Lianko G Garyu
(74) *Attorney, Agent, or Firm* — Morgan, Lewis & Bockius LLP

(57) ABSTRACT

There is provided a novel adrenomedullin derivative capable of sustainably acting for a longer period than natural adrenomedullin. The invention relates to a compound represented by formula (I): A-$L_n$-B (I), wherein A is a modifying group selected from the group consisting of a palmitoyl group and a polyethylene glycol group, L is a divalent linking group, n is an integer of 0 or 1, and B is a peptide moiety derived from adrenomedullin or a modified form thereof with adrenomedullin activity, wherein the peptide moiety B is bound to the modifying group A or the linking group L via the N-terminal amino group of the peptide moiety B, or a salt thereof, or a hydrate thereof.

20 Claims, 8 Drawing Sheets

Specification includes a Sequence Listing.

(56) References Cited

OTHER PUBLICATIONS

Supplemental European Search Report based on co-pending European Patent Application No. 15765038.3, dated Oct. 23, 2017—4 Pages.

Champion, Hunter C., et al., "Catecholarnine Release Mediates Pressor Effects of Adrenomedullin-(15-22) in the Rat", Hypertension, Dec. 1996, vol. 28, No. 6, pp. 1041-1046.

Champion, Hunter C., et al., "Structure-activity Relationships of Adrenomedullin in the Circulation and Adrenal Gland", Regulatory Peptides, 1999, vol. 85, No. 1, pp. 1-8.

Eguchi, Satoru, et al., "Structure-Activity Relationship of Adrenomedullin, a Novel Vasodilatory Peptide, in Cultured Rat Vascular Smooth Muscle Cells", Endocrinology, 1994, vol. 135, No. 6, pp. 2454-2458.

Garcia, Mario A., et al., "Synthesis, Biological Evaluation, and Three-Dimensional Quantitative Structure-Activity Relationship Study of Small-Molecule Positive Modulators of Adrenomedullin", Journal of Medicinal Chemistry, 2005, vol. 48, No. 12, pp. 4068-4075.

Mitsuda, Yuuichi, et al., "Large-scale Production of Functional Human Adrenomedullin: Expression, Cleavage, Amidation, and Purification", Protein Expression and Purification, 2002, vol. 25, No. 3, pp. 448-455.

Roldos, Virginia, et al., Small-Molecule Negative Modulators of Adrenomedullin: Design, Synthesis, and 3D-QSAR Study, ChemMedChem, 2008, vol. 3, No. 9, pp. 1345-1355.

Watanabe, Takushi, X., et al., "Vasopressor Activities of N-Terminal Fragments of Adrenomedullin in Anesthetized Rat", Biochemical and Biophysical Research Communications, 1996, vol. 219, No. 1, pp. 59-63.

Kubo, Keishi, et al., "Biological Properties of Adrenomedullin Conjugated with Polyethylene Glycol", Peptides, May 27, 2014, vol. 57, pp. 118-121.

Kitamura, Kazuo, et al., Adrenomedullin: A Novel Hypotensive Peptide Isolated from Human Pheochromocytoma, Biochemical and Biophysical Research Communications. Apr. 30, 1993, vol. 192, No. 2, pp. 553-560.

Belloni, A.S., et al., "Structure-Activity Relationships of Adrenomedullin in the Adrenal Gland", Endocrine Research, 1998, vol. 24, Nos. 3 and 4, pp. 729-730.

International Search Report based on International Application No. PCT/JP2015/058416, dated Jun. 23, 2015.

* cited by examiner

*P<0.0001 (vs Control)
†P<0.0001 (vs 0.02)
‡P<0.0001 (vs 0.1)

SEQUENCE LISTING

```
<160> NUMBER OF SEQ ID NOS: 49

<210> SEQ ID NO 1
<211> LENGTH: 52
<212> TYPE: PRT
<213> ORGANISM: Homo sapiens

<400> SEQUENCE: 1

Tyr Arg Gln Ser Met Asn Asn Phe Gln Gly Leu Arg Ser Phe Gly Cys
1               5                   10                  15

Arg Phe Gly Thr Cys Thr Val Gln Lys Leu Ala His Gln Ile Tyr Gln
            20                  25                  30

Phe Thr Asp Lys Asp Lys Asp Asn Val Ala Pro Arg Ser Lys Ile Ser
        35                  40                  45
```

```
Pro Gln Gly Tyr
        50

<210> SEQ ID NO 2
<211> LENGTH: 1449
<212> TYPE: DNA
<213> ORGANISM: Homo sapiens
<220> FEATURE:
<221> NAME/KEY: CDS
<222> LOCATION: (157)..(711)

<400> SEQUENCE: 2
ctggatagaa cagctcaagc cttgccactt cgggcttctc actgcagctg ggcttggact      60
tcggagtttt gccattgcca gtgggacgtc tgagactttc tccttcaagt acttggcaga    120
tcactctctt agcagggtct gcgcttcgca gccggg atg aag ctg gtt tcc gtc      174
                                       Met Lys Leu Val Ser Val
                                         1               5 gcc ctg atg tac ctg ggt tcg ctc gcc ttc cta ggc gct gac acc gct      222
Ala Leu Met Tyr Leu Gly Ser Leu Ala Phe Leu Gly Ala Asp Thr Ala
             10                  15                  20 cgg ttg gat gtc gcg tcg gag ttt cga aag aag tgg aat aag tgg gct      270
Arg Leu Asp Val Ala Ser Glu Phe Arg Lys Lys Trp Asn Lys Trp Ala
         25                  30                  35 ctg agt cgt ggg aag agg gaa ctg cgg atg tcc agc agc tac ccc acc      318
Leu Ser Arg Gly Lys Arg Glu Leu Arg Met Ser Ser Ser Tyr Pro Thr
     40                  45                  50 ggg ctc gct gac gtg aag gcc ggg cct gcc cag acc ctt att cgg ccc      366
Gly Leu Ala Asp Val Lys Ala Gly Pro Ala Gln Thr Leu Ile Arg Pro
 55                  60                  65                  70 cag gac atg aag ggt gcc tct cga agc ccc gaa gac agc agt ccg gat      414
Gln Asp Met Lys Gly Ala Ser Arg Ser Pro Glu Asp Ser Ser Pro Asp
                 75                  80                  85 gcc gcc cgc atc cga gtc aag cgc tac cgc cag agc atg aac aac ttc      462
Ala Ala Arg Ile Arg Val Lys Arg Tyr Arg Gln Ser Met Asn Asn Phe
             90                  95                 100 cag ggc ctc cgg agc ttt ggc tgc cgc ttc ggg acg tgc acg gtg cag      510
Gln Gly Leu Arg Ser Phe Gly Cys Arg Phe Gly Thr Cys Thr Val Gln
        105                 110                 115 aag ctg gca cac cag atc tac cag ttc aca gat aag gac aag gac aac      558
Lys Leu Ala His Gln Ile Tyr Gln Phe Thr Asp Lys Asp Lys Asp Asn
    120                 125                 130 gtc gcc ccc agg agc aag atc agc ccc cag ggc tac ggc cgc cgg cgc      606
Val Ala Pro Arg Ser Lys Ile Ser Pro Gln Gly Tyr Gly Arg Arg Arg
135                 140                 145                 150 cgg cgc tcc ctg ccc gag gcc ggc ccg ggt cgg act ctg gtg tct tct      654
Arg Arg Ser Leu Pro Glu Ala Gly Pro Gly Arg Thr Leu Val Ser Ser
                155                 160                 165 aag cca caa gca cac ggg gct cca gcc ccc ccg agt gga agt gct ccc      702
Lys Pro Gln Ala His Gly Ala Pro Ala Pro Pro Ser Gly Ser Ala Pro
            170                 175                 180 cac ttt ctt taggatttag gcgcccatgg tacaaggaat agtcgcgcaa               751
His Phe Leu
        185 gcatcccgct ggtgcctccc gggacgaagg acttcccgag cggtgtgggg accgggctct    811 gacagccctg cggagaccct gagtccggga ggcaccgtcc ggcggcgagc tctggctttg    871 caagggcccc tccttctggg gcttcgcttc cctagccttg ctcaggtgca aagtgcccca    931 ggggcggggt gcagaagaat ccgagtgtt tgccaggctt aaggagagga gaaactgaga    991
```

-continued

```
aatgaatgct gagaccccg gagcagggt ctgagccaca gccgtgctcg cccacaaact    1051
gatttctcac ggcgtgtcac cccaccaggg cgcaagcctc actattactt gaactttcca    1111
aaacctaaag aggaaaagtg caatgcgtgt tgtacataca gaggtaacta tcaatattta    1171
agtttgttgc tgtcaagatt ttttttgtaa cttcaaatat agagatattt ttgtacgtta    1231
tatattgtat taagggcatt ttaaaagcaa ttatattgtc ctcccctatt ttaagacgtg    1291
aatgtctcag cgaggtgtaa agttgttcgc cgcgtggaat gtgagtgtgt ttgtgtgcat    1351
gaaagagaaa gactgattac ctcctgtgtg gaagaaggaa acaccgagtc tctgtataat    1411
ctatttacat aaaatgggtg atatgcgaac agcaaacc                           1449
```

<210> SEQ ID NO 3
<211> LENGTH: 185
<212> TYPE: PRT
<213> ORGANISM: Homo sapiens

<400> SEQUENCE: 3

```
Met Lys Leu Val Ser Val Ala Leu Met Tyr Leu Gly Ser Leu Ala Phe
 1               5                  10                  15

Leu Gly Ala Asp Thr Ala Arg Leu Asp Val Ala Ser Glu Phe Arg Lys
            20                  25                  30

Lys Trp Asn Lys Trp Ala Leu Ser Arg Gly Lys Arg Glu Leu Arg Met
        35                  40                  45

Ser Ser Ser Tyr Pro Thr Gly Leu Ala Asp Val Lys Ala Gly Pro Ala
    50                  55                  60

Gln Thr Leu Ile Arg Pro Gln Asp Met Lys Gly Ala Ser Arg Ser Pro
65                  70                  75                  80

Glu Asp Ser Ser Pro Asp Ala Ala Arg Ile Arg Val Lys Arg Tyr Arg
                85                  90                  95

Gln Ser Met Asn Asn Phe Gln Gly Leu Arg Ser Phe Gly Cys Arg Phe
            100                 105                 110

Gly Thr Cys Thr Val Gln Lys Leu Ala His Gln Ile Tyr Gln Phe Thr
        115                 120                 125

Asp Lys Asp Lys Asp Asn Val Ala Pro Arg Ser Lys Ile Ser Pro Gln
    130                 135                 140

Gly Tyr Gly Arg Arg Arg Arg Ser Leu Pro Glu Ala Gly Pro Gly
145                 150                 155                 160

Arg Thr Leu Val Ser Ser Lys Pro Gln Ala His Gly Ala Pro Ala Pro
                165                 170                 175

Pro Ser Gly Ser Ala Pro His Phe Leu
            180                 185
```

<210> SEQ ID NO 4
<211> LENGTH: 52
<212> TYPE: PRT
<213> ORGANISM: Sus scrofa

<400> SEQUENCE: 4

```
Tyr Arg Gln Ser Met Asn Asn Phe Gln Gly Leu Arg Ser Phe Gly Cys
 1               5                  10                  15

Arg Phe Gly Thr Cys Thr Val Gln Lys Leu Ala His Gln Ile Tyr Gln
            20                  25                  30

Phe Thr Asp Lys Asp Lys Asp Gly Val Ala Pro Arg Ser Lys Ile Ser
        35                  40                  45

Pro Gln Gly Tyr
    50
```

<210> SEQ ID NO 5
<211> LENGTH: 1493
<212> TYPE: DNA
<213> ORGANISM: Sus scrofa

<400> SEQUENCE: 5

```
gcggaacagc tcgagccttg ccacctctag tttcttacca cagcttggac gtcggggttt      60
tgccactgcc agagggacgt ctcagacttc atcttcccaa atcttggcag atcacccccct    120
tagcagggtc tgcacatctc agccgggatg aagctggttc ccgtagccct catgtacctg     180
ggctcgctcg ccttcctggg cgctgacaca gctcggctcg acgtggcggc agagttccga     240
aagaaatgga ataagtgggc tctaagtcgt ggaaaaagag aacttcggct gtccagcagc     300
taccccaccg ggatcgccga cttgaaggcc gggcctgccc agactgtcat tcggccccag     360
gatgtgaagg ctcctctcg cagcccccag gccagcattc cggatgcagc ccgcatccga      420
gtcaagcgct accgccagag tatgaacaac ttccagggcc tgcggagctt cggctgtcgc     480
tttgggacgt gcaccgtgca aagctggcg caccagatct accagttcac ggacaaagac      540
aaggacggcg tcgcccccg gagcaagatc agccccagg gctacggccg ccggcgccga       600
cgctctctgc ccgaagccag cctgggccgg actctgaggt cccaggagcc acaggcgcac     660
ggggcccgg cctccccggc gcatcaagtg ctcgccactc tctttaggat ttaggcgcct      720
actgtggcag cagcgaacag tcgcgcatgc atcatgccgg cgcttcctgg ggcggggggc     780
ttcccggagc cgagcccctc agcggctggg gcccgggcag agacagcatt gagagaccga     840
gagtccggga ggcacagacc agcggcgagc cctgcatttt caggaacccg tcctgcttgg     900
aggcagtgtt ctcttcggct taatccagcc cgggtccccg ggtgggggtg gagggtgcag     960
aggaatccaa aggagtgtca tctgccaggc tcacggagag gagaaactgc gaagtaaatg    1020
cttagacccc caggggcaag ggtctgagcc actgccgtgc cgcccacaaa ctgatttctg    1080
aaggggaata accccaacag ggcgcaagcc tcactattac ttgaactttc caaaacctag    1140
agaggaaaag tgcaatgtat gttgtatata aagaggtaac tatcaatatt taagtttgtt    1200
gctgtcaaga ttttttttg taacttcaaa tatagagata tttttgtacg ttatatattg     1260
tattaagggc attttaaaac aattgtattg ttccctccc ctctatttta atatgtgaat     1320
gtctcagcga ggtgtaacat tgtttgctgc gcgaaatgtg agagtgtgtg tgtgtgtgtg    1380
cgtgaaagag agtctggatg cctcttgggg aagaagaaaa caccatatct gtataatcta    1440
tttacataaa atgggtgata tgcgaagtag caaaccaata aactgtctca atg           1493
```

<210> SEQ ID NO 6
<211> LENGTH: 52
<212> TYPE: PRT
<213> ORGANISM: Canis familiaris

<400> SEQUENCE: 6

```
Tyr Arg Gln Ser Met Asn Asn Phe Gln Gly Pro Arg Ser Phe Gly Cys
  1               5                  10                  15

Arg Phe Gly Thr Cys Thr Val Gln Lys Leu Ala His Gln Ile Tyr Gln
             20                  25                  30

Phe Thr Asp Lys Asp Lys Asp Gly Val Ala Pro Arg Ser Lys Ile Ser
         35                  40                  45

Pro Gln Gly Tyr
     50
```

<210> SEQ ID NO 7
<211> LENGTH: 1432
<212> TYPE: DNA
<213> ORGANISM: Canis familiaris

<400> SEQUENCE: 7

| | | | | | |
|---|---|---|---|---|---|
| ggttttgcca | gcaccagagc | gacgtctcag | accttctcct | cccggatctt | ggcagatcac | 60 |
| cccctcagca | gggtctgcgc | atcgccgcca | gcatgaagct | ggttcccgtc | gccctcttat | 120 |
| acctgggctc | cctcgccttc | ttgggcgcgg | acaccgcacg | gctagacgtg | gcgtcagagt | 180 |
| tccgaaagaa | gtggaataaa | tgggctgtaa | gtcgtggaaa | gagggaactt | cgagtgtcca | 240 |
| gcagctatcc | caccgggctc | gctgaagtga | aggccgggcc | ggcccagact | cttattcgga | 300 |
| cccaggacgt | gaagggcgcc | tctcgcaacc | cccagaccag | cggtccggac | gccgcccgca | 360 |
| tccgagtcaa | acgctaccgc | cagagtatga | acaatttcca | gggcccgcgg | agcttcggct | 420 |
| gccgcttcgg | aacgtgcacg | gtgcagaaac | tggcgcacca | gatctaccag | ttcacagaca | 480 |
| aggacaagga | cggcgtcgcc | cccaggagca | agattagccc | tcagggctac | ggccgccggc | 540 |
| gccggcgctc | cctgcccgag | cccggccttc | gccggactct | gttgttcccg | gagccacggc | 600 |
| caggcggggc | tccggccccc | cgggcgcatc | aggtgctcgc | caacctcctt | aagatgtagg | 660 |
| cgcctgtggc | agcagcgaac | tggcgcgcgt | gtgcatcccg | ctggcttccc | cctgggcgga | 720 |
| gggcttcccc | gagccgagcc | cctctgccga | tggaagtcgg | gcagagaccg | ggattccggg | 780 |
| aggcaccgtc | ccgcggccag | ccctggcttt | gcgcgagccc | cttctcctcg | gaggcacgga | 840 |
| tccctctgtc | ccaagccggc | ccaggtgtcc | cgtgggggc | agaggaatgc | aagggaggcc | 900 |
| tgccaggctc | acggagagga | ttaactgaga | attaaatgag | aattaaatgc | ttgagaccct | 960 |
| cccccctccc | cccccaggga | caggggtctg | agtcactgcc | gtgcctgccc | acaaactgat | 1020 |
| ttctcacggg | gtgtcacccc | accggggcgc | aagcctcact | attacttgaa | ctttccaaaa | 1080 |
| cctagagagg | aaaagtgcaa | tgcgtgttgt | atatacagag | gtaactatca | atatttaagt | 1140 |
| tcgttgctgt | cagaagattt | tttttgtaac | ttcaaatata | gagatatttt | tgtacgttat | 1200 |
| atattgtatt | aagggcattt | aaaaaccatt | gcattgtccc | cctccccact | tattttaata | 1260 |
| cgtgaatgtc | tcagcgaggt | gtaacgttgt | ttttgctgca | gagtgtgtga | gtgtgcgtga | 1320 |
| gagacttatt | acctcttgtg | gaagaaggaa | caccgtgtct | ctgcattatc | tatttacata | 1380 |
| aaatgggtga | tatgcgaaaa | tagcaaatca | ataataaacg | gtctcgatgc | tg | 1432 |

<210> SEQ ID NO 8
<211> LENGTH: 52
<212> TYPE: PRT
<213> ORGANISM: Bos taurus

<400> SEQUENCE: 8

Tyr Arg Gln Ser Leu Asn Asn Phe Gln Gly Leu Arg Ser Phe Gly Cys
1               5                   10                  15

Arg Phe Gly Thr Cys Thr Val Gln Lys Leu Ala His Gln Ile Tyr His
            20                  25                  30

Phe Thr Asp Lys Asp Lys Asp Gly Ser Ala Pro Arg Ser Lys Ile Ser
        35                  40                  45

Pro Gln Gly Tyr
    50

<210> SEQ ID NO 9
<211> LENGTH: 1439

<212> TYPE: DNA
<213> ORGANISM: Bos taurus

<400> SEQUENCE: 9

```
cgggaaacag ctcgaacctt ctcacttttg gcttctcact gcagcttcga cgtcggggtt      60
ttgccactgc cagaacgccg tctcagactt aatactccaa agaattttgg cagatcaccc     120
cctcagcagg gtctgcgcat cgccgccggg atgaagctgg ttcccgtcgc cctcctgtac     180
ctggggtcgc tcgccttcct aggcgtggac acggcacggc tcgacgtggc ggcagagttc     240
cgaaagaaat ggaataagtg ggctctaagt cgtggaaaaa gagaacttcg cgagtccagt     300
agctacccca ccgggctcgc cgacgtgaag gccgggcctg tccagactct tattcggccc     360
caggatgtaa agggcgcctc tcgaagccct caggccagca gtcctgacgc agcccgcatc     420
cgagtcaagc gctaccgcca gagtttgaac aacttccagg gcctgcggag cttcggttgt     480
cgcttcggga catgcacggt gcagaagttg gcgcatcaga tctaccattt cacggacaag     540
gacaaggacg gatccgcccc caggagcaag atcagccccc agggctacgg ccgtcggcgc     600
cgacgttcac tgcctgaggc cggcttgggt cggactctat tacagcctcc agagccaaag     660
ctgcgagggg ccccggactc ccgggtgcat caagtacttg ccaccctcag gatttaggcg     720
cctgggcagc agcgaacagt cgcgcacgca tctcgccggc acctcttcgg gcgggagggc     780
ttccgcgagc cgagccctc actcagccta tgggcccggg ctgagaacag ccctgagaga     840
ccgagagtcc aggaggcacc gtccggcagc cagcgagcac tggctttgca ggaacccgtc     900
ctcctcggag gggaggcagt gttctcttca ctctaattgg ggccaggtgc agtttctcct     960
ctccgtgagc ctggcagacg ctcacggaga ggagaaactg cgaaataaat gatgagaccc    1020
tcaggggcaa gggtctgagc cactgccgtg cccgcccaca aactgattcc tgatgggggt    1080
gtcaccccac cggggtgcaa gcctcactat tacttgaact ttccgaaacc tagagaggaa    1140
aagtgcaatg agtgttgtat atacagagat aattatcaat atttaaattt gttgttgtca    1200
agattttttt tgtaacttca aatatagaga tattttttgta cgttatatat tgtattaagg    1260
gcattttaaa gcaattgtat tgttcccctc ccctctattt taataagtga atgtctcagc    1320
gagatgcaac gttgtttgct gcgtggaatg tgagagtgtg tgcgtgaaag agatgagttg    1380
cctcttgtgg aagaagaaaa caccgtgtct gtataatcta tttacataaa gtgggccgg     1439
```

<210> SEQ ID NO 10
<211> LENGTH: 50
<212> TYPE: PRT
<213> ORGANISM: Rattus norvegicus

<400> SEQUENCE: 10

Tyr Arg Gln Ser Met Asn Gln Gly Ser Arg Ser Thr Gly Cys Arg Phe
1               5                   10                  15

Gly Thr Cys Thr Met Gln Lys Leu Ala His Gln Ile Tyr Gln Phe Thr
            20                  25                  30

Asp Lys Asp Lys Asp Gly Met Ala Pro Arg Asn Lys Ile Ser Pro Gln
        35                  40                  45

Gly Tyr
    50

<210> SEQ ID NO 11
<211> LENGTH: 1376
<212> TYPE: DNA
<213> ORGANISM: Rattus norvegicus

<400> SEQUENCE: 11

```
tccagcctttt accgctcctg gtttctcggc ttctcatcgc agtcagtctt ggactttgcg       60
ggttttgccg ctgtcagaag gacgtctcgg actttctgct tcaagtgctt gacaactcac      120
cctttcagca gggtatcgga gcatcgctac agaatgaagc tggttccat cgccctgatg       180
ttattgggtt cgctcgccgt tctcggcgcg acaccgcac ggctcgacac ttcctcgcag       240
ttccgaaaga agtggaataa gtgggcgcta agtcgtggga agagggaact acaagcgtcc      300
agcagctacc ctacggggct cgttgatgag aagacagtcc cgacccagac tcttgggctc      360
caggacaagc agagcacgtc tagcaccca caagccagca ctcagagcac agcccacatt      420
cgagtcaaac gctaccgcca gagcatgaac caggggtccc gcagcactgg atgccgcttt      480
gggacctgca caatgcagaa actggctcac cagatctacc agtttacaga caaagacaag      540
gacggcatgg cccccagaaa caagatcagc cctcaaggct atggccgccg cgccggcgt       600
tccctgccag aggtcctccg agcccggact gtggagtcct cccaggagca gacacactca      660
gctccagcct cccccggcgca ccaagacatc tccagagtct ctaggttata ggtgcgggtg      720
gcagcattga acagtcgggc gagtatccca ttggcgcctg cggaatcaga gagcttcgca      780
ccctgagcgg actgagacaa tcttgcagag atctgcctgg ctgccccctag ggaggcaga      840
ggaacccaag atcaagccag gctcacgtca gaaaccgaga attacaggct gatactctct      900
ccgggcaggt gtctgagcca ctgccttgcc cgctcataaa ctggttttct cacggggcat      960
acggctcatt acttacttga actttccaaa acctagcgag gaaaagtgca atgcttgtta     1020
tacagccaaa ggtaactatc atatttaagt ttgttgatgt caagaggttt tttttttgt      1080
aacttcaaat atatagaaat atttttgtac gttatatatt gtattaaggg catttttaaag    1140
cgattatatt gtcaccttcc cctatttaa gaagtgaatg tctcagcaag gtgtaaggtt      1200
gtttggttcc gtgtgtgtgt gtgtgtgt gtgtgtgt gtgtgtgt gtgtgtaagg           1260
tggagagcgc ctgattaccg cctgtggatg aagaaaaaac attgtgtctt ctataatcta     1320
tttacataaa atatgtgatc tgggaaaaag caaaccaata aactgtctca atgctg         1376
```

<210> SEQ ID NO 12
<211> LENGTH: 50
<212> TYPE: PRT
<213> ORGANISM: Mus musculus

<400> SEQUENCE: 12

```
Tyr Arg Gln Ser Met Asn Gln Gly Ser Arg Ser Asn Gly Cys Arg Phe
1               5                   10                  15

Gly Thr Cys Thr Phe Gln Lys Leu Ala His Gln Ile Tyr Gln Leu Thr
            20                  25                  30

Asp Lys Asp Lys Asp Gly Met Ala Pro Arg Asn Lys Ile Ser Pro Gln
        35                  40                  45

Gly Tyr
    50
```

<210> SEQ ID NO 13
<211> LENGTH: 1381
<212> TYPE: DNA
<213> ORGANISM: Mus musculus

<400> SEQUENCE: 13

```
cttggtgaca ctagacagag caactccagc gttaccgctc ccgctcctgg tttctcggct       60
tctcatcgca gtcaatcttg gactttgggg ttttgctact gtcagaagga cttctttctg      120
```

```
cttcaagtgc ttgacaacgc acccctttat cagggtatca gagcatcgcc acagaatgaa      180
gctggtttcc atcaccctga tgttattggg ttcactcgct ttcctaggcg cggacactgc      240
agggccagat actccttcgc agttccgaaa gaagtggaat aagtgggcgc taagtcgtgg      300
gaagagggaa ctacaagcat ccagcagcta ccctacggga ctcgctgatg agacgacagt      360
tcctacccag actcttgatc cattcctgga cgagcagaac acaactggcc cctacaagc      420 cagcaatcag agcgaagccc acattcgtgt caaacgctac cgccagagca tgaaccaggg      480
ttcccgcagc aatggatgcc gcttcgggac ctgcacattt cagaaattgg cccaccagat      540
ctaccagcta acagacaaag acaaggacgg catggctccc agaaacaaga tcagccctca      600
aggctatggc cgccggcgcc ggcgttccct gctggaggtc ctccggtccc ggactgtgga      660
gtcctcccag gagcagacac acacagcccc aggcccctgg gcgcacatct ccagactctt      720
taggatatag gtgcgggtga cagcattgaa cagtcgggcg agtatcccgt tggcgcctgc      780
ggaatcagag aacttcgcac cggggcggac tgagacaatc ctgcagagat ctgcctggct      840
gcccctaggg gaggcagagg aacccaagac caagccaggc tcatgccaga aaccgagact      900
tacaggctga tactctccgg gcaggggtct gagccactgc cttgcccgct cataaactgg      960
tttctcacgg ggcataagcc tcattactac ttgaactttc caaaacctag cgaggaacgt     1020
gcaatgcttg ttgtccagcc aaaggtaact atagtattta agtttgttgc tgtcaaggtt     1080 ttttttttg taacttcaaa tatatagaga tattttgta cgttatatat tgtattaagg      1140
gcattttaaa gtgattatat tgtcaccttc ccctatttta agacgtgaat gtctcagcaa     1200
ggtgtaaggt tgtttggttc cgtgtgtgtg tgtgtgtgtg tgtgtgtgtg tgtgtgtgtg     1260
taaggtggag agcgcctgat tatcgcctgt ggatgaagaa aaacattgt gtttcctata      1320 atctatttac ataaaatatg tgatctggga aaaagcaaac caataaactg tctcaatgct     1380
g                                                                    1381
```

```
<210> SEQ ID NO 14
<211> LENGTH: 6
<212> TYPE: PRT
<213> ORGANISM: Artificial Sequence
<220> FEATURE:
<223> OTHER INFORMATION: Adrenomedullin peptide

<400> SEQUENCE: 14

Met Asn Asn Phe Gln Gly
1               5

<210> SEQ ID NO 15
<211> LENGTH: 7
<212> TYPE: PRT
<213> ORGANISM: Artificial Sequence
<220> FEATURE:
<223> OTHER INFORMATION: Adrenomedullin peptide

<400> SEQUENCE: 15

Ser Met Asn Asn Phe Gln Gly
1               5

<210> SEQ ID NO 16
<211> LENGTH: 8
<212> TYPE: PRT
<213> ORGANISM: Artificial Sequence
<220> FEATURE:
<223> OTHER INFORMATION: Adrenomedullin peptide
```

```
<400> SEQUENCE: 16

Gln Ser Met Asn Asn Phe Gln Gly
1               5

<210> SEQ ID NO 17
<211> LENGTH: 9
<212> TYPE: PRT
<213> ORGANISM: Artificial Sequence
<220> FEATURE:
<223> OTHER INFORMATION: Adrenomedullin peptide

<400> SEQUENCE: 17

Arg Gln Ser Met Asn Asn Phe Gln Gly
1               5

<210> SEQ ID NO 18
<211> LENGTH: 10
<212> TYPE: PRT
<213> ORGANISM: Artificial Sequence
<220> FEATURE:
<223> OTHER INFORMATION: Adrenomedullin peptide

<400> SEQUENCE: 18

Tyr Arg Gln Ser Met Asn Asn Phe Gln Gly
1               5                   10

<210> SEQ ID NO 19
<211> LENGTH: 4
<212> TYPE: PRT
<213> ORGANISM: Artificial Sequence
<220> FEATURE:
<223> OTHER INFORMATION: Adrenomedullin peptide

<400> SEQUENCE: 19

Arg Ser Phe Gly
1

<210> SEQ ID NO 20
<211> LENGTH: 5
<212> TYPE: PRT
<213> ORGANISM: Artificial Sequence
<220> FEATURE:
<223> OTHER INFORMATION: Adrenomedullin peptide

<400> SEQUENCE: 20

Leu Arg Ser Phe Gly
1               5

<210> SEQ ID NO 21
<211> LENGTH: 4
<212> TYPE: PRT
<213> ORGANISM: Artificial Sequence
<220> FEATURE:
<223> OTHER INFORMATION: Adrenomedullin peptide

<400> SEQUENCE: 21

Cys Arg Phe Gly
1

<210> SEQ ID NO 22
<211> LENGTH: 9
<212> TYPE: PRT
<213> ORGANISM: Artificial Sequence
<220> FEATURE:
<223> OTHER INFORMATION: Adrenomedullin peptide

<400> SEQUENCE: 22
```

```
Leu Arg Ser Phe Gly Cys Arg Phe Gly
1               5
```

<210> SEQ ID NO 23
<211> LENGTH: 4
<212> TYPE: PRT
<213> ORGANISM: Artificial Sequence
<220> FEATURE:
<223> OTHER INFORMATION: Adrenomedullin peptide

<400> SEQUENCE: 23

```
Gln Lys Leu Ala
1
```

<210> SEQ ID NO 24
<211> LENGTH: 5
<212> TYPE: PRT
<213> ORGANISM: Artificial Sequence
<220> FEATURE:
<223> OTHER INFORMATION: Adrenomedullin peptide

<400> SEQUENCE: 24

```
Val Gln Lys Leu Ala
1               5
```

<210> SEQ ID NO 25
<211> LENGTH: 6
<212> TYPE: PRT
<213> ORGANISM: Artificial Sequence
<220> FEATURE:
<223> OTHER INFORMATION: Adrenomedullin peptide

<400> SEQUENCE: 25

```
Thr Val Gln Lys Leu Ala
1               5
```

<210> SEQ ID NO 26
<211> LENGTH: 7
<212> TYPE: PRT
<213> ORGANISM: Artificial Sequence
<220> FEATURE:
<223> OTHER INFORMATION: Adrenomedullin peptide

<400> SEQUENCE: 26

```
Cys Thr Val Gln Lys Leu Ala
1               5
```

<210> SEQ ID NO 27
<211> LENGTH: 8
<212> TYPE: PRT
<213> ORGANISM: Artificial Sequence
<220> FEATURE:
<223> OTHER INFORMATION: Adrenomedullin peptide

<400> SEQUENCE: 27

```
Thr Cys Thr Val Gln Lys Leu Ala
1               5
```

<210> SEQ ID NO 28
<211> LENGTH: 4
<212> TYPE: PRT
<213> ORGANISM: Artificial Sequence
<220> FEATURE:
<223> OTHER INFORMATION: Adrenomedullin peptide

<400> SEQUENCE: 28

Gln Ile Tyr Gln
1

<210> SEQ ID NO 29
<211> LENGTH: 5
<212> TYPE: PRT
<213> ORGANISM: Artificial Sequence
<220> FEATURE:
<223> OTHER INFORMATION: Adrenomedullin peptide

<400> SEQUENCE: 29

His Gln Ile Tyr Gln
1               5

<210> SEQ ID NO 30
<211> LENGTH: 4
<212> TYPE: PRT
<213> ORGANISM: Artificial Sequence
<220> FEATURE:
<223> OTHER INFORMATION: Adrenomedullin peptide

<400> SEQUENCE: 30

Asn Val Ala Pro
1

<210> SEQ ID NO 31
<211> LENGTH: 5
<212> TYPE: PRT
<213> ORGANISM: Artificial Sequence
<220> FEATURE:
<223> OTHER INFORMATION: Adrenomedullin peptide

<400> SEQUENCE: 31

Asp Asn Val Ala Pro
1               5

<210> SEQ ID NO 32
<211> LENGTH: 6
<212> TYPE: PRT
<213> ORGANISM: Artificial Sequence
<220> FEATURE:
<223> OTHER INFORMATION: Adrenomedullin peptide

<400> SEQUENCE: 32

Lys Asp Asn Val Ala Pro
1               5

<210> SEQ ID NO 33
<211> LENGTH: 7
<212> TYPE: PRT
<213> ORGANISM: Artificial Sequence
<220> FEATURE:
<223> OTHER INFORMATION: Adrenomedullin peptide

<400> SEQUENCE: 33

Asp Lys Asp Asn Val Ala Pro
1               5

<210> SEQ ID NO 34
<211> LENGTH: 8
<212> TYPE: PRT
<213> ORGANISM: Artificial Sequence
<220> FEATURE:
<223> OTHER INFORMATION: Adrenomedullin peptide

<400> SEQUENCE: 34

Lys Asp Lys Asp Asn Val Ala Pro

```
1               5
```

<210> SEQ ID NO 35
<211> LENGTH: 9
<212> TYPE: PRT
<213> ORGANISM: Artificial Sequence
<220> FEATURE:
<223> OTHER INFORMATION: Adrenomedullin peptide

<400> SEQUENCE: 35

```
Asp Lys Asp Lys Asp Asn Val Ala Pro
1               5
```

<210> SEQ ID NO 36
<211> LENGTH: 10
<212> TYPE: PRT
<213> ORGANISM: Artificial Sequence
<220> FEATURE:
<223> OTHER INFORMATION: Adrenomedullin peptide

<400> SEQUENCE: 36

```
Thr Asp Lys Asp Lys Asp Asn Val Ala Pro
1               5                   10
```

<210> SEQ ID NO 37
<211> LENGTH: 11
<212> TYPE: PRT
<213> ORGANISM: Artificial Sequence
<220> FEATURE:
<223> OTHER INFORMATION: Adrenomedullin peptide

<400> SEQUENCE: 37

```
Phe Thr Asp Lys Asp Lys Asp Asn Val Ala Pro
1               5                   10
```

<210> SEQ ID NO 38
<211> LENGTH: 4
<212> TYPE: PRT
<213> ORGANISM: Artificial Sequence
<220> FEATURE:
<223> OTHER INFORMATION: Adrenomedullin peptide

<400> SEQUENCE: 38

```
Pro Gln Gly Tyr
1
```

<210> SEQ ID NO 39
<211> LENGTH: 5
<212> TYPE: PRT
<213> ORGANISM: Artificial Sequence
<220> FEATURE:
<223> OTHER INFORMATION: Adrenomedullin peptide

<400> SEQUENCE: 39

```
Ser Pro Gln Gly Tyr
1               5
```

<210> SEQ ID NO 40
<211> LENGTH: 6
<212> TYPE: PRT
<213> ORGANISM: Artificial Sequence
<220> FEATURE:
<223> OTHER INFORMATION: Adrenomedullin peptide

<400> SEQUENCE: 40

```
Ile Ser Pro Gln Gly Tyr
1               5
```

```
<210> SEQ ID NO 41
<211> LENGTH: 7
<212> TYPE: PRT
<213> ORGANISM: Artificial Sequence
<220> FEATURE:
<223> OTHER INFORMATION: Adrenomedullin peptide

<400> SEQUENCE: 41

Lys Ile Ser Pro Gln Gly Tyr
1               5

<210> SEQ ID NO 42
<211> LENGTH: 8
<212> TYPE: PRT
<213> ORGANISM: Artificial Sequence
<220> FEATURE:
<223> OTHER INFORMATION: Adrenomedullin peptide

<400> SEQUENCE: 42

Ser Lys Ile Ser Pro Gln Gly Tyr
1               5

<210> SEQ ID NO 43
<211> LENGTH: 9
<212> TYPE: PRT
<213> ORGANISM: Artificial Sequence
<220> FEATURE:
<223> OTHER INFORMATION: Adrenomedullin peptide

<400> SEQUENCE: 43

Arg Ser Lys Ile Ser Pro Gln Gly Tyr
1               5

<210> SEQ ID NO 44
<211> LENGTH: 20
<212> TYPE: PRT
<213> ORGANISM: Artificial Sequence
<220> FEATURE:
<223> OTHER INFORMATION: Adrenomedullin peptide

<400> SEQUENCE: 44

Phe Thr Asp Lys Asp Lys Asp Asn Val Ala Pro Arg Ser Lys Ile Ser
1               5                   10                  15

Pro Gln Gly Tyr
            20

<210> SEQ ID NO 45
<211> LENGTH: 25
<212> TYPE: PRT
<213> ORGANISM: Artificial Sequence
<220> FEATURE:
<223> OTHER INFORMATION: Adrenomedullin peptide

<400> SEQUENCE: 45

His Gln Ile Tyr Gln Phe Thr Asp Lys Asp Lys Asp Asn Val Ala Pro
1               5                   10                  15

Arg Ser Lys Ile Ser Pro Gln Gly Tyr
            20                  25

<210> SEQ ID NO 46
<211> LENGTH: 33
<212> TYPE: PRT
<213> ORGANISM: Artificial Sequence
<220> FEATURE:
<223> OTHER INFORMATION: Adrenomedullin peptide
```

```
<400> SEQUENCE: 46

Thr Cys Thr Val Gln Lys Leu Ala His Gln Ile Tyr Gln Phe Thr Asp
1               5                   10                  15

Lys Asp Lys Asp Asn Val Ala Pro Arg Ser Lys Ile Ser Pro Gln Gly
                20                  25                  30

Tyr

<210> SEQ ID NO 47
<211> LENGTH: 42
<212> TYPE: PRT
<213> ORGANISM: Artificial Sequence
<220> FEATURE:
<223> OTHER INFORMATION: Adrenomedullin peptide

<400> SEQUENCE: 47

Leu Arg Ser Phe Gly Cys Arg Phe Gly Thr Cys Thr Val Gln Lys Leu
1               5                   10                  15

Ala His Gln Ile Tyr Gln Phe Thr Asp Lys Asp Lys Asp Asn Val Ala
                20                  25                  30

Pro Arg Ser Lys Ile Ser Pro Gln Gly Tyr
            35                  40

<210> SEQ ID NO 48
<211> LENGTH: 4
<212> TYPE: PRT
<213> ORGANISM: Artificial Sequence
<220> FEATURE:
<223> OTHER INFORMATION: Adrenomedullin peptide

<400> SEQUENCE: 48

Asn Phe Gln Gly
1

<210> SEQ ID NO 49
<211> LENGTH: 5
<212> TYPE: PRT
<213> ORGANISM: Artificial Sequence
<220> FEATURE:
<223> OTHER INFORMATION: Adrenomedullin peptide

<400> SEQUENCE: 49

Asn Asn Phe Gln Gly
1               5
```

LONG-ACTING ADRENOMEDULLIN DERIVATIVES

RELATED APPLICATIONS

This application is a national stage application filed under 35 USC 371 of PCT/JP2015/058416, filed Mar. 20, 2015, which claims the benefit of Japanese Patent Application No. 2014-058225, filed Mar. 20, 2014, all of which are incorporated herein, in entirety, by reference.

Submission of Sequence Listing

The Sequence Listing associated with this application is filed in electronic format via EFS-Web and hereby incorporated by reference into the specification in its entirety. The name of the text file containing the Sequence Listing is SequenceListing.txt. The size of the text file is 25586 bytes, and the text file was created on Jan. 6, 2022.

TECHNICAL FIELD

The invention relates to long-acting adrenomedullin derivatives.

BACKGROUND ART

Adrenomedullin, hereinafter also described as "AM", is a bioactive peptide which was isolated and identified from pheochromocytoma in 1993 (Non Patent Literature 1). At the beginning of the discovery, AM was found to exert a strong vasodilatory hypotensive effect. For example, Patent Literature 1 describes a peptide having a blood pressure-lowering effect that comprises the amino acid sequence of human AM.

Subsequent studies revealed that AM exerts diverse pharmacological effects such as a cardiovascular protective effect, an anti-inflammatory effect, an angiogenic effect, and a tissue repair promoting effect. In an effort to apply the pharmacological effects of AM to treatment of disease, administration of AM to patients with different diseases has been attempted. AM is expected to be useful as a therapeutic agent for inflammatory bowel diseases, pulmonary hypertension, peripheral vascular diseases, or acute myocardial infarction, among others.

For example, Patent Literature 2 describes an agent for preventing or treating nonbacterial inflammatory bowel diseases, wherein the agent comprises, as an active ingredient, adrenomedullin or a derivative thereof that has an activity to suppress nonbacterial inflammation, or a salt thereof that has an activity to suppress nonbacterial inflammation.

Patent Literature 3 describes a method for preventing or treating an inflammatory bowel disease for which the use of a steroid formulation, an immunosuppressant, or a biological formulation is difficult or insufficiently effective in a patient in need of prevention or treatment of the inflammatory bowel disease, the method comprising administering an effective amount of adrenomedullin, a modified form thereof having an activity of suppressing inflammation, or a salt of the adrenomedullin or the modified form having an activity of suppressing inflammation, to the patient.

Structure-activity relationship studies of AM have advanced identification of essential sequences that can contribute bioactivity of AM (Non Patent Literatures 2 to 9).

CITATION LIST

Patent Literature

Patent Literature 1: JP Patent No. 2774769
Patent Literature 2: JP Patent No. 4830093
Patent Literature 3: WO 2012/096411

Non Patent Literature

Non Patent Literature 1: Kitamura K, Kangawa K, Kawamoto M, Ichiki Y, Nakamura S, Matsuo H, Eto T. Adrenomedullin: a novel hypotensive peptide isolated from human pheochromocytoma. Biochem Biophys Res Commun, 30 Apr. 1993, Volume 192, Issue 2, pp. 553-560.
Non Patent Literature 2: Belloni, A. S. et al., Structure-activity relationships of adrenomedullin in the adrenal gland. Endocr Res, 1998, Volume 24, Issue 3-4, p. 729-30.
Non Patent Literature 3: Champion, H. C. et al., Catecholamine release mediates pressor effects of adrenomedullin-(15-22) in the rat. Hypertension, 1996, Volume 28, Issue 6, p. 1041-6.
Non Patent Literature 4: Champion, H. C., G. G. Nussdorfer, and P. J. Kadowitz, Structure-activity relationships of adrenomedullin in the circulation and adrenal gland. Regul Pept, 1999, Volume 85, Issue 1, p. 1-8.
Non Patent Literature 5: Eguchi, S. et al., Structure-activity relationship of adrenomedullin, a novel vasodilatory peptide, in cultured rat vascular smooth muscle cells. Endocrinology, 1994, Volume 135, Issue 6, p. 2454-8.
Non Patent Literature 6: Garcia, M. A. et al., Synthesis, biological evaluation, and three-dimensional quantitative structure-activity relationship study of small-molecule positive modulators of adrenomedullin. J Med Chem, 2005, Volume 48, Issue 12, p. 4068-75.
Non Patent Literature 7: Mitsuda, Y. et al., Large-scale production of functional human adrenomedullin: expression, cleavage, amidation, and purification. Protein Expr Purif, 2002, Volume 25, Issue 3, p. 448-55.
Non Patent Literature 8: Roldos, V. et al., Small-molecule negative modulators of adrenomedullin: design, synthesis, and 3D-QSAR study. ChemMedChem, 2008, Volume 3, Issue 9, p. 1345-55.
Non Patent Literature 9: Watanabe, T. X. et al., Vasopressor activities of N-terminal fragments of adrenomedullin in anesthetized rat. Biochem Biophys Res Commun, 1996, Volume 219, Issue 1, p. 59-63.

SUMMARY OF INVENTION

Technical Problem

Adrenomedullin is a compound that has various pharmacological effects. A medicament comprising adrenomedullin as an active ingredient will be expected to be applied to the prevention or treatment of different diseases. However, adrenomedullin is a peptide. Peptides are generally known to have a short half-life due to a metabolism in a living body such as in blood. This may cause a very short duration of action of the medicament comprising adrenomedullin as an active ingredient in subjects e.g., human patients. Thus, there is room for further improvements for using adrenomedullin as a medicament.

The invention, therefore, is intended to provide a novel adrenomedullin derivative capable of sustainably acting for a longer period than a natural adrenomedullin.

Solution to Problem

The present inventors have found as a result of various investigations of means to solve the problems described above that chemical modification of the N-terminal amino group of natural adrenomedullin with a specific modifying group can prolong blood half-life of the modified adrenomedullin as compared to natural adrenomedullin while retaining bioactivity of natural adrenomedullin. The present inventors have achieved the invention based on the finding described above.

That is to say, a summary of the invention is as the following:

(1) A compound represented by formula (I):

A-L$_n$-B         (I)

wherein

A is a modifying group selected from the group consisting of a palmitoyl group and a polyethylene glycol group, L is a divalent linking group, n is an integer of 0 or 1, and B is a peptide moiety derived from adrenomedullin or a modified form thereof with adrenomedullin activity, wherein the peptide moiety B is bound to the modifying group A or the linking group L via the N-terminal amino group of the peptide moiety B or a salt thereof, or a hydrate thereof.

(2) The compound according to (1), wherein the adrenomedullin or the modified form thereof with adrenomedullin activity is a peptide selected from the group consisting of:

(i) a peptide consisting of an amino acid sequence of adrenomedullin, (ii) a peptide that consists of an amino acid sequence of adrenomedullin and has a disulfide bond formed by two cysteine residues in the amino acid sequence, (iii) a peptide wherein the disulfide bond in the peptide of (ii) is substituted with an ethylene group, and that has adrenomedullin activity, (iv) a peptide wherein 1 to 15 amino acids in any of the peptides of (i) to (iii) are deleted, substituted or added, and that has adrenomedullin activity, (v) a peptide wherein the C-terminus of any of the peptides of (i) to (iv) is amidated, and (vi) a peptide wherein a glycine residue is added to the C-terminus of any of the peptides of (i) to (iv).

(3) The compound according to (1) or (2), wherein the adrenomedullin or the modified form thereof is a peptide selected from the group consisting of:

(a) a peptide consisting of the amino acid sequence of SEQ ID NO: 1 or a peptide consisting of the amino acid sequence of SEQ ID NO: 1 and having a disulfide bond formed by the cysteine residues at positions 16 and 21;

(b) a peptide consisting of the amino acid sequence of SEQ ID NO: 4 or a peptide consisting of the amino acid sequence of SEQ ID NO: 4 and having a disulfide bond formed by the cysteine residues at positions 16 and 21;

(c) a peptide consisting of the amino acid sequence of SEQ ID NO: 6 or a peptide consisting of the amino acid sequence of SEQ ID NO: 6 and having a disulfide bond formed by the cysteine residues at positions 16 and 21;

(d) a peptide consisting of the amino acid sequence of SEQ ID NO: 8 or a peptide consisting of the amino acid sequence of SEQ ID NO: 8 and having a disulfide bond formed by the cysteine residues at positions 16 and 21;

(e) a peptide consisting of the amino acid sequence of SEQ ID NO: 10 or a peptide consisting of the amino acid sequence of SEQ ID NO: 10 and having a disulfide bond formed by the cysteine residues at positions 14 and 19;

(f) a peptide consisting of the amino acid sequence of SEQ ID NO: 12 or a peptide consisting of the amino acid sequence of SEQ ID NO: 12 and having a disulfide bond formed by the cysteine residues at positions 14 and 19;

(g) a peptide wherein the disulfide bond in any of the peptides of (a) to (0 is substituted with an ethylene group, and that has adrenomedullin activity;

(h) a peptide wherein 1 to 15 amino acids in any of the peptides of (a) to (g) are deleted, substituted or added, and that has adrenomedullin activity;

(i) a peptide wherein the C-terminus of any of the peptides of (a) to (h) is amidated; and (j) a peptide wherein a glycine residue is added to the C-terminus of any of the peptides of (a) to (h).

(4) A method for producing the compound according to any of (1) to (3), comprising a linking step of linking a precursor of the peptide moiety B derived from adrenomedullin or a modified form thereof, a precursor of the modifying group A selected from the group consisting of a palmitoyl group and a polyethylene glycol group, and a precursor of the divalent group L$_n$ to form the compound represented by formula (I).

(5) A medicament comprising the compound according to any of (1) to (3) or a pharmaceutically acceptable salt thereof, or a pharmaceutically acceptable hydrate thereof as an active ingredient.

(6) The medicament according to (5) for use in the prevention or treatment of a cardiovascular disease, an inflammatory disease, or a peripheral vascular disease.

(7) An agent for preventing or treating a cardiovascular disease, an inflammatory disease, or a peripheral vascular disease, wherein the agent comprises the compound according to any of (1) to (3) or a pharmaceutically acceptable salt thereof, or a pharmaceutically acceptable hydrate thereof as an active ingredient.

(8) A pharmaceutical composition comprising the compound according to any of (1) to (3) or a pharmaceutically acceptable salt thereof, or a pharmaceutically acceptable hydrate thereof and one or more pharmaceutically acceptable carriers.

(9) The pharmaceutical composition according to (8) for use in the prevention or treatment of a cardiovascular disease, an inflammatory disease, or a peripheral vascular disease.

(10) A method for preventing or treating a condition, disease, and/or disorder, comprising administering to a subject in need of prevention or treatment of the condition, disease, and/or disorder an effective amount of the compound according to any of (1) to (3) or a pharmaceutically acceptable salt thereof, or a pharmaceutically acceptable hydrate thereof.

(11) The method according to (10) wherein the condition, disease, and/or disorder is a cardiovascular disease, an inflammatory disease, or a peripheral vascular disease.

(12) The compound according to any of (1) to (3) or a pharmaceutically acceptable salt thereof, or a pharmaceutically acceptable hydrate thereof for use in the prevention or treatment of a condition, disease, and/or disorder.

(13) The compound according to (12) wherein the condition, disease, and/or disorder is a cardiovascular disease, an inflammatory disease, or a peripheral vascular disease.

(14) Use of the compound according to any of (1) to (3) or a pharmaceutically acceptable salt thereof, or a pharmaceutically acceptable hydrate thereof for the manufacture of a medicament for the prevention or treatment of a condition, disease, and/or disorder.

(15) The use according to (14) wherein the condition, disease, and/or disorder is a cardiovascular disease, an inflammatory disease, or a peripheral vascular disease.

Advantageous Effects of Invention

The invention can provide a novel adrenomedullin derivative capable of sustainably acting for a longer period than natural adrenomedullin.

The present specification includes contents described in the specification and/or drawings of Japanese patent application No. 2014-058225 to which the present application claims priority.

DESCRIPTION OF EMBODIMENTS

<1. Adrenomedullin Derivative>

Figure 1:
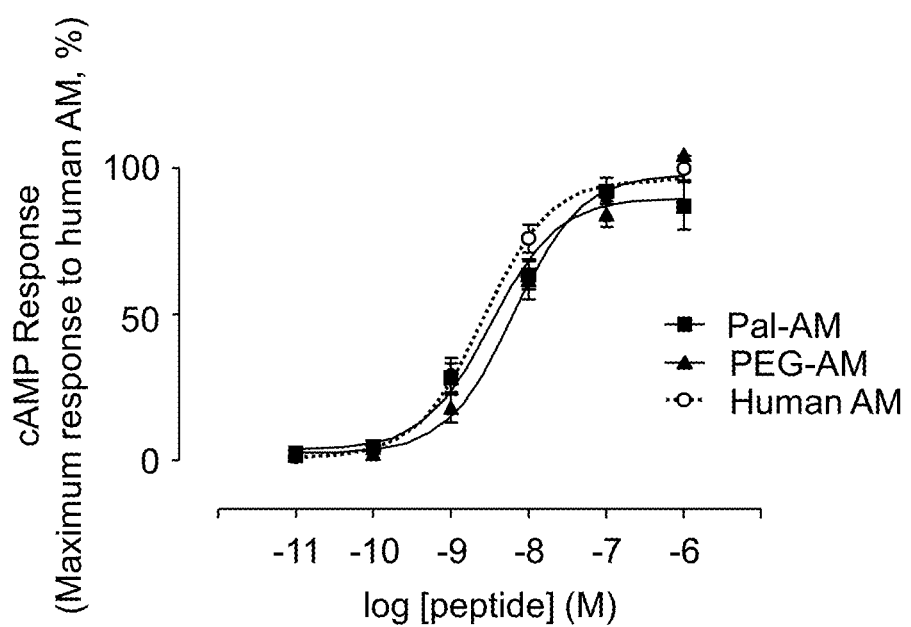
FIG. 1 shows dose response curves of concentration of Pal-h.AM (1-52), PEG5000-h.AM (1-52), or h.AM (1-52) versus increase in cAMP concentration.

The invention relates to a compound represented by formula (I):

or a salt thereof, or a hydrate thereof. In the present specification, the compound represented by formula (I) may be described as "adrenomedullin derivative".

In the invention, adrenomedullin (AM) may not only be a peptide derived from human and isolated and identified from human pheochromocytoma (SEQ ID NO: 1, Non Patent Literature 1), but also be a peptide derived from other non-human mammals such as warm-blooded animals, which is an ortholog, including, for example, pig (SEQ ID NO: 4), dog (SEQ ID NO: 6), cattle (SEQ ID NO: 8), rat (SEQ ID NO: 10), or mouse (SEQ ID NO: 12). In a living body, each of these peptides has a disulfide bond formed by two cysteine residues in the amino acid sequence and is amidated at the C-terminus thereof. In the present specification, the peptide having a disulfide bond and C-terminal amide group may be described as "natural adrenomedullin" or simply "adrenomedullin". The invention can be applied to any of the peptides described above.

In the present specification, "C-terminal amidation" means an aspect of post-translational modification of a peptide in a living body, and specifically means a reaction in which the main chain carboxyl group of C-terminal amino acid residue of the peptide is converted into an amide group. In the present specification, "formation of a disulfide bond between cysteine residues" or "disulfide bond formation by cysteine residues" means an aspect of post-translational modification of the peptide in a living body, and specifically means a reaction in which two cysteine residues in the amino acid sequence of the peptide form a disulfide bond (—S—S—). Many bioactive peptides produced in a living body are initially biosynthesized as a precursor protein with larger molecular weight. The precursor protein is subject to post-translational modifications, such as C-terminal amidation and/or disulfide bond formation by cysteine residues, during the process of intracellular transport to give a mature bioactive peptide. The C-terminal amidation typically proceeds by a C-terminal amidating enzyme that acts on the precursor protein. For a bioactive peptide having a C-terminal amide group, the precursor protein has a Gly residue bound to the C-terminal carboxyl group to be amidated and the Gly residue is converted into the C-terminal amide group by the C-terminal amidating enzyme. The C-terminal propeptide in the precursor protein has a repeat sequence comprising a combination of basic amino acid residues, such as Lys-Arg or Arg-Arg (Mizuno, Journal of Japanese Biochemical Society, 61(12): 1435-1461 (1989)). Disulfide bond formation by cysteine residues can proceed under oxidative conditions. Disulfide bond formation by cysteine residues in a living body typically proceeds by a protein disulfide isomerase that acts on the precursor protein.

Adrenomedullin, a known bioactive substance, is a peptide. This may cause a medicament comprising adrenomedullin as an active ingredient to act effectively in living bodies in subjects such as human patients, only for a very short time. Adrenomedullin has also a strong vasodilatory effect. This strong vasodilatory effect may cause unwanted side reactions, such as excessive decreased blood pressure, tachycardia associated with increased reflex sympathetic nerve activity, and/or increased activity of renin, when a therapeutically effective amount of adrenomedullin is administered in a single dose. To avoid generating the problems described above, a medicament comprising adrenomedullin as an active ingredient is required to be administered to subjects via continuous intravenous infusion. Such a mode of administration may force subjects to bear an undue burden.

The present inventors have found that a compound represented by formula (I), an adrenomedullin derivative, can significantly prolong blood half-life as compared to natural adrenomedullin while retaining bioactivity substantially approximately equivalent to that of natural adrenomedullin. The compound of the invention represented by formula (I), therefore, can be applied to a condition, disease, and/or disorder that can be prevented or treated with adrenomedullin to sustainably prevent or treat the condition, disease, and/or disorder.

In the formula (I), B is required to be a peptide moiety derived from adrenomedullin or a modified form thereof with adrenomedullin activity. In the invention, "a modified form of adrenomedullin" means a peptide chemically modified from natural adrenomedullin as described above. In the invention, "adrenomedullin activity" means bioactivity that adrenomedullin has. The adrenomedullin activity can include the following:

(1) Cardiovascular: a vasodilatory effect, an effect of lowering blood pressure, an effect of increasing cardiac output or improving cardiac insufficiency, an effect of improving pulmonary hypertension, an angiogenic effect, a lymphangiogenic effect, an effect of improving vascular endothelial function, an antiarteriosclerotic effect, a myocardial protective effect such as a myocardial protective effect in ischemic reperfusion disorder or inflammation, an effect of preventing postmyocardial remodeling, an effect of suppressing cardiac hypertrophy, and an effect of suppressing an angiotensin-converting enzyme.

(2) Kidney and water and electrolyte system: a diuretic effect, a natriuretic effect, an effect of suppressing antidiuretic hormone, an aldosterone-reducing effect, a renoprotective effect such as a myocardial protective effect in high blood pressure or ischemic reperfusion disorder, an effect of suppressing drinking behavior, and an effect of suppressing salt requirement.

(3) Brain and nervous system: an effect of neuroprotection and preventing encephalopathy, an anti-inflammatory effect, an effect of suppressing apoptosis such as an effect of suppressing apoptosis in ischemic reperfusion disorder or inflammation, an effect of maintaining autoregulatory capacity, and an effect of suppressing oxidative stress.

(4) Urogenital: an effect of improving erection, an effect of improving blood flow, and an implantation-promoting effect.

(5) Gastrointestinal system: an antiulcer effect, a tissue repair effect, an effect of neogenesis of mucous membrane, an effect of improving blood flow, an anti-inflammatory effect, and an effect of improving liver function.

(6) Orthopedics: an effect of stimulating osteoblast and an effect of improving arthritis.

(7) Endocrine metabolic system: an adipocyte-differentiating effect, an effect of regulating lipolysis, an effect of improving insulin sensitivity, and an effect of controlling insulin secretion.

(8) Others: an effect of improving circulation, an anti-inflammatory effect, an effect of modulating cytokine, an organ protective effect, an effect of suppressing oxidative stress, an effect of repairing tissue such as an anti-decubitus effect, an effect of improving septic shock, an effect of suppressing multiple organ failure, and an effect of suppressing auto-immune disease.

The blood pressure-lowering effect is preferably a vasodilatory hypotensive effect. The anti-inflammatory effect in the gastrointestinal system is preferably an effect of preventing or treating inflammatory bowel diseases including a steroid-resistant or steroid-dependent inflammatory bowel disease, such as ulcerative colitis, Crohn's disease, or intestinal tract Behcet's disease. The adrenomedullin activity will be exerted via increased concentration of intracellular cAMP. Thus, the increased concentration of intracellular cAMP can be considered as an index of adrenomedullin activity. The peptide moiety B derived from adrenomedullin or a modified form thereof having the bioactivity as described above enables the compound of the invention represented by formula (I) to exert bioactivity substantially approximately equivalent to that of natural adrenomedullin, i.e., adrenomedullin activity.

The adrenomedullin or a modified form thereof with adrenomedullin activity is preferably a peptide selected from the group consisting of:

(i) a peptide consisting of an amino acid sequence of adrenomedullin, (ii) a peptide that consists of an amino acid sequence of adrenomedullin and has a disulfide bond formed by two cysteine residues in the amino acid sequence, (iii) a peptide wherein the disulfide bond in the peptide (ii) is substituted with an ethylene group and that has adrenomedullin activity, (iv) a peptide wherein 1 to 15 amino acids in any of the peptides of (i) to (iii) are deleted, substituted or added, and that has adrenomedullin activity, (v) a peptide wherein the C-terminus of any of the peptides of (i) to (iv) is amidated, and (vi) a peptide wherein a glycine residue is added to the C-terminus of any of the peptides of (i) to (iv).

In the peptides of (i) to (vi), a peptide involved in (v) wherein the peptide consists of the amino acid sequence of adrenomedullin, the C-terminus thereof is amidated, and two cysteine residues in the amino acid sequence forms a disulfide bond, represents a mature natural adrenomedullin. A peptide of (i) consisting of an amino acid sequence of adrenomedullin represents a form of natural adrenomedullin prior to post-translational modification including C-terminal amidation and disulfide bond formation by cysteine residues, i.e., an immature form thereof. Other peptides except peptides described above in the peptides of (i) to (vi) represent modified forms of adrenomedullin.

The peptide of (ii) can be formed by oxidizing thiol groups of two cysteine residues in the peptide of (i) with air or with a suitable oxidizing agent to form a disulfide bond. The peptide of (ii) can be used to make the conformation of the peptide moiety B similar to that of natural adrenomedullin. This similar conformation can lead adrenomedullin activity of a compound represented by formula (I) to an activity substantially approximately equivalent to that of natural adrenomedullin.

The peptide of (iii) can be formed by converting the disulfide bond in the peptide of (ii) into an ethylene group. The substitution of the disulfide bond to an ethylene group can be accomplished by any method well known in the art (O. Keller et al., Helv. Chim. Acta, 1974, Volume 57, p. 1253). The peptide of (iii) can be used to stabilize the conformation of peptide moiety B. The stabilized conformation allows a compound represented by formula (I) to sustainably exert adrenomedullin activity in a living body.

In the peptide of (iv), the number of amino acid residues deleted, substituted, or added preferably ranges from 1 to 12, more preferably from 1 to 10, further preferably from 1 to 8, especially preferably from 1 to 5, and most preferably from 1 to 3. A suitable peptide of (iv) is a peptide wherein amino acids at positions 1 to 15, positions 1 to 12, positions 1 to 10, positions 1 to 8, positions 1 to 5, or positions 1 to 3 from the N-terminus of any of the peptides of (i) to (iii) are deleted and that has adrenomedullin activity. The suitable peptide may have further deletion, substitution, or addition of one or more, for example 1 to 5, 1 to 3, or 1 or 2 amino acids. The peptide of (iv) can be used to achieve adrenomedullin activity of a compound represented by formula (I) substantially approximately equivalent to that of natural adrenomedullin. Also, the peptide of (iv) can be used to sustainably exert adrenomedullin activity of a compound represented by formula (I) in a living body.

The peptide of (vi) can be converted to the peptide of (v) by a C-terminal amidating enzyme which can convert a glycine residue at the C-terminus of the peptide of (vi) into an amide group. Therefore, the peptide of (vi) can be administered to a subject to form a peptide amidated at the C-terminus thereof in the living body of the subject after a certain period of time. Thus, a compound represented by formula (I) can sustainably exert adrenomedullin activity in a living body.

The adrenomedullin or a modified form thereof is more preferably a peptide selected from the group consisting of:
(a) a peptide consisting of the amino acid sequence of SEQ ID NO: 1 or a peptide consisting of the amino acid sequence of SEQ ID NO: 1 and having a disulfide bond formed by the cysteine residues at positions 16 and 21;
(b) a peptide consisting of the amino acid sequence of the SEQ ID NO: 4 or a peptide consisting of the amino acid sequence of the SEQ ID NO: 4 and having a disulfide bond formed by the cysteine residues at positions 16 and 21;
(c) a peptide consisting of the amino acid sequence of SEQ ID NO: 6 or a peptide consisting of the amino acid sequence of SEQ ID NO: 6 and having a disulfide bond formed by the cysteine residues at positions 16 and 21;
(d) a peptide consisting of the amino acid sequence of SEQ ID NO: 8 or a peptide consisting of the amino acid sequence of SEQ ID NO: 8 and having a disulfide bond formed by the cysteine residues at positions 16 and 21;
(e) a peptide consisting of the amino acid sequence of SEQ ID NO: 10 or a peptide consisting of the amino acid sequence of SEQ ID NO: 10 and having a disulfide bond formed by the cysteine residues at positions 14 and 19;
(f) a peptide consisting of the amino acid sequence of SEQ ID NO: 12 or a peptide consisting of the amino acid sequence of SEQ ID NO: 12 and having a disulfide bond formed by the cysteine residues at positions 14 and 19;
(g) a peptide wherein the disulfide bond of any of the peptides of (a) to (0 is substituted with an ethylene group, and that has adrenomedullin activity;
(h) a peptide wherein 1 to 15 amino acids of any of the peptides of (a) to (g) are deleted, substituted or added, and that has adrenomedullin activity;
(i) a peptide wherein the C-terminus of any of the peptides of (a) to (h) is amidated; and
(j) a peptide wherein a glycine residue is added to the C-terminus of any of the peptides of (a) to (h).

In the peptide of (h), the number of amino acid residues deleted, substituted, or added preferably ranges from 1 to 12, more preferably from 1 to 10, further preferably from 1 to 8, especially preferably from 1 to 5, and most preferably from 1 to 3. A suitable peptide of (h) is a peptide wherein amino acids at positions 1 to 15, positions 1 to 12, positions 1 to 10, positions 1 to 8, positions 1 to 5, or positions 1 to 3 from the N-terminus of any of the peptides of (a) to (g) are deleted and that has adrenomedullin activity. The suitable peptide may have further deletion, substitution, or addition of one or more, for example 1 to 5, 1 to 3, or 1 or 2 amino acids. The peptide of (h) can be used to achieve adrenomedullin activity of a compound represented by formula (I) substantially approximately equivalent to that of natural adrenomedullin. Also, the peptide of (h) can be used to sustainably exert adrenomedullin activity of a compound represented by formula (I) in a living body.

In the formula (I), A is required to be a modifying group. A is preferably a modifying group selected from the group consisting of a palmitoyl, polyethylene glycol, myristoyl, sugar, and peptide groups. A is more preferably a modifying group selected from the group consisting of a palmitoyl and polyethylene glycol groups. The sugar group is preferably a monovalent group derived from a monosaccharide, disaccharide, oligosaccharide, or polysaccharide, for example glycosyl group. The peptide group is preferably a monovalent group derived from polyglycine, polyglutamic acid, polylysine, or polyasparagine, for example a monovalent group that forms a bond via the N-terminal amino group, the C-terminal carboxyl group, or a side-chain group. The polyethylene glycol group has preferably an average molecular weight ranging from 200 to 40,000, more preferably from 500 to 20,000, and further preferably from 500 to 10,000. A compound represented by formula (I) can sustainably exert adrenomedullin activity for a long period of time in a living body when the average molecular weight of polyethylene glycol group is equal to or greater than 200. The N-terminal amino group of adrenomedullin or a modified form thereof is chemically modified with the modifying group A to result in adrenomedullin activity of the compound represented by formula (I) substantially approximately equivalent to that of natural adrenomedullin. A compound represented by formula (I) can also sustainably exert adrenomedullin activity in a living body.

In the formula (I), L is required to be a divalent linking group. The divalent linking group L is preferably a substituted or unsubstituted divalent hydrocarbon group, more preferably a substituted or unsubstituted divalent aliphatic hydrocarbon group, a substituted or unsubstituted divalent cycloaliphatic group, or a substituted or unsubstituted divalent aromatic group, and further preferably a substituted or unsubstituted $C_1$-$C_{10}$ alkylene group, $C_2$-$C_{10}$ alkenylene group, or $C_2$-$C_{10}$ alkynylene group. The groups preferably comprise one or more heteroatoms and more preferably comprise a divalent group comprising one or more heteroatoms such as oxo (carbonyl), thiocarbonyl, carbamate, or carbonimidoyl. The divalent group comprising one or more heteroatoms is preferably positioned at one or both termini of the divalent linking group L and more preferably positioned at the terminus that is linked to the peptide moiety B. In this case, a compound represented by formula (I) can be cleaved at the divalent linking group L by a metabolism such as hydrolysis in a living body to release adrenomedullin or a modified form thereof with adrenomedullin activity. A particularly suitable divalent linking group L is 1-oxo-1,6-hexanediyl. A compound of the invention represented by formula (I) having the divalent linking group L comprising the properties described above can sustainably exert adrenomedullin activity in a living body.

In the formula (I), n is required to be an integer of 0 or 1. When n is 0, the compound of the invention represented by formula (I) is a compound represented by formula (Ia):

$$A\text{-}B \qquad (Ia).$$

In the formula (Ia), A and B have the same respective meanings as defined in the formula (I).

In the formula (I), the peptide moiety B is required to be linked to the modifying group A or the linking group L via a group in the region near the N-terminus of the peptide moiety B. The peptide moiety B is preferably linked to the modifying group A or the linking group L via the N-terminal amino group of the peptide moiety B. In the invention, "a group in the region near the N-terminus" of the peptide moiety B means a certain group of an amino acid residue contained in the region of 13 amino acid residues from the N-terminal amino acid residue of the peptide moiety B, such as α-amino group of the N-terminal amino acid residue or a side-chain amino, carboxyl, hydroxyl, imidazole, or guanidyl group of each amino acid residue, and a modifying group bound to the amino acid residue.

In the invention, "the N-terminal amino group of the peptide moiety B" means the α-amino group of the N-terminal amino acid residue of the peptide moiety B. The linkage form described above allows a compound of the invention represented by formula (I) to sustainably exert adrenomedullin activity in the living body.

In a particularly suitable compound represented by formula (I),
A is a modifying group that is a palmitoyl group;
n is 0; and
B is a peptide moiety derived from adrenomedullin or a modified form thereof with adrenomedullin activity;
wherein the peptide moiety B is bound to the modifying group A via the N-terminal amino group of the peptide moiety B, or
A is a modifying group that is a polyethylene glycol group;
L is a divalent linking group that is a substituted or unsubstituted divalent hydrocarbon group and wherein the divalent hydrocarbon group comprises one or more heteroatoms;
n is 1; and
B is a peptide moiety derived from adrenomedullin or a modified form thereof with adrenomedullin activity,
wherein the peptide moiety B is bound to the modifying group A or the linking group L via the N-terminal amino group of the peptide moiety B.

In the invention, compounds represented by formula (I) include not only the compounds themselves but also salts thereof. When compounds represented by formula (I) are in the form of salt, they are preferably pharmaceutically acceptable salts. Counterions in salts of the compounds of the invention preferably include, but are not limited to, for example, cations such as a sodium, potassium, calcium, magnesium, or substituted or unsubstituted ammonium ion, or anions such as a chloride, bromide, iodide, phosphate, nitrate, sulfate, carbonate, bicarbonate, perchlorate, formate, acetate, trifluoroacetate, propionate, lactate, maleate, hydroxymaleate, methylmaleate, fumarate, adipate, benzoate, 2-acetoxybenzoate, p-aminobenzoate, nicotinate, cinnamate, ascorbate, pamoate, succinate, salicylate, bismethylenesalicylate, oxalate, tartrate, malate, citrate, gluconate, aspartate, stearate, palmitate, itaconate, glycolate, glutamate, benzenesulfonate, cyclohexylsulfamate, methanesulfonate, ethanesulfonate, isethionate, benzenesulfonate, p-toluenesulfonate, or naphthalenesulfonate ion. When compounds represented by formula (I) are in the form of salt with any of the counterions, adrenomedullin activity of the compounds can be substantially approximately equivalent to that of natural adrenomedullin.

Compounds represented by formula (I) include not only the compounds themselves but also solvates of the compounds or salts thereof. When compounds represented by formula (I) or salts thereof are in the form of solvate, they are preferably pharmaceutically acceptable solvates. Solvents that can form solvates with the compounds or salts thereof include, but are not limited to, for example, water or organic solvents such as methanol, ethanol, 2-propanol (isopropyl alcohol), dimethyl sulfoxide (DMSO), acetic acid, ethanolamine, acetonitrile, or ethyl acetate. When compounds represented by formula (I) or salts thereof are in the form of solvate with any of the solvents described above, adrenomedullin activity of the compounds can be substantially approximately equivalent to that of natural adrenomedullin.

Compounds represented by formula (I) include not only the compounds themselves described above or below but also protected forms thereof. In the present specification, a "protected form" means a form in which any suitable protecting group is introduced into one or more functional groups of the compound such as a side-chain amino group of lysine residue. In the present specification, a "protecting group" means a group that is introduced into a specific functional group to prevent any unwanted reaction from proceeding, will be removed quantitatively under a specific reaction condition, and is substantially stable, or inactive, under any reaction condition other than the specific reaction condition. Protecting groups that can form protected forms of the compounds include, but are not limited to, for example, t-butoxycarbonyl (Boc), 2-bromobenzyloxycarbonyl (BrZ), 9-fluorenylmethoxycarbonyl (Fmoc), p-toluenesulfonyl (Tos), benzyl (Bzl), 4-methylbenzyl (4-MeBzl), 2-chlorobenzyloxycarbonyl (ClZ), cyclohexyl (cHex), and phenacyl (Pac); other protecting groups of amino groups include benzyloxycarbonyl, p-chlorobenzyloxycarbonyl, p-bromobenzyloxycarbonyl, p-nitrobenzyloxycarbonyl, p-methoxybenzyloxycarbonyl, benzhydryloxycarbonyl, 2-(p-biphenyl)isopropyloxycarbonyl, 2-(3,5-dimethoxyphenyl)isopropyloxycarbonyl, p-phenylazobenzyloxycarbonyl, triphenylphosphonoethyloxycarbonyl, 9-fluorenylmethyloxycarbonyl, t-amyloxyoxycarbonyl, diisopropylmethyloxycarbonyl, isopropyloxycarbonyl, ethyloxycarbonyl, allyloxycarbonyl, 2-methylsulfonylethyloxycarbonyl, 2,2,2-trichloroethyloxycarbonyl, cyclopentyloxycarbonyl, cyclohexyloxycarbonyl, adamantyloxycarbonyl, isobornyloxycarbonyl, benzenesulfonyl, mesitylenesulfonyl, methoxytrimethylphenylsulfonyl, 2-nitrobenzensulfonyl, 2-nitrobenzenesulfenyl, 4-nitrobenzensulfonyl, and 4-nitrobenzene sulfenyl; other protecting groups of carboxyl groups include methyl esters, ethyl esters, t-butyl esters, p-methoxybenzyl esters, and p-nitrobenzyl esters; other side-chain protecting groups of Arg include 2,2,4,6,7-pentamethyl-2,3-dihydrobenzofuran-5-sulfonyl, 4-methoxy-2,3,6-trimethylbenzenesulphonyl, 2,2,5,7,8-pentamethylchroman-6-sulfonyl, and 2-methoxybenzenesulfonyl; other protecting groups of Tyr include 2,6-dichlorobenzyl, t-butyl, and cyclohexyl; other protecting groups of Cys include 4-methoxybenzyl, t-butyl, trityl, acetamidomethyl, and 3-nitro-2-pyridine sulfenyl; other protecting groups of His include benzyloxymethyl, p-methoxybenzyloxymethyl, t-butoxymethyl, trityl, and 2,4-dinitrophenyl; and other protecting groups of Ser and Thr include t-butyl. When a compound represented by formula (I) is in a protected form with any of the protecting groups described above, adrenomedullin activity of the compound can be substantially approximately equivalent to that of natural adrenomedullin.

Compounds represented by formula (I) include individual enantiomers and diastereomers of the compounds, and mixtures of stereoisomers of the compounds such as racemates.

The properties described above enable the compound represented by formula (I) to sustainably exert adrenomedullin activity in a living body without substantially decreasing adrenomedullin activity.

<2. Pharmaceutical Use of Adrenomedullin Derivatives>

A compound of the invention represented by formula (I) can sustainably exert bioactivity substantially approximately equivalent to that of adrenomedullin, which is the parent molecule of the compound, i.e., adrenomedullin activity, in a living body. Therefore, the invention relates to a medicament comprising a compound of the invention represented by formula (I) as an active ingredient.

A compound of the invention represented by formula (I) may be used alone or in combination with one or more pharmaceutically acceptable components when the compound is applied to pharmaceutical use. A medicament of the invention can be formulated into various dosage forms commonly used in the art depending on the desired mode of administration. Thus, the medicament of the invention can also be provided in the form of a pharmaceutical composition comprising a compound of the invention represented by formula (I) and one or more pharmaceutically acceptable carriers. Pharmaceutical compositions of the invention may comprise, in addition to the components described above, one or more pharmaceutically acceptable carriers, excipients, binders, vehicles, dissolution aids, preservatives, stabilizers, bulking agents, lubricants, surfactants, oily liquids, buffering agents, soothing agents, antioxidants, sweetening agents, flavoring agents, and so forth.

Dosage forms of medicaments comprising a compound of the invention represented by formula (I) as an active ingredient are not particularly limited and may be a formulation for parenteral or oral administration. Dosage forms of medicaments of the invention may also be a formulation in unit dosage form or in multiple dosage form. Formulations for use in parenteral administration include, for example, injections such as sterile solutions or suspensions in water or any other pharmaceutically acceptable liquid. Additive agents that can be admixed into the injections include, but are not limited to, for example, vehicles such as physiological saline and isotonic solutions comprising glucose or other adjuvants, e.g. D-sorbitol, D-mannitol, or sodium chloride; dissolution aids such as alcohols, e.g. ethanol or benzyl alcohol, esters, e.g. benzyl benzoate, and polyalcohols, e.g. propylene glycol or polyethylene glycol; nonionic surfactants such as polysorbate 80 or polyoxyethylene hydrogenated castor oil; oily liquids such as sesame oil or soybean oil; buffering agents such as phosphate buffer or sodium acetate buffer; soothing agents such as benzalkonium chloride or procaine hydrochloride; stabilizers such as human serum albumin or polyethylene glycol; preservatives; and antioxidants. The prepared injection will be generally filled in any suitable vial, e.g. an ampule and preserved under an appropriate environment until use.

The formulations for use in oral administration include, for example, a tablet optionally coated with sugar coating or soluble film, a capsule, an elixir, a microcapsule, a tablet, a syrup, and a suspension. Additive agents that can be admixed into tablets or capsules and so forth include, but are not limited to, for example, binders such as gelatin, cornstarch, gum tragacanth, and gum arabic; excipients such as crystalline cellulose; bulking agents such as cornstarch, gelatin, and alginate; lubricants such as magnesium stearate; sweetening agents such as sucrose, lactose, or saccharin; and flavoring agents such as peppermint, *Gaultheria* adenothrix oil, or cherry. A formulation may further include liquid carriers such as oils/fats when the formulation is in the form of a capsule.

The compound of the invention represented by formula (I) can sustainably exert adrenomedullin activity substantially approximately equivalent to that of adrenomedullin, which is the parent molecule of the compound, in a living body. Thus, a medicament comprising a compound of the invention represented by formula (I) as an active ingredient can be formulated into a depot formulation. In this case, the medicament of the invention in the dosage form of depot formulation can, for example, be implanted subcutaneously or intramuscularly or administered by intramuscular injection. The depot formulation of the medicament of the invention allows the compound of the invention represented by formula (I) to sustainably exert adrenomedullin activity for a long period of time.

The medicament comprising a compound of the invention represented by formula (I) as an active ingredient can be combined with one or more other drugs useful as medicaments. In this case, the medicament of the invention may be provided in the form of a single medicament comprising the compound of the invention represented by formula (I) and one or more other drugs, or may be provided in the form of a medicament combination or kit comprising a plurality of formulations into which the compound of the invention represented by formula (I) and one or more other drugs are separately formulated. For the medicament combination or kit, each formulation can be administered simultaneously or separately such as sequentially.

For applying compounds of the invention represented by formula (I) to pharmaceutical use, the compounds represented by formula (I) include not only the compounds themselves but also pharmaceutically acceptable salts thereof and pharmaceutically acceptable solvates thereof. The pharmaceutically acceptable salts of compounds of the invention represented by formula (I) and pharmaceutically acceptable solvates thereof preferably include, but are not limited to, for example, salts or solvates exemplified above. When compounds represented by formula (I) are in the form of any of the salts or solvates described above, the compounds can be applied to the desired pharmaceutical use.

A medicament comprising a compound of the invention represented by formula (I) as an active ingredient can prevent or treat various conditions, diseases, and/or disorders that will be prevented or treated with adrenomedullin. The conditions, diseases, and/or disorders include, but are not limited to, for example, the following:

(1) Cardiovascular diseases: cardiac insufficiency, pulmonary hypertension, arteriosclerosis obliterans, Buerger's disease, myocardial infarction, lymphedema, Kawasaki's disease, myocarditis, high blood pressure, organ dysfunctions due to high blood pressure, and arteriosclerosis.

(2) Kidney and water and electrolyte system disorders: kidney failure and nephritis.

(3) Brain and nervous system diseases: cerebral infarction and encephalitis.

(4) Urogenital diseases: erectile dysfunction (ED).

(5) Gastrointestinal diseases: inflammatory bowel disease, ulcerative disease, intestinal Behcet's disease, and hepatic failure.

(6) Orthopedic disease: arthritis.

(7) Endocrine metabolic disease: diabetes and organ dysfunctions due to diabetes.

(8) Others: septic shock, auto-immune disease, multiple organ failure, and pressure sore.

The cardiovascular disease is preferably any of myocardial infarction, pulmonary hypertension, and cardiac insufficiency. The gastrointestinal disease is preferably any of inflammatory diseases including a steroid-resistant or steroid-dependent inflammatory bowel disease such as ulcerative colitis, Crohn's disease, or intestinal tract Behcet's disease.

A compound of the invention represented by formula (I) has a structure in which adrenomedullin, which is a natural bioactive peptide, is linked to a modifying group. This structure allows the compound of the invention represented by formula (I) to be safe and have low toxicity. Therefore, the medicament comprising the compound of the invention represented by formula (I) as an active ingredient can be applied to various subjects in need of prevention or treatment of the condition, disease, and/or disorder. The subjects are preferably human or non-human mammalian subjects or patients such as warm-blooded animal including pig, dog, cattle, rat, mouse, guinea pig, rabbit, chicken, sheep, cat, monkey, hamadryas baboon, or chimpanzee. The medicament of the invention can be administered to the subjects to prevent or treat various conditions, diseases, and/or disorders that will be prevented or treated with adrenomedullin.

In the present specification, "prevention" means that onset (development or occurrence) of a condition, disease, and/or disorder will be substantially precluded. On the other hand, in the present specification, "treatment" means suppression such as suppression of progression, remission, restoration, and/or cure of a condition, disease, and/or disorder that has appeared (developed or occurred).

The compound of the invention represented by formula (I) can be used to prevent or treat the condition, disease, and/or disorder described above such as a cardiovascular disease, peripheral vascular disease, or inflammatory disease in subjects with the condition, disease, and/or disorder. Therefore, the medicament of the invention is preferably a medicament for use in the prevention or treatment of the condition, disease, and/or disorder described above and is more preferably a medicament for use in the prevention or treatment of a cardiovascular disease, an inflammatory disease, or a peripheral vascular disease. The invention also relates to an agent for preventing or treating a cardiovascular disease, an inflammatory disease, or a peripheral vascular disease comprising a compound of the invention represented by formula (I) as an active ingredient. The compound of the invention represented by formula (I) can be used to prevent or treat the condition, disease, and/or disorder described above to sustainably prevent or treat the condition, disease, and/or disorder.

Compounds of the invention represented by formula (I) can be used to prevent or treat the condition, disease, and/or disorder described above such as a cardiovascular disease, peripheral vascular disease, or inflammatory disease in subjects with the condition, disease, and/or disorder. Therefore, one embodiment of the invention is a method for preventing or treating the disease or condition described above, comprising administering an effective amount of a compound of the invention represented by formula (I) or a pharmaceutically acceptable salt thereof, or a pharmaceutically acceptable hydrate thereof to a subject in need of prevention or treatment of the condition, disease, and/or disorder described above. The condition, disease, and/or disorder is preferably any of cardiovascular diseases, peripheral vascular diseases, and inflammatory diseases. Compounds of the invention represented by formula (I) can be administered to subjects in need of prevention or treatment of the condition, disease, and/or disorder to prevent or treat the condition, disease, and/or disorder.

Another embodiment of the invention is a compound of the invention represented by formula (I) or a pharmaceutically acceptable salt thereof, or a pharmaceutically acceptable hydrate thereof for use in the prevention or treatment of the condition, disease, and/or disorder described above. An alternative embodiment of the invention is use of a compound of the invention represented by formula (I) or a pharmaceutically acceptable salt thereof, or a pharmaceutically acceptable hydrate thereof in the manufacture of a medicament for the prevention or treatment of the condition, disease, and/or disorder described above. The condition, disease, and/or disorder is preferably any of cardiovascular diseases, inflammatory diseases, and peripheral vascular diseases. The medicament of the invention can be used to prevent or treat the condition, disease, and/or disorder described above to sustainably prevent or treat the condition, disease, and/or disorder.

When a medicament comprising a compound of the invention represented by formula (I) as an active ingredient is administered to a subject, particularly a human patient, the precise amount and number of doses will be determined considering many factors including age and sex of the subject, the precise condition, such as severity, of the condition, disease, and/or disorder to be prevented or treated, and the route of administration. The therapeutically effective amount and number of doses should be ultimately determined by the attending physician. Therefore, the compound represented by formula (I), which is an active ingredient in the medicament of the invention, will be administered to the subject in the therapeutically effective amount and number of doses. For example, when the medicament of the invention is administered to a human patient, an amount of the compound represented by formula (I), which is an active ingredient, will usually range from 0.01 to 100 mg per 60 kg of body weight per day and typically from 0.01 to 10 mg per 60 kg of body weight per day.

Route of administration and number of doses of a medicament comprising a compound of the invention represented by formula (I) as an active ingredient are not particularly limited and the medicament may be administered orally or parenterally in a single dose or in multiple doses. The medicament of the invention is preferably administered parenterally such as intravenously, by intestinal infusion, subcutaneously, intramuscularly, or intraperitoneally, and more preferably intravenously or subcutaneously. The medicament of the invention is also preferably administered in a single dose. The medicament of the invention is particularly preferably used in intravenous or subcutaneous administration in a single dose. Adrenomedullin, which is the parent molecule of compounds of the invention represented by formula (I), has a strong vasodilatory effect. This strong vasodilatory effect may cause unwanted side reactions such as excessive decreased blood pressure, tachycardia associated with increased reflex sympathetic nerve activity, and/or increased activity of renin when a therapeutically effective amount of adrenomedullin is administered in a single dose. On the other hand, the compounds of the invention represented by formula (I) can significantly prolong blood half-life as compared to natural adrenomedullin while retaining adrenomedullin activity substantially approximately equivalent to that of natural adrenomedullin. Therefore, intravenous administration of the medicament comprising a compound of the invention represented by formula (I) as an active ingredient to a subject in a single dose allows the medicament to sustainably prevent or treat a condition, disease, and/or disorder in the subject while suppressing unwanted side reactions due to the vasodilation effect of adrenomedullin.

<3. Method for Producing Adrenomedullin Derivatives>

The invention also relates to a method for producing a compound of the invention represented by formula (I).

[3-1. Step of Preparing Precursors]

The method of the invention may comprise preparing at least any of a precursor of peptide moiety B derived from adrenomedullin or a modified form thereof, a precursor of modifying group A selected from the group consisting of a palmitoyl group and a polyethylene glycol group, and a precursor of divalent group $L_n$.

In the invention, "a precursor of peptide moiety B derived from adrenomedullin or a modified form thereof", "a precursor of modifying group A selected from the group consisting of a palmitoyl group and a polyethylene glycol group" and "a precursor of divalent group $L_n$" means respectively adrenomedullin or a modified form thereof, palmitic acid or polyethylene glycol, and H-$L_n$-H or, alternatively, means derivatives of the peptide moiety B, modifying group A, and divalent group $L_n$ that have been suitably modified or activated so that the peptide moiety B, modifying group A, and divalent group $L_n$ are linked together at one or both ends thereof via condensation reactions in the linking step as described below. The precursor of peptide moiety B is preferably adrenomedullin or a modified form thereof itself, or a protected form thereof. The precursor of modifying group A is preferably palmitic acid or polyethylene glycol itself, an activated derivative thereof, or a protected form thereof. When the modifying group A is a palmitoyl group, the modifying group A is preferably an acid halide of palmitic acid such as palmitoyl chloride. The precursor of divalent group $L_n$ is preferably a hydrogenated form of divalent group $L_n$, $H-L_n-H$, itself, an activated derivative thereof, or a protected form thereof. When the divalent group $L_n$ is 1-oxo-1,6-hexanediyl wherein n is 1, the precursor of divalent group $L_n$ is preferably an active ester, for example, 6-chlorohexanoic acid N-hydroxysuccinimide ester. The precursor has preferably any protecting group described above when the precursor is in a protected form. Preparation of precursors having properties described above in this step allows high-yield reactions of linking each precursor in the linking step described below.

In this step, the precursor of peptide moiety B derived from adrenomedullin or a modified form thereof can be prepared by any means commonly used in the art. The means may be, for example, a peptide synthesis method on solid phase system or in liquid phase system, or a method for purifying natural peptides from human or non-human mammalian tissues or cells that can produce adrenomedullin when the precursor of peptide moiety B is adrenomedullin or a modified form thereof itself. Alternatively, the means may be a method for overexpression of a recombinant protein using DNA encoding adrenomedullin in human or non-human mammal that can produce adrenomedullin, such as SEQ ID NO: 2, 5, 7, 9, 11, or 13, in a transformation system such as *Escherichia coli* or *Saccharomyces cerevisiae*. Alternatively, the already produced peptides may be also purchased. In any case, the peptides will be included in the embodiment of this step.

A precursor that has a disulfide bond formed by two cysteine residues in the amino acid sequence in the precursor of peptide moiety B prepared by the means described above can be obtained by disulfide bond formation between thiol groups of two cysteine residues in the amino acid sequence. A precursor in which the disulfide bond formed between two cysteine residues in the amino acid sequence of the precursor of peptide moiety B prepared by the means described above has been substituted with an ethylene group can be obtained by substitution of the disulfide bond with an ethylene group. The formation reaction of a disulfide bond and the substitution reaction with an ethylene group can be performed based on any condition commonly used in the art. The formation reaction of a disulfide bond and the substitution reaction with an ethylene group may be performed in this step or in the linking step described below. In any case, the precursors will be included in the embodiment of the step.

When at least any of the precursor of peptide moiety B, the precursor of modifying group A, and the precursor of divalent group $L_n$ are in a protected form, the protection step in which one or more protecting groups are introduced into at least any of the precursor of peptide moiety B, the precursor of modifying group A, and the precursor of divalent group $L_n$ and/or the deprotection step in which at least any of one or more protecting groups in protected forms of the precursor of peptide moiety B, the precursor of modifying group A, and the precursor of divalent group $L_n$ are deprotected may be performed in this step as desired. The protection and deprotection steps can be performed with any protection and deprotection reaction commonly used in the art. The protection and deprotection steps may be performed in this step or in the linking step described below. Any case described above will be included in the embodiment of this step.

[3-2. Linking Step]

The method of the invention is required to comprise a linking step of linking the precursor of peptide moiety B derived from adrenomedullin or a modified form thereof, the precursor of modifying group A selected from the group consisting of a palmitoyl group and a polyethylene glycol group, and the precursor of divalent group $L_n$ to give a compound represented by formula (I).

When n is 0 in the formula (I), this step will be performed by linking the precursor of peptide moiety B and the precursor of modifying group A. When n is 1 in the formula (I), this step will be performed by linking the precursor of peptide moiety B, the precursor of modifying group A, and the precursor of divalent group $L_n$.

In this step, means of linking the precursor of peptide moiety B, the precursor of modifying group A, and the precursor of divalent group $L_n$ is not particularly limited. The means can be a reaction of forming peptide linkage using any precursor commonly used in the art such as an acid halide e.g., an acid chloride or an active ester e.g., N-hydroxysuccinimide ester.

When n is 1 in the formula (I), the order of linking the precursor of peptide moiety B, the precursor of modifying group A, and the precursor of divalent group $L_n$ is not particularly limited. For example, the precursor of modifying group A and the precursor of divalent group $L_n$ can be first linked before further linking the linked precursors and the precursor of peptide moiety B. Alternatively, the precursor of peptide moiety B and the precursor of divalent group $L_n$ can be first linked before further linking the linked precursors and the precursor of modifying group A. Any case described above will be included in the embodiment of the step.

EXAMPLES

Hereinafter, the present invention will be described further specifically with reference to Examples. However, the technical scope of the present invention is not intended to be limited by these Examples.

<I: Preparation of Compound>

A precursor of group B derived from adrenomedullin (AM) was synthesized according to the scheme given below. A peptide corresponding to amino acid residues 1 to 52 of human adrenomedullin (h.AM(1-52)) was divided into 6 segments (Seg-1 to Seg-6). After synthesis of each segment, these segments were condensed to synthesize a precursor peptide of group B. Then, a palmitoyl group (Pal) or a polyethylene glycol group (PEG) was linked to the precursor peptide of group B to synthesize an adrenomedullin derivative.

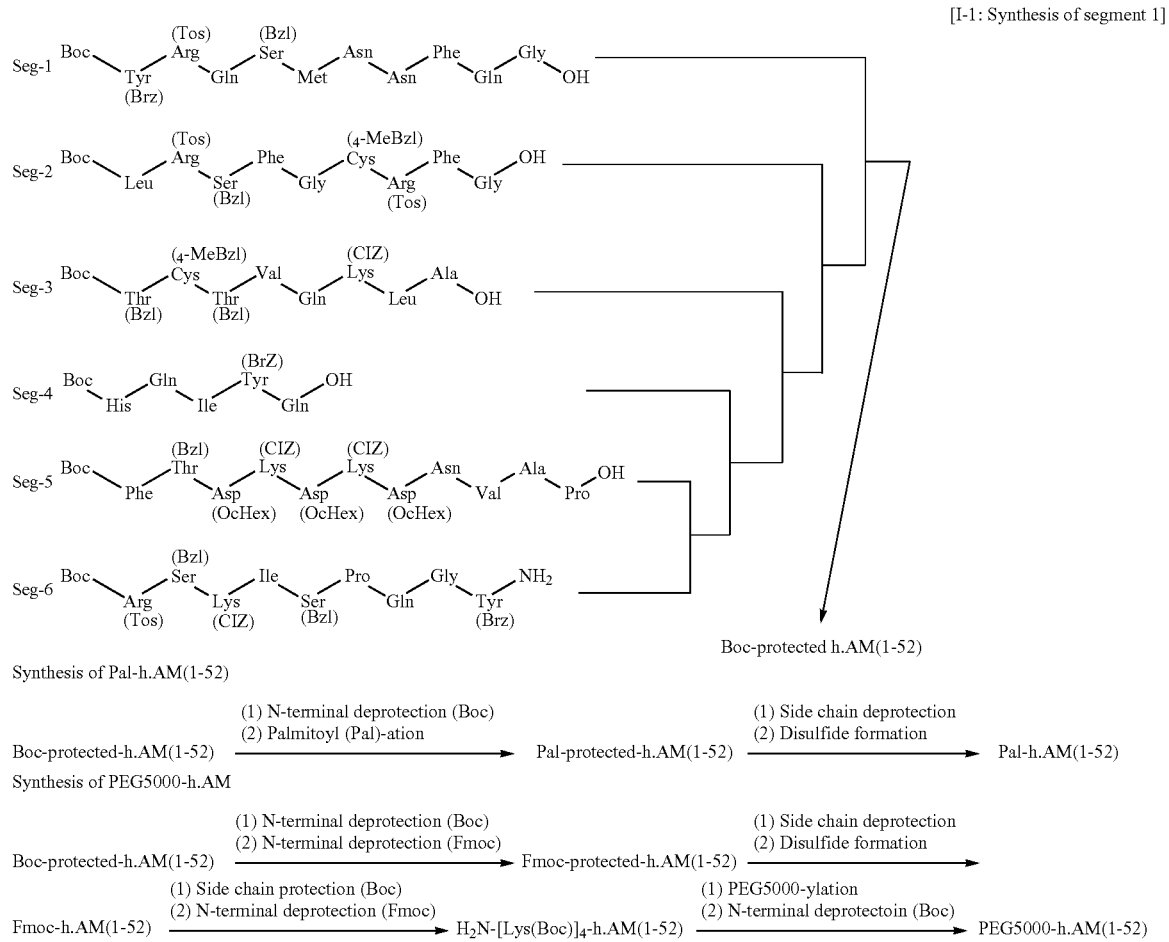

[I-1: Synthesis of segment 1]

Boc-Gln-Gly-OPac

Boc-Gly-OPac (88.0 g) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (65.5 mL) was added to the residue. Diethyl ether was added to the obtained mixture. The deposited precipitate was collected by filtration and washed with diethyl ether. The obtained hydrochloride salt was dissolved in N,N-dimethylformamide. Boc-Gln-OH (81.3 g) and 1-hydroxybenzotriazole (48.7 g) were added to the obtained solution. 1-Ethyl-3-(3-dimethylaminopropyl)carbodiimide (65.9 mL) was added dropwise to the mixture under cooling. The reaction solution was stirred at room temperature for 3 hours. The N,N-dimethylformamide was distilled off under reduced pressure. Ethyl acetate was added to the residue, and the obtained solution was diluted. This solution was washed with a 5% aqueous sodium bicarbonate solution, a 0.5 N aqueous hydrochloric acid solution and saturated saline. The organic layer was dried over MgSO$_4$, and then the ethyl acetate was distilled off under reduced pressure. Diethyl ether was added to the residue. The deposited precipitate was collected by filtration and washed with diethyl ether. The obtained crystals were dissolved in a chloroform/methanol mixed solution. The solvent was distilled off under reduced pressure. Diethyl ether was added to the residue. The deposited precipitate was collected by filtration and washed with diethyl ether. These procedures yielded 56 g of the product of interest.

Boc-Phe-Gln-Gly-OPac

Boc-Gln-Gly-OPac (54.8 g) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (28 mL) was added to the residue. Diethyl ether was added to the obtained mixture. The deposited precipitate was collected by filtration and washed with diethyl ether. The obtained hydrochloride salt was dissolved in N,N-dimethylformamide. Boc-Phe-OH (35.2 g) and 1-hydroxybenzotriazole (19.3 g) were added to the obtained solution. 1-Ethyl-3-(3-dimethylaminopropyl)carbodiimide (26.2 mL) was added dropwise to the mixture under cooling. The reaction solution was stirred at room temperature for 4 hours. Water was added to the reaction solution. The deposited precipitate was collected by filtration and washed with water and diethyl ether. The obtained crystals were dissolved in a chloroform/methanol mixed solution. The solvent was distilled off under reduced pressure. Diethyl ether was added to the residue. The deposited precipitate was collected by filtration and washed with diethyl ether. These procedures yielded 68.7 g of the product of interest.

Boc-Asn-Phe-Gln-Gly-OPac (SEQ ID NO: 48)

Boc-Phe-Gln-Gly-OPac (67.9 g) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (26 mL) was added to the residue. Diethyl ether was added to the obtained mixture. The deposited precipitate was collected by filtration and washed with diethyl ether. The obtained hydrochloride salt was dissolved in N,N-dimethylformamide. Boc-Asn-OH (30.5 g) and 1-hydroxybenzotriazole (19.4 g) were added to the obtained solution. 1-Ethyl-3-(3-dimethylaminopropyl)carbodiimide (21.8 mL) was added dropwise to the mixture under cooling. The reaction solution was stirred overnight at room temperature. Water was added to the reaction solution. The deposited precipitate was collected by filtration and washed with water and diethyl ether. The obtained crystals were dissolved in N,N-dimethylformamide. The solvent was distilled off under reduced pressure. Diethyl ether was added to the residue. The deposited precipitate was collected by filtration and washed with diethyl ether. These procedures yielded 81 g of the product of interest.

Boc-Asn-Asn-Phe-Gln-Gly-OPac (SEQ ID NO: 49)

Boc-Asn-Phe-Gln-Gly-OPac (81 g) (SEQ ID NO: 48) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (26 mL) was added to the residue. Diethyl ether was added to the obtained mixture. The deposited precipitate was collected by filtration and washed with diethyl ether. The obtained hydrochloride salt was dissolved in a N,N-dimethylformamide/1,3-dimethyl-2-imidazolidinone mixed solution. Boc-Asn-OH (28.9 g) and 1-hydroxybenzotriazole (19.2 g) were added to the obtained solution. 1-Ethyl-3-(3-dimethylaminopropyl)carbodiimide (26.0 mL) was added dropwise to the mixture under cooling. The reaction solution was stirred overnight at room temperature. Water was added to the reaction solution. The deposited precipitate was collected by filtration and washed with water, acetonitrile and diethyl ether. These procedures yielded 74 g of the product of interest.

Boc-Met-Asn-Asn-Phe-Gln-Gly-OPac (SEQ ID NO: 14)

Boc-Asn-Asn-Phe-Gln-Gly-OPac (50.0 g) (SEQ ID NO: 49) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (13.7 mL) was added to the residue. Diethyl ether was added to the obtained mixture. The deposited precipitate was collected by filtration and washed with diethyl ether. The obtained hydrochloride salt was dissolved in a N,N-dimethylformamide/1-methyl-2-pyrrolidone/1,3-dimethyl-2-imidazolidinone mixed solution. Boc-Met-OH (16.4 g) and 1-hydroxybenzotriazole (9.4 g) were added to the obtained solution. 1-Ethyl-3-(3-dimethylaminopropyl)carbodiimide (12.6 mL) was added dropwise to the mixture under cooling. The reaction solution was stirred overnight at room temperature. Water was added to the reaction solution. The deposited precipitate was collected by filtration and washed with water, acetonitrile and diethyl ether. These procedures yielded 54 g of the product of interest.

Boc-Ser(Bzl)-Met-Asn-Asn-Phe-Gln-Gly-OPac (SEQ ID NO: 15)

Boc-Met-Asn-Asn-Phe-Gln-Gly-OPac (53.0 g) (SEQ ID NO: 14) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (12.5 mL) was added to the residue. Diethyl ether was added to the obtained mixture. The deposited precipitate was collected by filtration and washed with diethyl ether. The obtained hydrochloride salt was dissolved in a 1-methyl-2-pyrrolidone/1,3-dimethyl-2-imidazolidinone mixed solution. Boc-Ser(Bzl)-OH (17.7 g) and 1-hydroxybenzotriazole (8.5 g) were added to the obtained solution. 1-Ethyl-3-(3-dimethylaminopropyl)carbodiimide (11.5 mL) was added dropwise to the mixture under cooling. The reaction solution was stirred overnight at room temperature. Water was added to the reaction solution. The deposited precipitate was collected by filtration and washed with water, acetonitrile and diethyl ether. These procedures yielded 56.5 g of the product of interest.

Boc-Gln-Ser(Bzl)-Met-Asn-Asn-Phe-Gln-Gly-OPac (SEQ ID NO: 16)

Boc-Ser(Bzl)-Met-Asn-Asn-Phe-Gln-Gly-OPac (30.0 g) (SEQ ID NO: 15) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (5.9 mL) was added to the residue. Diethyl ether was added to the obtained mixture. The deposited precipitate was collected by filtration and washed with diethyl ether. The obtained hydrochloride salt was dissolved in a dimethyl sulfoxide/1-methyl-2-pyrrolidone/1,3-dimethyl-2-imidazolidinone mixed solution. Boc-Gln-OH (7.3 g) and 1-hydroxybenzotriazole (5.5 g) were added to the obtained solution. 1-Ethyl-3-(3-dimethylaminopropyl)carbodiimide (7.5 mL) was added dropwise to the mixture under cooling. The reaction solution was stirred overnight at room temperature. Water was added to the reaction solution. The deposited precipitate was collected by filtration and washed with water, acetonitrile and diethyl ether. These procedures yielded 24.0 g of the product of interest.

Boc-Arg(Tos)-Gln-Ser(Bzl)-Met-Asn-Asn-Phe-Gln-Gly-OPac (SEQ ID NO: 17)

Boc-Gln-Ser(Bzl)-Met-Asn-Asn-Phe-Gln-Gly-OPac (16.2 g) (SEQ ID NO: 16) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (2.9 mL) was added to the residue. Diethyl ether was added to the obtained mixture. The deposited precipitate was collected by filtration and washed with diethyl ether. The obtained hydrochloride salt was dissolved in a dimethyl sulfoxide/1-methyl-2-pyrrolidone mixed solution. Boc-Arg(Tos)-OH (7.4 g) and 1-hydroxybenzotriazole (2.1 g) were added to the obtained solution. 1-Ethyl-3-(3-dimethylaminopropyl)carbodiimide (2.9 mL) was added dropwise to the mixture under cooling. The reaction solution was stirred overnight at room temperature. Water was added to the reaction solution. The deposited precipitate was collected by filtration and washed with water, acetonitrile and diethyl ether. These procedures yielded 12.5 g of the product of interest.

Boc-Tyr(BrZ)-Arg(Tos)-Gln-Ser(Bzl)-Met-Asn-Asn-Phe-Gln-Gly-OPac (SEQ ID NO: 18)

Boc-Arg(Tos)-Gln-Ser(Bzl)-Met-Asn-Asn-Phe-Gln-Gly-OPac (12.5 g) (SEQ ID NO: 17) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (1.7 mL) was added to the residue. Diethyl ether was added to the obtained mixture. The deposited precipitate was collected by filtration and washed with diethyl ether. The obtained hydrochloride salt was dissolved in a dimethyl sulfoxide/1-methyl-2-pyrrolidone mixed solution. Boc-Tyr(BrZ)-OH (4.4 g) and 1-hydroxybenzotriazole (1.5 g) were added to the obtained solution. 1-Ethyl-3-(3-dimethylaminopropyl)carbodiimide (1.7 mL) was added dropwise to the mixture under cooling. The reaction solution was stirred overnight at room temperature. Acetonitrile was added to the reaction solution. The deposited precipitate was collected by filtration and washed with acetonitrile and diethyl ether. These procedures yielded 11 g of the product of interest.

Boc-Tyr(BrZ)-Arg(Tos)-Gln-Ser(Bzl)-Met-Asn-Asn-Phe-Gln-Gly-OH (segment 1) (SEQ ID NO: 18)

Boc-Arg(Tos)-Gln-Ser(Bzl)-Met-Asn-Asn-Phe-Gln-Gly-OPac (6.0 g) (SEQ ID NO: 17) was dissolved in dimethyl sulfoxide. An aqueous ammonium formate solution (10 mmol/L) (15.6 mL), acetic acid (18.7 mL) and zinc powder (10.2 g) were added to the obtained solution at 30° C. After 1 hour, the zinc powder was filtered off from the reaction solution, and the filtrate was washed with dimethyl sulfoxide. Water was added to the reaction solution. The deposited precipitate was collected by filtration and washed with water, acetonitrile and diethyl ether. These procedures yielded 5.5 g of the product of interest.

[1-2: Synthesis of Segment 2]

Boc-Phe-Gly-OPac

Boc-Gly-OPac (44 g) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (33 mL) was added to the residue. Diethyl ether was added to the obtained mixture. The deposited precipitate was collected by filtration and washed with diethyl ether. The obtained hydrochloride salt was dissolved in methylene chloride. Boc-Phe-OH (36.6 g) was added to the obtained solution. 1-Ethyl-3-(3-dimethylaminopropyl)carbodiimide (27.5 mL) was added dropwise to the mixture under cooling. The reaction solution was stirred overnight at room temperature. The reaction solution was washed with a 0.5 N aqueous hydrochloric acid solution and saturated saline. The organic layer was dried over $MgSO_4$, and then the methylene chloride was distilled off under reduced pressure. Diethyl ether was added to the residue. The deposited precipitate was collected by filtration and washed with diethyl ether. The obtained crystals were dissolved in chloroform. The solvent was distilled off under reduced pressure. Diethyl ether was added to the residue. The deposited precipitate was collected by filtration and washed with diethyl ether. These procedures yielded 38 g of the product of interest.

Boc-Ser(Bzl)-Phe-Gly-OPac

Boc-Phe-Gly-OPac (8.8 g) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (4.5 mL) was added to the residue. Diethyl ether was added to the obtained mixture. The deposited precipitate was collected by filtration and washed with diethyl ether. The obtained hydrochloride salt was dissolved in N,N-dimethylformamide. Boc-Ser(Bzl)-OH (6.2 g) and 1-hydroxybenzotriazole (2.8 g) were added to the obtained solution. 1-Ethyl-3-(3-dimethylaminopropyl)carbodiimide (3.8 mL) was added dropwise to the mixture under cooling. The reaction solution was stirred overnight at room temperature. Water was added to the reaction solution. The deposited precipitate was collected by filtration and washed with water. The obtained crystals were dissolved in a chloroform/methanol mixed solution. The solvent was distilled off under reduced pressure. Diethyl ether was added to the residue. The deposited precipitate was collected by filtration and washed with diethyl ether. These procedures yielded 11.5 g of the product of interest.

Boc-Arg(Tos)-Ser(Bzl)-Phe-Gly-OPac (SEQ ID NO: 19)

Boc-Ser(Bzl)-Phe-Gly-OPac (11.4 g) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (4.8 mL) was added to the residue. Diethyl ether was added to the obtained mixture. The deposited precipitate was collected by filtration and washed with diethyl ether. The obtained hydrochloride salt was dissolved in N,N-dimethylformamide. Boc-Arg(Tos)-OH (10 g) and 1-hydroxybenzotriazole (2.8 g) were added to the obtained solution. 1-Ethyl-3-(3-dimethylaminopropyl)carbodiimide (4 mL) was added dropwise to the mixture under cooling. The reaction solution was stirred overnight at room temperature. The reaction solution was diluted with ethyl acetate and washed with a 5% aqueous sodium bicarbonate solution, a 0.5 N aqueous hydrochloric acid solution and saturated saline. The organic layer was dried over $MgSO_4$, and then the ethyl acetate was distilled off under reduced pressure. Diethyl ether was added to the residue. The deposited precipitate was collected by filtration and washed with diethyl ether. The obtained crystals were dissolved in ethyl acetate. The solvent was distilled off under reduced pressure. Diethyl ether was added to the residue. The deposited precipitate was collected by filtration and washed with diethyl ether. These procedures yielded 15.8 g of the product of interest.

Boc-Leu-Arg(Tos)-Ser(Bzl)-Phe-Gly-OPac (SEQ ID NO: 20)

Boc-Arg(Tos)-Ser(Bzl)-Phe-Gly-OPac (15.7 g) (SEQ ID NO: 19) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (4 mL) was added to the residue. Diethyl ether was added to the obtained mixture. The deposited precipitate was collected by filtration and washed with diethyl ether. The obtained hydrochloride salt was dissolved in N,N-dimethylformamide. Boc-Leu-OH—$H_2O$ (4.6 g) and 1-hydroxybenzotriazole (2.6 g) were added to the obtained solution. 1-Ethyl-3-(3-dimethylaminopropyl)carbodiimide (3.6 mL) was added dropwise to the mixture under cooling. The reaction solution was stirred at room temperature for 4 hours. Water was added to the reaction solution. The deposited precipitate was collected by filtration and washed with water. The obtained crystals were dissolved in a chloroform/methanol mixed solution. The solvent was distilled off under reduced pressure. Diethyl ether was added to the residue. The deposited precipitate was collected by filtration and washed with diethyl ether. These procedures yielded 17.6 g of the product of interest.

Boc-Leu-Arg(Tos)-Ser(Bzl)-Phe-Gly-OH (SEQ ID NO: 20)

Boc-Leu-Arg(Tos)-Ser(Bzl)-Phe-Gly-OPac (17.6 g) (SEQ ID NO: 20) was dissolved in acetic acid. Zinc powder (55.2 g) was added to the obtained solution at 40° C. After 2 hours, the zinc powder was filtered off from the reaction solution, and the filtrate was washed with acetic acid. The acetic acid was distilled off under reduced pressure, and then the residue was diluted with ethyl acetate. The obtained solution was washed with a 0.1 N aqueous hydrochloric acid solution and saturated saline. The organic layer was dried over $MgSO_4$, and then the ethyl acetate was distilled off under reduced pressure. Diethyl ether was added to the residue. The deposited precipitate was collected by filtration and washed with diethyl ether. The obtained crystals were dissolved in chloroform. The solvent was distilled off under reduced pressure. Diethyl ether was added to the residue. The deposited precipitate was collected by filtration and washed with diethyl ether. These procedures yielded 13.9 g of the product of interest.

Boc-Arg(Tos)-Phe-Gly-OPac

Boc-Phe-Gly-OPac (8.8 g) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (4.0 mL) was added to the residue. Diethyl ether was added to the obtained mixture. The deposited precipitate was collected by filtration and washed with diethyl ether. The obtained hydrochloride salt was dissolved in N,N-dimethylformamide. Boc-Arg(Tos)-OH (10.3 g) and 1-hydroxybenzotriazole (2.8 g) were added to the obtained solution. 1-Ethyl-3-(3-dimethylaminopropyl)carbodiimide (3.8 mL) was added dropwise to the mixture under cooling. The reaction solution was stirred overnight at room temperature. The solution was diluted with ethyl acetate. The obtained solution was washed with a 5% aqueous sodium bicarbonate solution, a 0.5 N aqueous hydrochloric acid solution and saturated saline. The organic layer was dried over $MgSO_4$, and then the ethyl acetate was distilled off under reduced pressure. Diethyl ether was added to the residue. The deposited precipitate was collected by filtration and washed with diethyl ether. The obtained crystals were dissolved in ethyl acetate. The solvent was distilled off under reduced pressure. Diethyl ether was added to the residue. The deposited precipitate was collected by filtration and washed with diethyl ether. These procedures yielded 14.7 g of the product of interest.

Boc-Cys(4-MeBzl)-Arg(Tos)-Phe-Gly-OPac (SEQ ID NO: 21)

Boc-Arg(Tos)-Phe-Gly-OPac (14.5 g) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (3.9 mL) was added to the residue. Diethyl ether was added to the obtained mixture. The deposited precipitate was collected by filtration and washed with diethyl ether. The obtained hydrochloride salt was dissolved in N,N-dimethylformamide. Boc-Cys(4-MeBzl)-OH (6.9 g) and 1-hydroxybenzotriazole (2.8 g) were added to the obtained solution. 1-Ethyl-3-(3-dimethylaminopropyl)carbodiimide (3.8 mL) was added dropwise to the mixture under cooling. The reaction solution was stirred at room temperature for 3 hours. Water was added to the reaction solution. The deposited precipitate was collected by filtration and washed with water and n-hexane. The obtained crystals were dissolved in a chloroform/methanol mixed solution. The solvent was distilled off under reduced pressure. Diethyl ether was added to the residue. The deposited precipitate was collected by filtration and washed with diethyl ether. These procedures yielded 17.2 g of the product of interest.

Boc-Leu-Arg(Tos)-Ser(Bzl)-Phe-Gly-Cys(4-MeBzl)-Arg(Tos)-Phe-Gly-OPac (SEQ ID NO: 22)

Boc-Cys(4-MeBzl)-Arg(Tos)-Phe-Gly-OPac (9.1 g) (SEQ ID NO: 21) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (1.9 mL) was added to the residue. Diethyl ether was added to the obtained mixture. The deposited precipitate was collected by filtration and washed with diethyl ether. The obtained hydrochloride salt was dissolved in N,N-dimethylformamide. Boc-Leu-Arg(Tos)-Ser(Bzl)-Phe-Gly-OH (9.2 g) (SEQ ID NO:20) and 1-hydroxybenzotriazole (1.4 g) were added to the obtained solution. 1-Ethyl-3-(3-dimethylaminopropyl)carbodiimide (1.8 mL) was added dropwise to the mixture under cooling. The reaction solution was stirred overnight at room temperature. Water was added to the reaction solution. The deposited precipitate was collected by filtration and washed with water and diethyl ether. The obtained crystals were dissolved in N,N-dimethylformamide. The solvent was distilled off under reduced pressure. Acetonitrile was added to the residue. The deposited precipitate was collected by filtration and washed with acetonitrile and diethyl ether. These procedures yielded 16.2 g of the product of interest.

Boc-Leu-Arg(Tos)-Ser(Bzl)-Phe-Gly-Cys(4-MeBzl)-Arg(Tos)-Phe-Gly-OH (Segment 2) (SEQ ID NO: 22)

Boc-Leu-Arg(Tos)-Ser(Bzl)-Phe-Gly-Cys(4-MeBzl)-Arg(Tos)-Phe-Gly-OPac (7.1 g) (SEQ ID NO: 22) was dissolved in a 1-methyl-2-pyrrolidone/N,N-dimethylformamide mixed solution. An aqueous ammonium formate solution (10 mmol/L) (12 mL), acetic acid (7.2 mL) and zinc powder (7.8 g) were added to the obtained solution at 40° C. After 1 hour, the zinc powder was filtered off from the reaction solution, and the filtrate was washed with N,N-dimethylformamide. The N,N-dimethylformamide was distilled off under reduced pressure, and water was added to the residue. The deposited precipitate was collected by filtration and washed with water and diethyl ether. The obtained crystals were dissolved in N,N-dimethylformamide. The solvent was distilled off under reduced pressure. Diethyl ether was added to the residue. The deposited precipitate was collected by filtration and washed with diethyl ether. These procedures yielded 6 g of the product of interest.

[1-3: Synthesis of Segment 3]

Boc-Leu-Ala-OPac

Boc-Ala-OPac (33.8 g) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (25 mL) was added to the residue. Diethyl ether was added to the obtained mixture. The deposited precipitate was collected by filtration and washed with diethyl ether. The obtained hydrochloride salt was dissolved in methylene chloride. Boc-Leu-OH—$H_2O$ (24.9 g) was added to the obtained solution. 1-Ethyl-3-(3- dimethylaminopropyl)carbodiimide (19.2 mL) was added dropwise to the mixture under cooling. The reaction solution was stirred at room temperature for 3 hours. The reaction solution was washed with a 0.5 N aqueous hydrochloric acid solution and saturated saline. The methylene chloride was distilled off under reduced pressure, and diethyl ether was added to the residue. The deposited precipitate was collected by filtration and washed with diethyl ether. The obtained crystals were dissolved in chloroform. The solvent was distilled off under reduced pressure. Diethyl ether was added to the residue. The deposited precipitate was collected by filtration and washed with diethyl ether. These procedures yielded 30.1 g of the product of interest.

Boc-Lys(ClZ)-Leu-Ala-OPac

Boc-Leu-Ala-OPac (29.4 g) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (16.5 mL) was added to the residue. Diisopropyl ether was added to the obtained mixture. The deposited precipitate was collected by filtration and washed with diisopropyl ether. The obtained hydrochloride salt was dissolved in N,N-dimethylformamide. Boc-Lys(ClZ)-OH (30.5 g) and 1-hydroxybenzotriazole (10.2 g) were added to the obtained solution. 1-Ethyl-3-(3-dimethylaminopropyl)carbodiimide (13.8 mL) was added dropwise to the mixture under cooling. The reaction solution was stirred at room temperature for 3 hours. The solution was diluted with ethyl acetate. This solution was washed with a 0.5 N aqueous hydrochloric acid solution and saturated saline. The ethyl acetate was distilled off under reduced pressure, and diethyl ether was added to the residue. The deposited precipitate was collected by filtration and washed with diethyl ether. The obtained crystals were dissolved in a chloroform/methanol mixed solution. The solvent was distilled off under reduced pressure. Diethyl ether was added to the residue. The deposited precipitate was collected by filtration and washed with diethyl ether. These procedures yielded 47.5 g of the product of interest.

Boc-Gln-Lys(ClZ)-Leu-Ala-OPac (SEQ ID NO: 23)

Boc-Lys(ClZ)-Leu-Ala-OPac (47.3 g) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (15.6 mL) was added to the residue. Diethyl ether was added to the obtained mixture. The deposited precipitate was collected by filtration and washed with diethyl ether. The obtained hydrochloride salt was dissolved in N,N-dimethylformamide. Boc-Gln-OH (17.6 g) and 1-hydroxybenzotriazole (9.8 g) were added to the obtained solution. 1-Ethyl-3-(3-dimethylaminopropyl)carbodiimide (13.3 mL) was added dropwise to the mixture under cooling. The reaction solution was stirred at room temperature for 4 hours. Water was added to the reaction solution. The deposited precipitate was collected by filtration and washed with water, methanol and diethyl ether. These procedures yielded 54.5 g of the product of interest.

Boc-Val-Gln-Lys(ClZ)-Leu-Ala-OPac (SEQ ID NO: 24)

Boc-Gln-Lys(ClZ)-Leu-Ala-OPac (54.1 g) (SEQ ID NO: 23) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (15 mL) was added to the residue. Diethyl ether was added to the obtained mixture. The deposited precipitate was collected by filtration and washed with diethyl ether. The obtained hydrochloride salt was dissolved in N,N-dimethylformamide. Boc-Val-OH (14.6 g) and 1-hydroxybenzotriazole (9.1 g) were added to the obtained solution. 1-Ethyl-3-(3-dimethylaminopropyl)carbodiimide (13.3 mL) was added dropwise to the mixture under cooling. The reaction solution was stirred at room temperature for 4 hours. Water was added to the reaction solution. The deposited precipitate was collected by filtration and washed with water, methanol and diethyl ether. These procedures yielded 59.2 g of the product of interest.

Boc-Thr(Bzl)-Val-Gln-Lys(ClZ)-Leu-Ala-OPac (SEQ ID NO: 25)

Boc-Val-Gln-Lys(ClZ)-Leu-Ala-OPac (58.6 g) (SEQ ID NO: 24) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (15 mL) was added to the residue. Diethyl ether was added to the obtained mixture. The deposited precipitate was collected by filtration and washed with diethyl ether. The obtained hydrochloride salt was dissolved in N,N-dimethylformamide. Boc-Thr(Bzl)-OH (14.6 g) and 1-hydroxybenzotriazole (8.8 g) were added to the obtained solution. 1-Ethyl-3-(3-dimethylaminopropyl)carbodiimide (11.9 mL) was added dropwise to the mixture under cooling. The reaction solution was stirred at room temperature for 4 hours. Water was added to the reaction solution. The deposited precipitate was collected by filtration and washed with water, methanol, diethyl ether, acetonitrile and diethyl ether. These procedures yielded 70.2 g of the product of interest.

Boc-Cys(4-MeBzl)-Thr(Bzl)-Val-Gln-Lys(ClZ)-Leu-Ala-OPac (SEQ ID NO: 26)

Boc-Thr(Bzl)-Val-Gln-Lys(ClZ)-Leu-Ala-OPac (34.1 g) (SEQ ID NO: 25) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (7.1 mL) was added to the residue. Diethyl ether was added to the obtained mixture. The deposited precipitate was collected by filtration and washed with diethyl ether. The obtained hydrochloride salt was dissolved in 1-methyl-2-pyrrolidone. Boc-Cys(4-MeBzl)-OH (10.5 g) and 1-hydroxybenzotriazole (4.5 g) were added to the obtained solution. 1-Ethyl-3-(3-dimethylaminopropyl)carbodiimide (6.0 mL) was added dropwise to the mixture under cooling. The reaction solution was stirred at room temperature for 4 hours. Water was added to the reaction solution. The deposited precipitate was collected by filtration and washed with water, methanol, diethyl ether, acetonitrile and diethyl ether. These procedures yielded 38.4 g of the product of interest.

Boc-Thr(Bzl)-Cys(4-MeBzl)-Thr(Bzl)-Val-Gln-Lys(ClZ)-Leu-Ala-OPac (SEQ ID NO: 27)

Boc-Cys(4-MeBzl)-Thr(Bzl)-Val-Gln-Lys(ClZ)-Leu-Ala-OPac (37.6 g) (SEQ ID NO: 26) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (6.5 mL) was added to the residue. Diethyl ether was added to the obtained mixture. The deposited precipitate was collected by filtration and washed with diethyl ether. The obtained hydrochloride salt was dissolved in a dimethyl sulfoxide/1-methyl-2-pyrrolidone/1,3-dimethyl-2-imidazolidinone mixed solution. Boc-Thr(Bzl)-OH (9.3 g) and 1-hydroxybenzotriazole (4.2 g) were added to the obtained solution. 1-Ethyl-3-(3-dimethylaminopropyl)carbodiimide (5.6 mL) was added dropwise to the mixture under cooling. The reaction solution was stirred at room temperature for 4 hours. Water was added to the reaction solution. The deposited precipitate was collected by filtration and washed with water, methanol, diethyl ether, acetonitrile and diethyl ether. The residue was dissolved in a chloroform/2,2,2-trifluoroethanol mixed solution. The solvent was distilled off under reduced pressure. Diethyl ether was added to the residue. The deposited precipitate was collected by filtration and washed with diethyl ether. These procedures yielded 42.0 g of the product of interest.

Boc-Thr(Bzl)-Cys(4-MeBzl)-Thr(Bzl)-Val-Gln-Lys(ClZ)-Leu-Ala-OH (Segment 3) (SEQ ID NO: 27)

Boc-Thr(Bzl)-Cys(4-MeBzl)-Thr(Bzl)-Val-Gln-Lys (ClZ)-Leu-Ala-OPac (15.3 g) (SEQ ID NO: 27) was dissolved in a methylene chloride/2,2,2-trifluoroethanol mixed solution. An aqueous ammonium formate solution (10 mmol/L) (10 mL), acetic acid (6 mL) and zinc powder (32 g) were added to the obtained solution at 30° C. After 30 minutes, the zinc powder was filtered off from the reaction solution, and the filtrate was washed with a methylene chloride/2,2,2-trifluoroethanol mixed solution. The solvent was distilled off under reduced pressure, and an aqueous hydrochloric acid solution was added to the residue. The deposited precipitate was collected by filtration and washed with water and diethyl ether. The obtained crystals were dissolved in N,N-dimethylformamide. The solvent was distilled off under reduced pressure. Diethyl ether was added to the residue. The deposited precipitate was collected by filtration and washed with diethyl ether. These procedures yielded 14.1 g of the product of interest.

[1-4: Synthesis of Segment 4]

Boc-Tyr(BrZ)-Gln-OPac

Boc-Gln-OPac (36.5 g) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (20 mL) was added to the residue. Diethyl ether was added to the obtained mixture. The deposited precipitate was collected by filtration and washed with diethyl ether. The obtained hydrochloride salt was added to N,N-dimethylformamide. Boc-Tyr(BrZ)-OH (54 g) and 1-hydroxybenzotriazole (14.8 g) were added to the obtained mixture. 1-Ethyl-3-(3-dimethylaminopropyl) carbodiimide (20 mL) was added dropwise to the mixture under cooling. The reaction solution was stirred overnight at room temperature. The reaction solution was diluted with ethyl acetate. This solution was washed with a 5% aqueous sodium bicarbonate solution, a 0.5 N aqueous hydrochloric acid solution and saturated saline. The organic layer was dried over $MgSO_4$, and then the ethyl acetate was distilled off under reduced pressure. Diethyl ether was added to the residue. The deposited precipitate was collected by filtration and washed with diethyl ether. The obtained crystals were added to an ethyl acetate/methanol mixed solution. The solvent was distilled off under reduced pressure. Diethyl ether was added to the residue. The deposited precipitate was collected by filtration and washed with diethyl ether. These procedures yielded 29.8 g of the product of interest.

Boc-Ile-Tyr(BrZ)-Gln-OPac

Boc-Tyr(BrZ)-Gln-OPac (29 g) was dissolved in trifluoroacetic acid. The obtained solution was stirred for 10 minutes under cooling and then at room temperature for 50 minutes.

The trifluoroacetic acid was distilled off under reduced pressure from the reaction solution, and a solution of hydrogen chloride in dioxane (5.5 mol/L) (9 mL) was added to the residue. Diethyl ether was added to the obtained mixture. The deposited precipitate was collected by filtration and washed with diethyl ether. The obtained hydrochloride salt was added to N,N-dimethylformamide. Boc-Ile-OH-1/$2.H_2O$ (10.5 g) and 1-hydroxybenzotriazole (5.9 g) were added to the mixture. 1-Ethyl-3-(3-dimethylaminopropyl) carbodiimide (8 mL) was added dropwise to the mixture under cooling. The reaction solution was stirred overnight at room temperature. Acetonitrile was added to the reaction solution. The deposited precipitate was collected by filtration and washed with acetonitrile and diethyl ether. These procedures yielded 32.0 g of the product of interest.

Boc-Gln-Ile-Tyr(BrZ)-Gln-OPac (SEQ ID NO: 28)

Boc-Ile-Tyr(BrZ)-Gln-OPac (25.5 g) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (7 mL) was added to the residue. Diethyl ether was added to the obtained mixture. The deposited precipitate was collected by filtration and washed with diethyl ether. The obtained hydrochloride salt was added to N,N-dimethylformamide. Boc-Gln-OH (7.7 g) and 1-hydroxybenzotriazole (4.5 g) were added to the obtained solution. 1-Ethyl-3-(3-dimethylaminopropyl)carbodiimide (6 mL) was added dropwise to the mixture under cooling. The reaction solution was stirred overnight at room temperature. Acetonitrile was added to the reaction solution. The deposited precipitate was collected by filtration and washed with acetonitrile and diethyl ether. These procedures yielded 27.3 g of the product of interest.

Boc-His-Gln-Ile-Tyr(BrZ)-Gln-OPac (SEQ ID NO: 29)

Boc-Gln-Ile-Tyr(BrZ)-Gln-OPac (19.6 g) (SEQ ID NO: 28) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (5 mL) was added to the residue. Diethyl ether was added to the obtained mixture. The deposited precipitate was collected by filtration and washed with diethyl ether. The obtained hydrochloride salt was added to N,N-dimethylformamide. Boc-His(Tos)-OH (9.0 g) and 1-hydroxybenzotriazole (3.0 g) were added to the obtained solution. 1-Ethyl-3-(3-dimethylaminopropyl)carbodiimide (4 mL) was added dropwise to the mixture under cooling. The reaction solution was stirred overnight at room temperature. Acetonitrile was added to the reaction solution. The deposited precipitate was collected by filtration and washed with acetonitrile and diethyl ether. These procedures yielded 18.3 g of the product of interest.

Boc-His-Gln-Ile-Tyr(BrZ)-Gln-OH (segment 4) (SEQ ID NO: 29)

Boc-His-Gln-Ile-Tyr(BrZ)-Gly-OPac (15.0 g) (SEQ ID NO: 29) was dissolved in a methylene chloride/2,2,2-trifluoroethanol/acetic acid mixed solution. Zinc powder (43.9 g) was added to the obtained solution at 40° C. After 30 minutes, the zinc powder was filtered off from the reaction solution, and the filtrate was washed with a methylene chloride/2,2,2-trifluoroethanol mixed solution. The solvent was distilled off under reduced pressure, and water was added to the residue. The deposited precipitate was collected by filtration and washed with water, an aqueous hydrochloric acid solution, water, diethyl ether, acetonitrile and diethyl ether. The obtained crystals were dissolved in N,N-dimethylformamide. The solvent was distilled off under reduced pressure. Diethyl ether was added to the residue. The deposited precipitate was collected by filtration and washed with diethyl ether. These procedures yielded 9.5 g of the product of interest.

[1-5: Synthesis of segment 5]

Boc-Ala-Pro-OPac

Boc-Ala-OH (95 g), Pro-OBzl.HCl (127 g) and 1-hydroxybenzotriazole (7 g) were added to methylene chloride. 1-Ethyl-3-(3-dimethylaminopropyl)carbodiimide (96 mL) was added dropwise to the obtained solution under cooling. The reaction solution was stirred overnight at room temperature. The methylene chloride was distilled off under reduced pressure, and the residue was diluted with ethyl acetate. The organic layer was washed with a 5% aqueous sodium bicarbonate solution, a 0.5 N aqueous hydrochloric acid solution and saturated saline. The ethyl acetate was distilled off under reduced pressure, and n-hexane was added to the residue. The deposited precipitate was collected by filtration and washed with n-hexane. These procedures yielded 158 g of crystals. 27.1 g of the crystals was dissolved in methanol. 5% Pd—C(5 g) was added to the obtained solution. Hydrogen gas was added to the reaction solution. After the completion of the reaction, the 5% Pd—C was filtered off. The methanol was distilled off under reduced pressure. Diethyl ether was added to the residue. The deposited precipitate was collected by filtration and washed with diethyl ether. These procedures yielded 19.7 g of crystals. 19.7 g of the crystals was dissolved in N,N-dimethylformamide. Phenacyl bromide (14.4 g) and triethylamine (10.1 mL) were added to the obtained solution. The reaction solution was stirred for 1 hour. The reaction solution was diluted with ethyl acetate. The obtained solution was washed with a 5% aqueous sodium bicarbonate solution, a 0.5 N aqueous hydrochloric acid solution and saturated saline. The organic layer was dried over $MgSO_4$, and then the ethyl acetate was distilled off under reduced pressure. n-Hexane was added to the residue. The deposited precipitate was collected by filtration and washed with n-hexane. These procedures yielded 25.2 g of the product of interest.

Boc-Val-Ala-Pro-OPac

Boc-Ala-Pro-OPac (25.8 g) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (14.7 mL) was added to the residue. Diethyl ether was added to the obtained mixture. The deposited precipitate was collected by filtration and washed with diethyl ether. The obtained hydrochloride salt was added to N,N-dimethylformamide. Boc-Val-OH (14.5 g) and 1-hydroxybenzotriazole (9.5 g) were added to the obtained solution. 1-Ethyl-3-(3-dimethylaminopropyl)carbodiimide (12.8 mL) was added dropwise to the mixture under cooling. The reaction solution was stirred overnight at room temperature. The reaction solution was diluted with ethyl acetate. The obtained solution was washed with a 5% aqueous sodium bicarbonate solution, a 0.5 N aqueous hydrochloric acid solution and saturated saline. The organic layer was dried over $MgSO_4$, and then the ethyl acetate was distilled off under reduced pressure. n-Hexane was added to the residue. The deposited precipitate was collected by filtration and washed with n-hexane. The obtained crystals were dissolved in ethyl acetate. The solvent was distilled off under reduced pressure. Diethyl ether was added to the residue. The deposited precipitate was collected by filtration and washed with diethyl ether. These procedures yielded 24.4 g of the product of interest.

Boc-Asn-Val-Ala-Pro-OPac (SEQ ID NO: 30)

Boc-Val-Ala-Pro-OPac (24.4 g) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (11.2 mL) was added to the residue. Diethyl ether was added to the obtained mixture. The deposited precipitate was collected by filtration and washed with diethyl ether. The obtained hydrochloride salt was added to N,N-dimethylformamide. Boc-Asn-OH (11.8 g) and 1-hydroxybenzotriazole (7.2 g) were added to the obtained solution. 1-Ethyl-3-(3-dimethylaminopropyl)carbodiimide (9.8 mL) was added dropwise to the mixture under cooling. The reaction solution was stirred overnight at room temperature. The reaction solution was diluted with ethyl acetate. The obtained solution was washed with a 5% aqueous sodium bicarbonate solution, a 0.5 N aqueous hydrochloric acid solution and saturated saline. The organic layer was dried over $MgSO_4$, and then the ethyl acetate was distilled off under reduced pressure. Diethyl ether was added to the residue. The deposited precipitate was collected by filtration and washed with diethyl ether. The obtained crystals were dissolved in chloroform. The solvent was distilled off under reduced pressure. Diethyl ether was added to the residue. The deposited precipitate was collected by filtration and washed with diethyl ether. These procedures yielded 26.5 g of the product of interest.

Boc-Asp(OcHex)-Asn-Val-Ala-Pro-OPac (SEQ ID NO: 31)

Boc-Asn-Val-Ala-Pro-OPac (26.5 g) (SEQ ID NO: 30) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (10 mL) was added to the residue. Diethyl ether was added to the obtained mixture. The deposited precipitate was collected by filtration and washed with diethyl ether. The obtained hydrochloride salt was added to N,N-dimethylformamide. Boc-Asp(OcHex)-OH (14.2 g) and 1-hydroxybenzotriazole (6.4 g) were added to the obtained solution. 1-Ethyl-3-(3-dimethylaminopropyl)carbodiimide (8.6 mL) was added dropwise to the mixture under cooling. The reaction solution was stirred overnight at room temperature. The reaction solution was diluted with ethyl acetate. The obtained solution was washed with a 5% aqueous sodium bicarbonate solution, a 0.5 N aqueous hydrochloric acid solution and saturated saline. The organic layer was dried over $MgSO_4$, and then the ethyl acetate was distilled off under reduced pressure. Diethyl ether was added to the residue. The deposited precipitate was collected by filtration and washed with diethyl ether. These procedures yielded 33.8 g of the product of interest.

Boc-Lys(ClZ)-Asp(OcHex)-Asn-Val-Ala-Pro-OPac (SEQ ID NO: 32)

Boc-Asp(OcHex)-Asn-Val-Ala-Pro-OPac (33.8 g) (SEQ ID NO: 31) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (9.6 mL) was added to the residue. Diethyl ether was added to the obtained mixture. The deposited precipitate was collected by filtration and washed with diethyl ether. The obtained hydrochloride salt was added to N,N-dimethylformamide. Boc-Lys(ClZ)-OH (18.0 g) and 1-hydroxybenzotriazole (6.2 g) were added to the obtained solution. 1-Ethyl-3-(3-dimethylaminopropyl)carbodiimide (8.4 mL) was added dropwise to the mixture under cooling. The reaction solution was stirred overnight at room temperature. The reaction solution was diluted with ethyl acetate. The obtained solution was washed with a 5% aqueous sodium bicarbonate solution, a 0.5 N aqueous hydrochloric acid solution and saturated saline. The organic layer was dried over $MgSO_4$, and then the ethyl acetate was distilled off under reduced pressure. Diethyl ether was added to the residue. The deposited precipitate was collected by filtration and washed with diethyl ether. The obtained crystals were dissolved in chloroform. The solvent was distilled off under reduced pressure. Diethyl ether was added to the residue. The deposited precipitate was collected by filtration and washed with diethyl ether. These procedures yielded 46.0 g of the product of interest.
Boc-Asp(OcHex)-Lys(ClZ)-Asp(OcHex)-Asn-Val-Ala-Pro-OPac (SEQ ID NO: 33)

Boc-Lys(ClZ)-Asp(OcHex)-Asn-Val-Ala-Pro-OPac (45.8 g) (SEQ ID NO: 32) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (9.5 mL) was added to the residue. Diethyl ether was added to the obtained mixture. The deposited precipitate was collected by filtration and washed with diethyl ether. The obtained hydrochloride salt was dissolved in a 1-methyl-2-pyrrolidone/N,N-dimethylformamide mixed solution. Boc-Asp(OcHex)-OH (12.2 g) and 1-hydroxybenzotriazole (5.5 g) were added to the obtained solution. 1-Ethyl-3-(3-dimethylaminopropyl)carbodiimide (7.4 mL) was added dropwise to the mixture under cooling. The reaction solution was stirred overnight at room temperature. Water was added to the reaction solution. The deposited precipitate was collected by filtration and washed with water. The residue was dissolved in chloroform, and the solvent was distilled off under reduced pressure. Diethyl ether was added to the residue. The deposited precipitate was collected by filtration and washed with diethyl ether. These procedures yielded 50.3 g of the product of interest.
Boc-Lys(ClZ)-Asp(OcHex)-Lys(ClZ)-Asp(OcHex)-Asn-Val-Ala-Pro-OPac (SEQ ID NO: 34)

Boc-Asp(OcHex)-Lys(ClZ)-Asp(OcHex)-Asn-Val-Ala-Pro-OPac (23.6 g) (SEQ ID NO: 33) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (4.2 mL) was added to the residue. Diethyl ether was added to the obtained mixture. The deposited precipitate was collected by filtration and washed with diethyl ether. The obtained hydrochloride salt was dissolved in a 1-methyl-2-pyrrolidone/N,N-dimethylformamide mixed solution. Boc-Lys(ClZ)-OH (7.4 g) and 1-hydroxybenzotriazole (2.5 g) were added to the obtained solution. 1-Ethyl-3-(3-dimethylaminopropyl)carbodiimide (3.4 mL) was added dropwise to the mixture under cooling. The reaction solution was stirred at room temperature. Water was added to the reaction solution. The deposited precipitate was collected by filtration and washed with water and diethyl ether. The residue was dissolved in a chloroform/methanol mixed solution, and the solvent was distilled off under reduced pressure. Diethyl ether was added to the residue. The deposited precipitate was collected by filtration and washed with diethyl ether. These procedures yielded 24.2 g of the product of interest.
Boc-Asp(OcHex)-Lys(ClZ)-Asp(OcHex)-Lys(ClZ)-Asp (OcHex)-Asn-Val-Ala-Pro-OPac (SEQ ID NO: 35)

Boc-Lys(ClZ)-Asp(OcHex)-Lys(ClZ)-Asp(OcHex)-Asn-Val-Ala-Pro-OPac (24.0 g) (SEQ ID NO: 34) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (3.4 mL) was added to the residue. Diethyl ether was added to the obtained mixture. The deposited precipitate was collected by filtration and washed with diethyl ether. The obtained hydrochloride salt was dissolved in a 1-methyl-2-pyrrolidone/N,N-dimethylformamide mixed solution. Boc-Asp(OcHex)-OH (4.9 g) and 1-hydroxybenzotriazole (2.2 g) were added to the obtained solution. 1-Ethyl-3-(3-dimethylaminopropyl)carbodiimide (3.0 mL) was added dropwise to the mixture under cooling. The reaction solution was stirred overnight at room temperature. Water was added to the reaction solution. The deposited precipitate was collected by filtration and washed with water and diethyl ether. The residue was dissolved in a chloroform/2,2,2-trifluoroethanol mixed solution, and the solvent was distilled off under reduced pressure. Diethyl ether was added to the residue. The deposited precipitate was collected by filtration and washed with diethyl ether. These procedures yielded 27.1 g of the product of interest.
Boc-Thr(Bzl)-Asp(OcHex)-Lys(ClZ)-Asp(OcHex)-Lys (ClZ)-Asp(OcHex)-Asn-Val-Ala-Pro-OPac (SEQ ID NO: 36)

Boc-Asp(OcHex)-Lys(ClZ)-Asp(OcHex)-Lys(ClZ)-Asp (OcHex)-Asn-Val-Ala-Pro-OPac (27.1 g) (SEQ ID NO: 35) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (3.4 mL) was added to the residue. Diethyl ether was added to the obtained mixture. The deposited precipitate was collected by filtration and washed with diethyl ether. The obtained hydrochloride salt was dissolved in a 1-methyl-2-pyrrolidone/N,N-dimethylformamide mixed solution. Boc-Thr(Bzl)-OH (4.6 g) and 1-hydroxybenzotriazole (2.1 g) were added to the obtained solution. 1-Ethyl-3-(3-dimethylaminopropyl)carbodiimide (2.9 mL) was added dropwise to the mixture under cooling. The reaction solution was stirred overnight at room temperature. Water was added to the reaction solution. The deposited precipitate was collected by filtration and washed with water and diethyl ether. The residue was dissolved in a chloroform/2,2,2-trifluoroethanol mixed solution, and the solvent was distilled off under reduced pressure. Diethyl ether was added to the residue. The deposited precipitate was collected by filtration and washed with diethyl ether. These procedures yielded 26.0 g of the product of interest.
Boc-Phe-Thr(Bzl)-Asp(OcHex)-Lys(ClZ)-Asp(OcHex)-Lys (ClZ)-Asp(OcHex)-Asn-Val-Ala-Pro-OPac (SEQ ID NO: 37)

Boc-Thr(Bzl)-Asp(OcHex)-Lys(ClZ)-Asp(OcHex)-Lys (ClZ)-Asp(OcHex)-Asn-Val-Ala-Pro-OPac (24.0 g) (SEQ

ID NO: 36) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (2.8 mL) was added to the residue. Diethyl ether was added to the obtained mixture. The deposited precipitate was collected by filtration and washed with diethyl ether. The obtained hydrochloride salt was dissolved in a 1-methyl-2-pyrrolidone/N,N-dimethylformamide mixed solution. Boc-Phe-OH (3.4 g) and 1-hydroxybenzotriazole (1.8 g) were added to the obtained solution. 1-Ethyl-3-(3-dimethylaminopropyl)carbodiimide (2.4 mL) was added dropwise to the mixture under cooling. The reaction solution was stirred overnight at room temperature. Water was added to the reaction solution. The deposited precipitate was collected by filtration and washed with water and diethyl ether. The residue was dissolved in a N,N-dimethylformamide mixed solution. Acetonitrile was added to the obtained solution. The deposited precipitate was collected by filtration and washed with diethyl ether. These procedures yielded 24.3 g of the product of interest.

Boc-Phe-Thr(Bzl)-Asp(OcHex)-Lys(ClZ)-Asp(OcHex)-Lys(ClZ)-Asp(OcHex)-Asn-Val-Ala-Pro-OH (segment 5) (SEQ ID NO: 37)

Boc-Phe-Thr(Bzl)-Asp(OcHex)-Lys(ClZ)-Asp(OcHex)-Lys(ClZ)-Asp(OcHex)-Asn-Val-Ala-Pro-OPac (24.3 g) (SEQ ID NO: 37) was dissolved in acetic acid. Zinc powder (36.9 g) was added to the obtained solution at 40° C. After 2 hours, the zinc powder was filtered off from the reaction solution, and the filtrate was washed with acetic acid. The acetic acid was distilled off under reduced pressure, and water was added to the residue. The deposited precipitate was collected by filtration and washed with water and diethyl ether. The residue was added to a N,N-dimethylformamide mixed solution, and acetonitrile was added to the mixture. The deposited precipitate was collected by filtration and washed with diethyl ether. These procedures yielded 21.0 g of the product of interest.

[1-6: Synthesis of Segment 6]
Boc-Gly-Tyr(Br—Z)—NH$_2$

Boc-Tyr(Br—Z)—NH$_2$ (49.3 g) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (21.8 mL) was added to the residue. Diethyl ether was added to the obtained mixture. The deposited precipitate was collected by filtration and washed with diethyl ether. The obtained hydrochloride salt was dissolved in N,N-dimethylformamide. Boc-Gly-OH (18.0 g) and 1-hydroxybenzotriazole (14.9 g) were added to the obtained solution. 1-Ethyl-3-(3-dimethylaminopropyl)carbodiimide (20.1 mL) was added dropwise to the mixture under cooling. The reaction solution was stirred overnight at room temperature. An aqueous sodium bicarbonate solution was added to the reaction solution. The deposited precipitate was collected by filtration and washed with water. The residue was dissolved in a chloroform/methanol mixed solution, and the solvent was distilled off under reduced pressure. Diethyl ether was added to the residue. The deposited precipitate was collected by filtration and washed with diethyl ether. These procedures yielded 55 g of the product of interest.

Boc-Gln-Gly-Tyr(Br—Z)—NH$_2$

Boc-Gly-Tyr(Br—Z)—NH$_2$ (55 g) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (21.8 mL) was added to the residue. Diethyl ether was added to the obtained mixture. The deposited precipitate was collected by filtration and washed with diethyl ether. The obtained hydrochloride salt was dissolved in N,N-dimethylformamide. Boc-Gln-OH (27 g) and 1-hydroxybenzotriazole (14.9 g) were added to the obtained solution. 1-Ethyl-3-(3-dimethylaminopropyl)carbodiimide (20.1 mL) was added dropwise to the mixture under cooling. The reaction solution was stirred overnight at room temperature. An aqueous sodium bicarbonate solution was added to the reaction solution. The deposited precipitate was collected by filtration and washed with water. The residue was dissolved in a chloroform/methanol mixed solution, and the solvent was distilled off under reduced pressure. Diethyl ether was added to the residue. The deposited precipitate was collected by filtration and washed with diethyl ether. These procedures yielded 59 g of the product of interest.

Boc-Pro-Gln-Gly-Tyr(Br—Z)—NH$_2$ (SEQ ID NO: 38)

Boc-Gln-Gly-Tyr(Br—Z)—NH$_2$ (59 g) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (19.0 mL) was added to the residue. Diethyl ether was added to the obtained mixture. The deposited precipitate was collected by filtration and washed with diethyl ether. The obtained hydrochloride salt was dissolved in N,N-dimethylformamide. Boc-Pro-OH (19.3 g) and 1-hydroxybenzotriazole (12.9 g) were added to the obtained solution. 1-Ethyl-3-(3-dimethylaminopropyl)carbodiimide (17.5 mL) was added dropwise to the mixture under cooling. The reaction solution was stirred overnight at room temperature. An aqueous sodium bicarbonate solution was added to the reaction solution. The deposited precipitate was collected by filtration and washed with water. The residue was dissolved in a chloroform/methanol mixed solution, and the solvent was distilled off under reduced pressure. Diethyl ether was added to the residue. The deposited precipitate was collected by filtration and washed with diethyl ether. These procedures yielded 60.6 g of the product of interest.

Boc-Ser(Bzl)-Pro-Gln-Gly-Tyr(Br—Z)—NH$_2$ (SEQ ID NO: 39)

Boc-Pro-Gln-Gly-Tyr(Br—Z)—NH$_2$ (60.6 g) (SEQ ID NO: 38) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (15.4 mL) was added to the residue. Diethyl ether was added to the obtained mixture. The deposited precipitate was collected by filtration and washed with diethyl ether. The obtained hydrochloride salt was dissolved in N,N-dimethylformamide. Boc-Ser(Bzl)-OH (24.3 g) and 1-hydroxybenzotriazole (11.6 g) were added to the obtained solution. 1-Ethyl-3-(3-dimethylaminopropyl)carbodiimide (15.8 mL) was added dropwise to the mixture under cooling. The reaction solution was stirred overnight at room temperature. The N,N-dimethylformamide was distilled off under reduced pressure from the reaction solution. An aqueous sodium bicarbonate solution was added to the residue. The deposited precipitate was collected by filtration and washed with water and diethyl ether. The residue was dissolved in a chloroform/methanol mixed solution, and the solvent was distilled off under reduced pressure. Diethyl ether was added to the residue. The deposited precipitate was collected by filtration and washed with diethyl ether. These procedures yielded 17 g of the product of interest.
Boc-Ile-Ser(Bzl)-Pro-Gln-Gly-Tyr(Br—Z)—NH$_2$ (SEQ ID NO: 40)

Boc-Ser(Bzl)-Pro-Gln-Gly-Tyr(Br—Z)—NH$_2$ (16.7 g) (SEQ ID NO: 39) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (4.2 mL) was added to the residue. Diethyl ether was added to the obtained mixture. The deposited precipitate was collected by filtration and washed with diethyl ether. The obtained hydrochloride salt was dissolved in N,N-dimethylformamide. Boc-Ile-OH-1/2 H$_2$O (4.8 g) and 1-hydroxybenzotriazole (2.9 g) were added to the obtained solution. 1-Ethyl-3-(3-dimethylaminopropyl)carbodiimide (3.9 mL) was added dropwise to the mixture under cooling. The reaction solution was stirred overnight at room temperature. An aqueous sodium bicarbonate solution was added to the reaction solution. The deposited precipitate was collected by filtration and washed with water and diethyl ether. These procedures yielded 17 g of the product of interest.
Boc-Lys(ClZ)-Ile-Ser(Bzl)-Pro-Gln-Gly-Tyr(Br—Z)—NH$_2$ (SEQ ID NO: 41)

Boc-Ile-Ser(Bzl)-Pro-Gln-Gly-Tyr(Br—Z)—NH$_2$ (17.9 g) (SEQ ID NO: 40) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (4.0 mL) was added to the residue. Diethyl ether was added to the obtained mixture. The deposited precipitate was collected by filtration and washed with diethyl ether. The obtained hydrochloride salt was dissolved in N,N-dimethylformamide. Boc-Lys(ClZ)-OH (8.0 g) and 1-hydroxybenzotriazole (2.7 g) were added to the obtained solution. 1-Ethyl-3-(3-dimethylaminopropyl)carbodiimide (3.7 mL) was added dropwise to the mixture under cooling. The reaction solution was stirred overnight at room temperature. An aqueous sodium bicarbonate solution was added to the reaction solution. The deposited precipitate was collected by filtration and washed with water and methanol. These procedures yielded 22.0 g of the product of interest.
Boc-Ser(Bzl)-Lys(ClZ)-Ile-Ser(Bzl)-Pro-Gln-Gly-Tyr(Br—Z)—NH$_2$ (SEQ ID NO: 42)

Boc-Lys(ClZ)-Ile-Ser(Bzl)-Pro-Gln-Gly-Tyr(Br—Z)—NH$_2$ (22.0 g) (SEQ ID NO: 41) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (3.8 mL) was added to the residue. Diethyl ether was added to the obtained mixture. The deposited precipitate was collected by filtration and washed with diethyl ether. The obtained hydrochloride salt was dissolved in N,N-dimethylformamide. Boc-Ser(Bzl)-OH (5.4 g) and 1-hydroxybenzotriazole (2.6 g) were added to the obtained solution. 1-Ethyl-3-(3-dimethylaminopropyl)carbodiimide (3.5 mL) was added dropwise to the mixture under cooling. The reaction solution was stirred overnight at room temperature. An aqueous sodium bicarbonate solution was added to the reaction solution. The deposited precipitate was collected by filtration and washed with water and methanol. These procedures yielded 20.2 g of the product of interest.
Boc-Arg(Tos)-Ser(Bzl)-Lys(ClZ)-Ile-Ser(Bzl)-Pro-Gln-Gly-Tyr(Br—Z)—NH$_2$ (segment 6) (SEQ ID NO: 43)

Boc-Ser(Bzl)-Lys(ClZ)-Ile-Ser(Bzl)-Pro-Gln-Gly-Tyr(Br—Z)—NH$_2$ (22.2 g) (SEQ ID NO: 42) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (3.0 mL) was added to the residue. Diethyl ether was added to the obtained mixture. The deposited precipitate was collected by filtration and washed with diethyl ether. The obtained hydrochloride salt was dissolved in N,N-dimethylformamide. Boc-Arg(Tos)-OH (7.3 g) and 1-hydroxybenzotriazole (2.1 g) were added to the obtained solution. 1-Ethyl-3-(3-dimethylaminopropyl)carbodiimide (2.8 mL) was added dropwise to the mixture under cooling. The reaction solution was stirred overnight at room temperature. An aqueous sodium bicarbonate solution was added to the reaction solution. The deposited precipitate was collected by filtration and washed with water and methanol. These procedures yielded 23.1 g of the product of interest.

[1-7: Segment Condensation of Protected h.AM—(1)]
Boc-Phe-Thr(Bzl)-Asp(OcHex)-Lys(ClZ)-Asp(OcHex)-Lys(ClZ)-Asp(OcHex)-Asn-Val-Ala-Pro-Arg(Tos)-Ser(Bzl)-Lys(ClZ)-Ile-Ser(Bzl)-Pro-Gln-Gly-Tyr(Br—Z)—NH$_2$ (SEQ ID NO: 44)

Boc-Arg(Tos)-Ser(Bzl)-Lys(ClZ)-Ile-Ser(Bzl)-Pro-Gln-Gly-Tyr(Br—Z)—NH$_2$ (1.9 g) (SEQ ID NO: 43) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (0.22 mL) was added to the residue. Diethyl ether was added to the obtained mixture. The deposited precipitate was collected by filtration and washed with diethyl ether. The obtained hydrochloride salt was dissolved in a 1-methyl-2-pyrrolidone/N,N-dimethylformamide mixed solution. Boc-Phe-Thr(Bzl)-Asp(OcHex)-Lys(ClZ)-Asp(OcHex)-Lys(ClZ)-Asp(OcHex)-Asn-Val-Ala-Pro-OH (2.0 g) (SEQ ID NO: 37) and 1-hydroxybenzotriazole (0.15 g) were added to the obtained solution. 1-Ethyl-3-(3-dimethylaminopropyl)carbodiimide (0.20 mL) was added dropwise to the mixture under cooling. The reaction solution was stirred overnight at room temperature. An aqueous sodium bicarbonate solution was added to the reaction solution. The deposited precipitate was collected by filtration and washed with water and diethyl ether. The residue was dissolved in N,N-dimethylformamide. The N,N-dimethylformamide was distilled off under reduced pressure from the obtained reaction solution, and ethyl acetate was added to the residue. The deposited precipitate was collected by filtration and washed with ethyl acetate. These procedures yielded 3.3 g of the product of interest.

[1-8: Segment Condensation of Protected h.AM—(2)]
Boc-His-Gln-Ile-Tyr(BrZ)-Gln-Phe-Thr(Bzl)-Asp(OcHex)-Lys(ClZ)-Asp(OcHex)-Lys(ClZ)-Asp(OcHex)-Asn-Val-Ala-Pro-Arg(Tos)-Ser(Bzl)-Lys(ClZ)-Ile-Ser(Bzl)-Pro-Gln-Gly-Tyr(Br—Z)—NH$_2$ (SEQ ID NO: 45)

Boc-Phe-Thr(Bzl)-Asp(OcHex)-Lys(ClZ)-Asp(OcHex)-Lys(ClZ)-Asp(OcHex)-Asn-Val-Ala-Pro-Arg(Tos)-Ser(Bzl)-Lys(ClZ)-Ile-Ser(Bzl)-Pro-Gln-Gly-Tyr(Br—Z)—

NH₂ (3.3 g) (SEQ ID NO: 44) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (0.19 mL) was added to the residue. Diethyl ether was added to the obtained mixture. The deposited precipitate was collected by filtration and washed with diethyl ether. The obtained hydrochloride salt was dissolved in 1-methyl-2-pyrrolidone. Boc-His-Gln-Ile-Tyr(BrZ)-Gln-OH (0.9 g) (SEQ ID NO: 29) and 3,4-dihydro-3-hydroxy-4-oxo-1,2,3-benzotriazine (0.13 g) were added to the obtained solution. 1-Ethyl-3-(3-dimethylaminopropyl)carbodiimide (0.18 mL) was added dropwise to the mixture under cooling. The reaction solution was stirred overnight at room temperature. An aqueous sodium bicarbonate solution was added to the reaction solution. The deposited precipitate was collected by filtration and washed with water and diethyl ether. The residue was dissolved in N,N-dimethylformamide. The N,N-dimethylformamide was distilled off under reduced pressure from the obtained solution, and acetonitrile was added to the residue. The deposited precipitate was collected by filtration and washed with acetonitrile. These procedures yielded 3.0 g of the product of interest.

[1-9: Segment Condensation of Protected h.AM—(3)]
Boc-Thr(Bzl)-Cys(4-MeBzl)-Thr(Bzl)-Val-Gln-Lys(ClZ)-Leu-Ala-His-Gln-Ile-Tyr(BrZ)-Gln-Phe-Thr(Bzl)-Asp(OcHex)-Lys(ClZ)-Asp(OcHex)-Lys(ClZ)-Asp(OcHex)-Asn-Val-Ala-Pro-Arg(Tos)-Ser(Bzl)-Lys(ClZ)-Ile-Ser(Bzl)-Pro-Gln-Gly- Tyr(Br—Z)—NH₂ (SEQ ID NO: 46)

Boc-His-Gln-Ile-Tyr(BrZ)-Gln-Phe-Thr(Bzl)-Asp(OcHex)-Lys(ClZ)-Asp(OcHex)-Lys(ClZ)-Asp(OcHex)-Asn-Val-Ala-Pro-Arg(Tos)-Ser(Bzl)-Lys(ClZ)-Ile-Ser(Bzl)-Pro-Gln-Gly-Tyr(Br—Z)—NH₂ (2.5 g) (SEQ ID NO: 45) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (0.23 mL) was added to the residue. Diethyl ether was added to the obtained mixture. The deposited precipitate was collected by filtration and washed with diethyl ether. The obtained hydrochloride salt was dissolved in a 1-methyl-2-pyrrolidone/N,N-dimethylformamide mixed solution. Boc-Thr(Bzl)-Cys(4-MeBzl)-Thr(Bzl)-Val-Gln-Lys(ClZ)-Leu-Ala-OH (0.78 g) (SEQ ID NO: 27) and 3,4-dihydro-3-hydroxy-4-oxo-1,2,3-benzotriazine (0.077 g) were added to the obtained solution. 1-Ethyl-3-(3-dimethylaminopropyl)carbodiimide (0.10 mL) was added dropwise to the mixture under cooling. The reaction solution was stirred overnight at room temperature. An aqueous sodium bicarbonate solution was added to the reaction solution. The deposited precipitate was collected by filtration and washed with water and diethyl ether. The residue was dissolved in a chloroform/2,2,2-trifluoroethanol mixed solution. The solvent was distilled off under reduced pressure from the obtained solution, and ethyl acetate was added to the residue. The deposited precipitate was collected by filtration and washed with ethyl acetate. These procedures yielded 2.1 g of the product of interest.

[I-10: Segment Condensation of Protected h.AM—(4)]
Boc-Leu-Arg(Tos)-Ser(Bzl)-Phe-Gly-Cys(4-MeBzl)-Arg(Tos)-Phe-Gly-Thr(Bzl)-Cys(4-MeBzl)-Thr(Bzl)-Val-Gln-Lys(ClZ)-Leu-Ala-His-Gln-Ile-Tyr(BrZ)-Gln-Phe-Thr(Bzl)-Asp(OcHex)-Lys(ClZ)-Asp(OcHex)-Lys(ClZ)-Asp(OcHex)-Asn-Val-Ala-Pro-Arg(Tos)-Ser(Bzl)-Lys(ClZ)-Ile-Ser(Bzl)-Pro-Gln-Gly-Tyr(Br—Z)—NH₂ (SEQ ID NO: 47)

Boc-Thr(Bzl)-Cys(4-MeBzl)-Thr(Bzl)-Val-Gln-Lys(ClZ)-Leu-Ala-His-Gln-Ile-Tyr(BrZ)-Gln-Phe-Thr(Bzl)-Asp(OcHex)-Lys(ClZ)-Asp(OcHex)-Lys(ClZ)-Asp(OcHex)-Asn-Val-Ala-Pro-Arg(Tos)-Ser(Bzl)-Lys(ClZ)-Ile-Ser(Bzl)-Pro-Gln-Gly- Tyr(Br—Z)—NH₂ (2.0 g) (SEQ ID NO: 46) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (0.15 mL) was added to the residue. Diethyl ether was added to the obtained mixture. The deposited precipitate was collected by filtration and washed with diethyl ether. The obtained hydrochloride salt was dissolved in a dimethyl sulfoxide/1-methyl-2-pyrrolidone/N,N-dimethylformamide mixed solution. Boc-Thr(Bzl)-Cys(4-MeBzl)-Thr(Bzl)-Val-Gln-Lys(ClZ)-Leu-Ala-OH (0.56 g) (SEQ ID NO: 27) and 1-hydroxybenzotriazole (0.091 g) were added to the obtained solution. 1-Ethyl-3-(3-dimethylaminopropyl)carbodiimide (0.12 mL) was added dropwise to the mixture under cooling. The reaction solution was stirred overnight at room temperature. An aqueous sodium bicarbonate solution was added to the reaction solution. The deposited precipitate was collected by filtration and washed with water and diethyl ether. The residue was dissolved in a chloroform/2,2,2-trifluoroethanol mixed solution. The solvent was distilled off under reduced pressure from the obtained solution, and acetonitrile was added to the residue. The deposited precipitate was collected by filtration and washed with acetonitrile. These procedures yielded 1.8 g of the product of interest.

[I-11: Segment Condensation of Protected h.AM—(5)]
Boc-Tyr(BrZ)-Arg(Tos)-Gln-Ser(Bzl)-Met-Asn-Asn-Phe-Gln-Gly-Leu-Arg(Tos)-Ser(Bzl)-Phe-Gly-Cys(4-MeBzl)-Arg(Tos)-Phe-Gly-Thr(Bzl)-Cys(4-MeBzl)-Thr(Bzl)-Val-Gln-Lys(ClZ)-Leu-Ala-His-Gln-Ile-Tyr(BrZ)-Gln-Phe-Thr(Bzl)-Asp(OcHex)-Lys(ClZ)-Asp(OcHex)-Lys(ClZ)-Asp(OcHex)-Asn-Val-Ala-Pro-Arg(Tos)-Ser(Bzl)-Lys(ClZ)-Ile- Ser(Bzl)-Pro-Gln-Gly-Tyr(Br—Z)—NH₂ (Boc-protected h.AM (1-52)) (SEQ ID NO:1)

Boc-Leu-Arg(Tos)-Ser(Bzl)-Phe-Gly-Cys(4-MeBzl)-Arg(Tos)-Phe-Gly-Thr(Bzl)-Cys(4-MeBzl)-Thr(Bzl)-Val-Gln-Lys(ClZ)-Leu-Ala-His-Gln-Ile-Tyr(BrZ)-Gln-Phe-Thr(Bzl)-Asp(OcHex)-Lys(ClZ)-Asp(OcHex)-Lys(ClZ)-Asp(OcHex)-Asn-Val-Ala-Pro-Arg(Tos)-Ser(Bzl)-Lys(ClZ)-Ile-Ser(Bzl)-Pro-Gln-Gly-Tyr(Br—Z)—NH₂ (1.5 g) (SEQ ID NO: 47) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (0.09 mL) was added to the residue. Diethyl ether was added to the obtained mixture. The deposited precipitate was collected by filtration and washed with diethyl ether. The obtained hydrochloride salt was dissolved in dimethyl sulfoxide. Boc-Tyr(BrZ)-Arg(Tos)-Gln-Ser(Bzl)-Met-Asn-Asn-Phe-Gln-Gly-OH (0.40 g) (SEQ ID NO: 18) and 1-hydroxybenzotriazole (0.081 g) were added to the obtained solution. 1-Ethyl-3-(3-dimethylaminopropyl)carbodiimide (0.11 mL) was added dropwise to the mixture under cooling. The reaction solution was stirred overnight at room temperature. An aqueous sodium bicarbonate solution was added to the reaction solution. The deposited precipitate was collected by filtration and washed with water and diethyl ether. The residue was dissolved in a chloroform/2,2,2-trifluoroethanol mixed solution. The solvent was distilled off under reduced pressure from the obtained solution, and diethyl ether was added to the residue. The deposited precipitate was collected by filtration and washed with diethyl ether. These procedures yielded 1.6 g of the product of interest.

[I-12: Synthesis of palmitoyl-h.AM—(1)]
Pal-Tyr(BrZ)-Arg(Tos)-Gln-Ser(Bzl)-Met-Asn-Asn-Phe-Gln-Gly-Leu-Arg(Tos)-Ser(Bzl)-Phe-Gly-Cys(4-MeBzl)-Arg(Tos)-Phe-Gly-Thr(Bzl)-Cys(4-MeBzl)-Thr(Bzl)-Val-Gln-Lys(ClZ)-Leu-Ala-His-Gln-Ile-Tyr(BrZ)-Gln-Phe-Thr(Bzl)-Asp(OcHex)-Lys(ClZ)-Asp(OcHex)-Lys(ClZ)-Asp(OcHex)-Asn-Val-Ala-Pro-Arg(Tos)-Ser(Bzl)-Lys(ClZ)-Ile-Ser(Bzl)-Pro-Gln-Gly-Tyr(Br—Z)—NH$_2$ (SEQ ID NO:1)

Boc-Tyr(BrZ)-Arg(Tos)-Gln-Ser(Bzl)-Met-Asn-Asn-Phe-Gln-Gly-Leu-Arg(Tos)-Ser(Bzl)-Phe-Gly-Cys(4-MeBzl)-Arg(Tos)-Phe-Gly-Thr(Bzl)-Cys(4-M eB z1)-Thr(Bzl)-Val-Gln-Lys(ClZ)-Leu-Ala-His-Gln-Ile-Tyr(BrZ)-Gln-Phe-Thr(Bzl)-Asp(OcHex)-Lys(ClZ)-Asp(OcHex)-Lys(ClZ)-Asp(OcHex)-Asn-Val-Ala-Pro-Arg(Tos)-Ser(Bzl)-Lys(ClZ)-Ile-Ser(Bzl)-Pro-Gln-Gly-Tyr(Br—Z)—NH$_2$ (0.23 g) (SEQ NO:1) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (0.02 mL) was added to the residue. Diethyl ether was added to the obtained mixture. The deposited precipitate was collected by filtration and washed with diethyl ether. The obtained hydrochloride salt was dissolved in a chloroform/2,2,2-trifluoroethanol mixed solution. A solution of palmitoyl chloride (0.015 g), 1-hydroxy-7-azabenzotriazole (0.015 g) and diisopropylethylamine (0.014 mL) added to tetrahydrofuran, and diisopropylethylamine (0.004 mL) were added dropwise to the obtained solution under cooling. The reaction solution was stirred overnight at room temperature. The solvent was distilled off under reduced pressure from the reaction solution, and acetonitrile was added to the residue. The deposited precipitate was collected by filtration and washed with acetonitrile. These procedures yielded 0.24 g of the product of interest.

[1-13: Synthesis of Palmitoyl-h.AM—(2)]
Pal-h.AM(1-52) trifluoroacetate
Pal-Tyr(BrZ)-Arg(Tos)-Gln-Ser(Bzl)-Met-Asn-Asn-Phe-Gln-Gly-Leu-Arg(Tos)-Ser(Bzl)-Phe-Gly-Cys(4-MeBzl)-Arg(Tos)-Phe-Gly-Thr(Bzl)-Cys(4-MeBzl)-Thr(Bzl)-Val-Gln-Lys(ClZ)-Leu-Ala-His-Gln-Ile-Tyr(BrZ)-Gln-Phe-Thr(Bzl)-Asp(OcHex)-Lys(ClZ)-Asp(OcHex)-Lys(ClZ)-Asp(OcHex)-Asn-Val-Ala-Pro-Arg(Tos)-Ser(Bzl)-Lys(ClZ)-Ile-Ser(Bzl)-Pro-Gln-Gly-Tyr(Br—Z)—NH$_2$ (238 mg) (SEQ ID NO:1) was supplemented with p-cresol (1.5 mL) and methionine (37 mg). Anhydrous hydrogen fluoride (6 mL) was added to the obtained solution under cooling. The reaction solution was treated at −2 to −5° C. for 60 minutes. The anhydrous hydrogen fluoride was distilled off under reduced pressure from the reaction solution, and diethyl ether was added to the residue. The deposited precipitate was collected by filtration. The obtained crude peptide was dissolved in a 50% aqueous acetic acid solution. A 0.1 M solution of iodine in methanol (0.24 mL) was added to the obtained solution. After 1 minute, 1 M ascorbic acid in water (0.24 mL) was added to the solution. The product of interest was purified by reverse-phase HPLC from the obtained solution. The product of interest was lyophilized and then obtained as 38 mg of white powder.

[I-14: Synthesis of Palmitoyl-h.AM—(3)]
Pal-h.AM(1-52) Acetate
Pal-h.AM(1-52) trifluoroacetate (38 mg) was dissolved in a 5% aqueous acetic acid solution. The obtained solution was applied to Muromac 1×2 (acetic acid type) column (3 mL), followed by elution with a 5% aqueous acetic acid solution. The eluate was lyophilized. The product of interest was lyophilized and then obtained as 32 mg of white powder.

[I-15: Synthesis of Palmitoyl-h.AM—(4)]
Packing Pal-h.AM(1-52) Acetate in Vials
Pal-h.AM(1-52) acetate (16.5 mg) was dissolved in Milli Q water (18.3 mL). The obtained solution was dispensed at 0.30 mL to each vial and lyophilized. Three of the obtained lyophilized products in the vials were hydrolyzed with a 6 M aqueous hydrochloric acid solution. The obtained hydrolysates were subjected to amino acid analysis. The contents were quantified by the amino acid analysis. Yield: 38 nmol× 57 vials.

[I-16: Synthesis of PEG5000-h.AM—(1)]
Fmoc-Tyr(BrZ)-Arg(Tos)-Gln-Ser(Bzl)-Met-Asn-Asn-Phe-Gln-Gly-Leu-Arg(Tos)-Ser(Bzl)-Phe-Gly-Cys(4-MeBzl)-Arg(Tos)-Phe-Gly-Thr(Bzl)-Cys(4-MeBzl)-Thr(Bzl)-Val-Gln-Lys(ClZ)-Leu-Ala-His-Gln-Ile-Tyr(BrZ)-Gln-Phe-Thr(Bzl)-Asp(OcHex)-Lys(ClZ)-Asp(OcHex)-Lys(ClZ)-Asp(OcHex)-Asn-Val-Ala-Pro-Arg(Tos)-Ser(Bzl)-Lys(ClZ)-Ile-Ser(Bzl)-Pro-Gln-Gly-Tyr(Br—Z)—NH$_2$ (SEQ ID NO:1)

Boc-Tyr(BrZ)-Arg(Tos)-Gln-Ser(Bzl)-Met-Asn-Asn-Phe-Gln-Gly-Leu-Arg(Tos)-Ser(Bzl)-Phe-Gly-Cys(4-MeBzl)-Arg(Tos)-Phe-Gly-Thr(Bzl)-Cys(4-MeBzl)-Thr(Bzl)-Val-Gln-Lys(ClZ)-Leu-Ala-His-Gln-Ile-Tyr(BrZ)-Gln-Phe-Thr(Bzl)-Asp(OcHex)-Lys(ClZ)-Asp(OcHex)-Lys(ClZ)-Asp(OcHex)-Asn-Val-Ala-Pro-Arg(Tos)-Ser(Bzl)-Lys(ClZ)-Ile-Ser(Bzl)-Pro-Gln-Gly-Tyr(Br—Z)—NH$_2$ (0.9 g) (SEQ ID NO:1) was dissolved in trifluoroacetic acid. The obtained solution was stirred for 10 minutes under cooling and then at room temperature for 50 minutes. The trifluoroacetic acid was distilled off under reduced pressure from the reaction solution, and a solution of hydrogen chloride in dioxane (5.5 mol/L) (0.05 mL) was added to the residue. Diethyl ether was added to the obtained mixture. The deposited precipitate was collected by filtration and washed with diethyl ether. The obtained hydrochloride salt was dissolved in a dimethyl sulfoxide/N,N-dimethylformamide mixed solution. 9-Fluorenylmethyl succinimidyl carbonate (0.34 g) and diisopropylethylamine (0.05 mL) were added to the obtained solution. The reaction solution was stirred overnight at room temperature. Water was added to the reaction solution. The deposited precipitate was collected by filtration and washed with water and acetonitrile. The precipitate was dissolved in a chloroform/2,2,2-trifluoroethanol mixed solution. The solvent was distilled off under reduced pressure, and diethyl ether was added to the residue. The deposited precipitate was collected by filtration and washed with diethyl ether. These procedures yielded 0.76 g of the product of interest.

[1-17: Synthesis of PEG5000-h.AM—(2)]
Fmoc-Tyr-Arg-Gln-Ser-Met-Asn-Asn-Phe-Gln-Gly-Leu-Arg-Ser-Phe-Gly-Cys-Arg-Phe-Gly-Thr-Cys-Thr-Val-Gln-Lys-Leu-Ala-His-Gln-Ile-Tyr-Gln-Phe-Thr-Asp-Lys-Asp-Lys-Asp-Asn-Val-Ala-Pro-Arg-Ser-Lys-Ile-Ser-Pro-Gln-Gly-Tyr-NH$_2$ (Cys16-Cys21 disulfide bridge form) (SEQ ID NO:1)

Fmoc-Tyr(BrZ)-Arg(Tos)-Gln-Ser(Bzl)-Met-Asn-Asn-Phe-Gln-Gly-Leu-Arg(Tos)-Ser(Bzl)-Phe-Gly-Cys(4-MeBzl)-Arg(Tos)-Phe-Gly-Thr(Bzl)-Cys(4-MeBzl)-Thr(Bzl)-

Val-Gln-Lys(ClZ)-Leu-Ala-His-Gln-Ile-Tyr(BrZ)-Gln-Phe-Thr(Bzl)-Asp(OcHex)-Lys(ClZ)-Asp(OcHex)-Lys(ClZ)-Asp(OcHex)-Asn-Val-Ala-Pro-Arg(Tos)-Ser(Bzl)-Lys (ClZ)-Ile- Ser(Bzl)-Pro-Gln-Gly-Tyr(Br—Z)—NH$_2$ (740 mg) SEQ ID NO:1) was supplemented with p-cresol (6.0 mL) and methionine (122 mg). Anhydrous hydrogen fluoride (24 mL) was added to the obtained solution under cooling. The reaction solution was treated at −2 to −5° C. for 60 minutes. The anhydrous hydrogen fluoride was distilled off under reduced pressure from the reaction solution, and diethyl ether was added to the residue. The deposited precipitate was collected by filtration. The obtained crude peptide was dissolved in a 50% aqueous acetic acid solution. A 0.1 M solution of iodine in methanol (0.8 mL) was added to the obtained solution. After 30 seconds, 1 M ascorbic acid in water (0.8 mL) was added to the solution. The product of interest was purified by reverse-phase HPLC from the obtained solution. The product of interest was lyophilized and then obtained as 134 mg of white powder.

[1-18: Synthesis of PEG5000-h.AM—(3)]
Tyr-Arg-Gln-Ser-Met-Asn-Asn-Phe-Gln-Gly-Leu-Arg-Ser-Phe-Gly-Cys-Arg-Phe-Gly-Thr-Cys-Thr-Val-Gln-Lys (Boc)-Leu-Ala-His-Gln-Ile-Tyr-Gln-Phe-Thr-Asp-Lys (Boc)-Asp-Lys(Boc)-Asp-Asn-Val-Ala-Pro-Arg-Ser-Lys (Boc)-Ile-Ser-Pro-Gln-Gly- Tyr-NH$_2$ (Cys16-Cys21 disulfide bridge form) (SEQ ID NO:1)

Fmoc-Tyr-Arg-Gln-Ser-Met-Asn-Asn-Phe-Gln-Gly-Leu-Arg-Ser-Phe-Gly-Cys-Arg-Phe-Gly-Thr-Cys-Thr-Val-Gln-Lys-Leu-Ala-His-Gln-Ile-Tyr-Gln-Phe-Thr-Asp-Lys-Asp-Lys-Asp-Asn-Val-Ala-Pro-Arg-Ser-Lys-Ile-Ser-Pro-Gln-Gly-Tyr-NH$_2$ (Cys16-Cys21 disulfide bridge form) (184 mg) (SEQ ID NO:1) was dissolved in dimethyl sulfoxide (18 mL). t-Butyl succinimidyl carbonate (87 mg) and diisopropylethylamine (0.06 mL) were added to the obtained solution. The reaction solution was stirred for 5 hours. An aqueous acetic acid solution was added to the reaction solution, and then the mixture was lyophilized. The residue was dissolved in dimethyl sulfoxide (20 mL). Diethylamine (2 mL) was added to the obtained solution. The obtained solution was stirred for 70 minutes. The reaction solution was diluted by the addition of an aqueous acetic acid solution. The product of interest was purified by reverse-phase HPLC from the obtained solution. The product of interest was lyophilized and then obtained as 116 mg of white powder.

[1-19: Synthesis of PEG5000-h.AM—(4)]
PEG5000-Tyr-Arg-Gln-Ser-Met-Asn-Asn-Phe-Gln-Gly-Leu-Arg-Ser-Phe-Gly-Cys-Arg-Phe-Gly-Thr-Cys-Thr-Val-Gln-Lys(Boc)-Leu-Ala-His-Gln-Ile-Tyr-Gln-Phe-Thr-Asp-Lys(Boc)-Asp-Lys(Boc)-Asp-Asn-Val-Ala-Pro-Arg-Ser-Lys(Boc)-Ile- Ser-Pro-Gln-Gly-Tyr-NH$_2$ (Cys16-Cys21 disulfide bridge form) (SEQ ID NO:1)

Tyr-Arg-Gln-Ser-Met-Asn-Asn-Phe-Gln-Gly-Leu-Arg-Ser-Phe-Gly-Cys-Arg-Phe-Gly-Thr-Cys-Thr-Val-Gln-Lys (Boc)-Leu-Ala-His-Gln-Ile-Tyr-Gln-Phe-Thr-Asp-Lys (Boc)-Asp-Lys(Boc)-Asp-Asn-Val-Ala-Pro-Arg-Ser-Lys (Boc)-Ile-Ser-Pro-Gln-Gly- Tyr-NH$_2$ (Cys16-Cys21 disulfide bridge form) (40 mg) (SEQ ID NO:1) was dissolved in dimethyl sulfoxide (4 mL). PEG5000-NHS (205 mg) and diisopropylethylamine (0.001 mL) were added to the obtained solution. PEG5000-NHS is a compound formed from PEG having an average molecular weight of 5000 and 6-chlorohexanoic acid N-hydroxysuccinimide ester. This compound has a structure in which the PEG having an average molecular weight of 5000 and the N-hydroxysuccinimide are linked via 1-oxo-1,6-hexanediyl. The reaction solution was stirred overnight. The product of interest was purified by reverse-phase HPLC from the reaction solution. The product of interest was lyophilized and then obtained as 35 mg of white powder.

[1-20: Synthesis of PEG5000-h.AM—(5)]
PEG5000-h.AM(1-52) Trifluoroacetate
PEGS 000-Tyr-Arg-Gln-Ser-Met-Asn-Asn-Phe-Gln-Gly-Leu-Arg-Ser-Phe-Gly-Cys-Arg-Phe-Gly-Thr-Cys-Thr-Val-Gln-Lys(Boc)-Leu-Ala-His-Gln-Ile-Tyr-Gln-Phe-Thr-Asp-Lys(Boc)-Asp-Lys(Boc)-Asp-Asn-Val-Ala-Pro-Arg-Ser-Lys(Boc)-Ile- Ser-Pro-Gln-Gly-Tyr-NH$_2$ (Cys16-Cys21 disulfide bridge form) (34 mg) (SEQ ID NO:1) was supplemented with a 95% aqueous trifluoroacetic acid solution (5 mL) under ice cooling to dissolve the crude peptide. The obtained mixture was reacted for 40 minutes under ice cooling. The solvent was distilled off under reduced pressure from the reaction solution. The residue was dissolved in Milli Q water. The product of interest was purified by reverse-phase HPLC from the obtained solution. The product of interest was lyophilized and then obtained as 30 mg of white powder.

[I-21: Synthesis of PEG5000-h.AM—(6)]
Packing PEG5000-h.AM(1-52) Acetate in Vials
PEG5000-h.AM(1-52) trifluoroacetate (30 mg) was dissolved in a 3% aqueous acetic acid solution. The obtained solution was applied to Muromac 1×2 (acetic acid type) column (2 mL), followed by elution with a 3% aqueous acetic acid solution. The eluate was lyophilized. The whole amount of the lyophilized product was dissolved in Milli Q water (18.3 mL). The obtained solution was dispensed at 0.30 mL to each vial and lyophilized. Three of the obtained lyophilized products in the vials were hydrolyzed with a 6 M aqueous hydrochloric acid solution. The obtained hydrolysates were subjected to amino acid analysis. The contents were quantified by the amino acid analysis. Yield: 37 nmol× 56 vials.

<II: Use Examples>
[II-1: Intracellular cAMP Concentration-Increasing Effect of Adrenomedullin Derivative]

The administration of adrenomedullin (AM) increases the concentration of intracellular cAMP. Therefore, the effect of AM is considered to be exerted via increase in the concentration of intracellular cAMP. Accordingly, Pal-h.AM(1-52), PEG5000-h.AM(1-52) or h.AM(1-52) was added to a cultured cell line (HEK293 cell line) caused to express an AM receptor, and the amount of intracellular cAMP produced was measured. $10^{-11}$ to $10^{-6}$ mol/L of Pal-h.AM(1-52), PEG5000-h.AM(1-52) or h.AM(1-52) was added to confluent HEK293 cells (the number of cells: $5\times10^4$) in the presence of 0.5 mM IBMX and incubated for 15 minutes. Then, the intracellular cAMP concentration in the HEK293 cells of each test sample was measured using an ELISA kit for cAMP measurement (GE Healthcare Japan Corp., #RPN2251). The dose-response curve between the concentration of Pal-h.AM(1-52), PEG5000-h.AM(1-52) or h.AM (1-52) and increase in cAMP concentration is shown in FIG. 1. In the figure, the longitudinal axis indicates the relative value (%) of increase in cAMP concentration of each test sample to the maximum response value of increase in cAMP concentration caused by h.AM(1-52).

As shown in FIG. 1, the administration of Pal-h.AM(1-52) or PEG5000-h.AM(1-52) increased the intracellular cAMP concentration in the AM receptor-expressing HEK293 cells. Pal-h.AM(1-52) and PEG5000-h.AM(1-52), as compared with h.AM(1-52), exhibited substantially equivalent maximum response values and pEC50 values (h.AM(1-52): 8.59±0.90; Pal-h.AM(1-52): 8.49±0.12; PEG5000-h.AM(1-52): 8.19±0.10). These results have demonstrated that Pal-h.AM(1-52) and PEG5000-h.AM(1-52) exert cAMP concentration-increasing activity substantially equivalent to that of h.AM(1-52) in cultured cells.

[II-2: Half-Life in Blood of Adrenomedullin Derivative]

Figure 2:
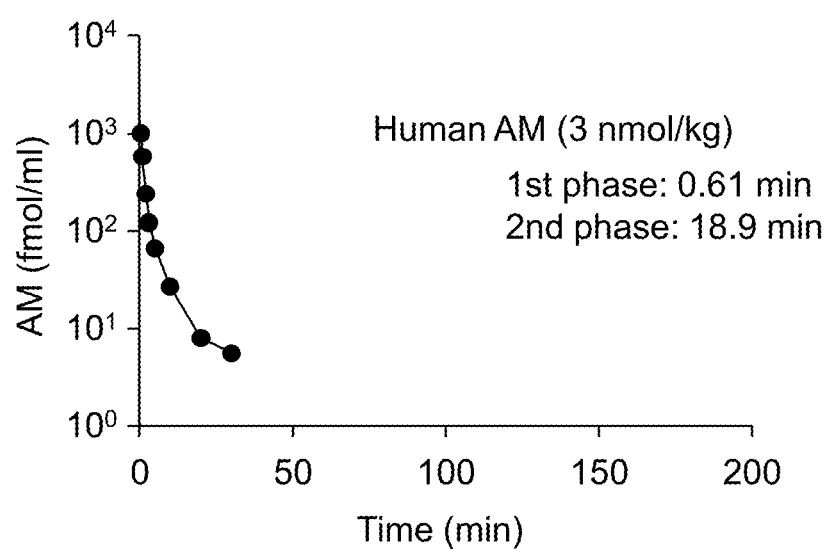
FIG. 2 shows the relationship between the duration of time from the start of administration of h.AM (1-52) and AM concentration in blood plasma.

A single dose of Pal-h.AM(1-52), PEG5000-h.AM(1-52) or h.AM(1-52) was administered into the vein of each rat under anesthesia, and time-dependent change in the concentration in blood of the adrenomedullin derivative was observed. Each 11 to 14-week-old male Wistar rat was anesthetized by the inhalation of isoflurane. After tracheotomy, inhalational anesthesia was controlled at an isoflurane concentration of 1.5 to 2.5% and a flow rate of 0.6 to 0.8 L/min. The right jugular vein was isolated from the rat, and a catheter tube corresponding to 26 G was inserted thereto. Next, the left carotid artery was isolated from the rat thus treated, and a catheter tube corresponding to 23 G was inserted thereto. Pal-h.AM(1-52), PEG5000-h.AM(1-52) or h.AM(1-52) dissolved in physiological saline was administered through the catheter tube of the right jugular vein. From the catheter inserted in the carotid artery, 300 μl of blood was collected over time from the start of the administration. Immediately, EDTA-2Na (300 μg) and aprotinin (21 μg) were added to the obtained blood sample, and the mixture was further centrifuged under conditions involving 3000 rpm and 10 minutes to obtain plasma. The AM concentration in the plasma of each sample was measured by chemiluminescent enzyme immunoassay. The half-lives in blood of the first and second phases were calculated from the measurement results of the AM concentration in the plasma using a two-compartment model. The relationship between the duration of time from the start of the administration of h.AM(1-52), Pal-h.AM(1-52) or PEG5000-h.AM(1-52) and the AM concentration in the plasma is shown in FIGS. 2 to 4.

Figure 3:
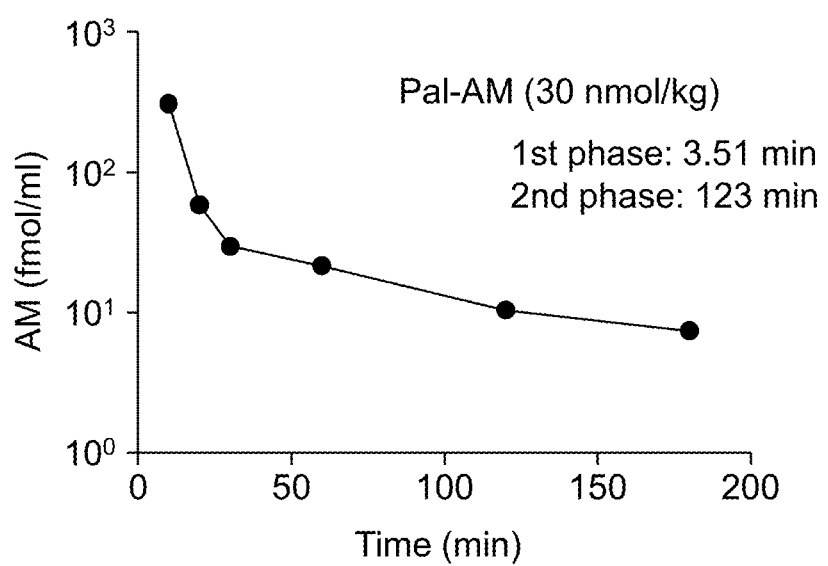
FIG. 3 shows the relationship between the duration of time from the start of administration of Pal-h.AM (1-52) and AM concentration in blood plasma.
Figure 4:
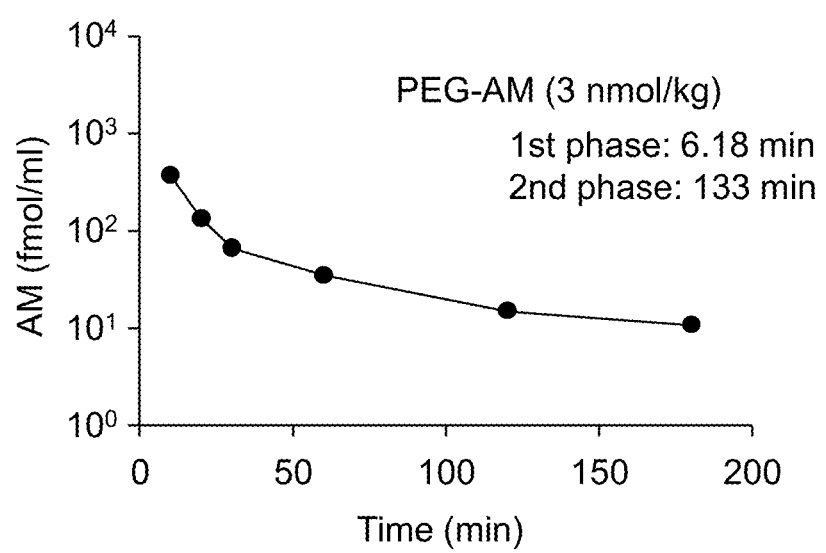
FIG. 4 shows the relationship between the duration of time from the start of administration of PEG5000-h.AM (1-52) and AM concentration in blood plasma.

As shown in FIGS. 3 and 4, the first-phase half-lives of Pal-h.AM(1-52) and PEG5000-h.AM(1-52) were 3.51 and 6.18 minutes, respectively, and the second-phase half-lives thereof were 123 and 133 minutes, respectively. By contrast, as shown in FIG. 2, the first-phase half-life of h.AM(1-52) was 0.61 minutes, and the second-phase half-life thereof was 18.9 minutes. In short, Pal-h.AM(1-52) and PEG5000-h.AM (1-52), as compared with h.AM(1-52), significantly prolonged the half-life in blood. These results have demonstrated that an adrenomedullin molecule chemically modified with palmitic acid or polyethylene glycol significantly prolongs a half-life in blood, as compared with the parent molecule adrenomedullin.

[II-3: Blood Pressure-Lowering Effect of Adrenomedullin Derivative]

Figure 5:
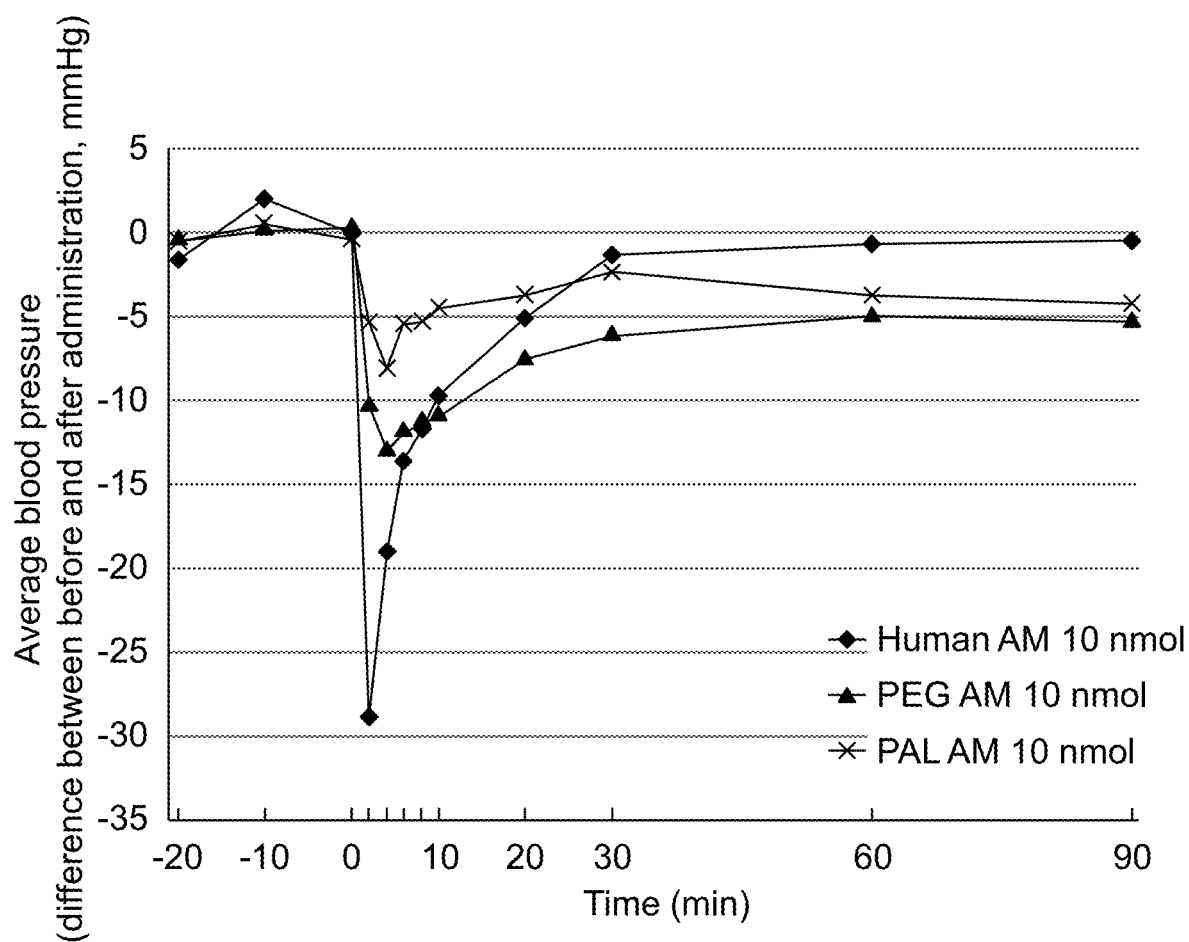
FIG. 5 shows the relationship between the duration of time from the start of administration of h.AM (1-52), Pal-h.AM (1-52), or PEG5000-h.AM (1-52) and the average blood pressure.

A single dose of Pal-h.AM(1-52), PEG5000-h.AM(1-52) or h.AM(1-52) was administered into the vein of each rat under anesthesia, and change in the blood pressure of the rat was observed. Each 11 to 14-week-old male Wistar rat was anesthetized by the inhalation of isoflurane. After tracheotomy, inhalational anesthesia was controlled at an isoflurane concentration of 1.5 to 2.5% and a flow rate of 0.6 to 0.8 L/min. The right jugular vein was isolated from the rat, and a catheter tube corresponding to 26 G was inserted thereto. Next, the left carotid artery was isolated from the rat thus treated, and a catheter tube corresponding to 23 G was inserted thereto. Pal-h.AM(1-52), PEG5000-h.AM(1-52) or h.AM(1-52) dissolved in physiological saline was administered through the catheter tube of the right jugular vein. From the catheter tube of the right jugular vein, a physiological saline-heparin solution (physiological saline: 100 ml; heparin: 1000 units) was infused at 2.4 ml/hr. From this catheter tube, 10 nmol/kg of Pal-h.AM(1-52), PEG5000-h.AM(1-52) or h.AM(1-52) was administered in a form dissolved in physiological saline. The catheter inserted in the carotid artery was connected to a pressure transducer. The blood pressure before the administration of Pal-h.AM(1-52), PEG5000-h.AM(1-52) or h.AM(1-52) and the blood pressure after the administration thereof were measured over time. The relationship between the duration of time from the start of the administration of h.AM(1-52), Pal-h.AM(1-52) or PEG5000-h.AM(1-52) and the average blood pressure is shown in FIG. 5. In the figure, the longitudinal axis indicates a difference obtained by subtracting the average blood pressure before the administration of each drug from the average blood pressure at the time of the administration of each drug.

As shown in FIG. 5, the intravenous single dose of Pal-h.AM(1-52), PEG5000-h.AM(1-52) or h.AM(1-52) at 10 nmol/kg lowered the blood pressure of the rat. In the case of h.AM(1-52), the maximum pressure drop was observed 2 minutes after the administration, and the blood pressure before the administration was restored 30 minutes after the administration. By contrast, the maximum pressure drop value brought about by the administration of Pal-h.AM(1-52) or PEG5000-h.AM(1-52) was lower than the value of h.AM(1-52). In the case of these derivatives, the blood pressure-lowering effect was sustained even 90 minutes after the administration. These results have demonstrated that the blood pressure-lowering effects of Pal-h.AM(1-52) and PEG5000-h.AM(1-52) last gradually and for a long time. The blood pressure-lowering effect of the adrenomedullin derivative shown in this test was well consistent with the prolonged half-life in blood shown in the above test.

[II-4: Therapeutic Effect of Adrenomedullin Derivative on Inflammatory Bowel Disease Model]

II-4-1: Preparation of Model

The skin of the back of each $C_{57}BL/6J$ Jcl mouse (6 weeks old) was incised under inhalational anesthesia with isoflurane (2%). An osmotic pump (model 1002 Alzet® mini osmotic pump) filled with an administration solution was subcutaneously implanted, and the skin was sutured with a suture thread. The skin of the back at the osmotic pump-implanted site was shaved and disinfected. The mouse thus treated was allowed to ingest 3 mass/vol % of sodium dextran sulfate (DSS) (Wako Pure Chemical Industries, Ltd.) as drinking water for 7 days to prepare an inflammatory bowel disease model. DSS-induced enteritis is widely used as a model for inflammatory bowel disease.

From the start date of the DSS ingestion, the adrenomedullin derivative (PEG5000-h.AM(1-52)) was continuously subcutaneously administered using the osmotic pump. The dose was set to 0.02, 0.1 or 0.5 nmol/kg/hr, and the dosing rate was set to 0.2 μL/hr. The start date of the DSS ingestion was defined as the start date of the adrenomedullin derivative administration (day 0). The administration was carried out for 14 days under the conditions described above. Physiological saline was administered to a control group in the same way as above. 14 days after the start of the administration, heparinized blood was collected from the abdominal cava under inhalational anesthesia with isoflurane (2%). The abdominal aorta and the abdominal cava were incised so that the animal was euthanized by exsanguination. Next, the intestinal tract from the anus to the ileocecum was collected.

II-4-2: Measurement (1) AM Concentration

The heparinized blood collected according to the procedures described above was centrifuged under conditions involving 4° C., 1800×g and 10 minutes to obtain plasma.

The AM concentration in the obtained plasma of each sample was measured by chemiluminescent enzyme immunoassay.

(2) Body weight

The body weight of the subject mouse was measured 3, 5, 7, 10 and 14 days after the start of the administration.

(3) Score

The body weight of the subject mouse and the form of stool thereof were evaluated 3, 5, 7, 10 and 14 days after the start of the administration on the basis of scoring criteria given below. The obtained scores were summed to calculate the total score of each sample.

TABLE 1

| Weight loss | Scoring criteria | Stool consistency | Scoring criteria | Bleeding/mucous and bloody stool | Scoring criteria |
| --- | --- | --- | --- | --- | --- |
| 0 | Weight loss Absent | 0 | Normal | 0 | Normal |
| 1 | Weight loss 1-5% | 2 | Loose stool | 2 | Bleeding |
| 2 | Weight loss 5-10% | 4 | Diarrhea | 4 | Mucous and bloody stool |
| 3 | Weight loss 10-20% | | | | |

(4) Length of intestinal tract

The intestinal tract excised by anatomy was opened along its longitudinal axis, and fat tissues were removed, followed by washing with physiological saline. Next, the length of the intestinal tract was measured.

II-4-3: Results (1) AM Concentration

Figure 6:
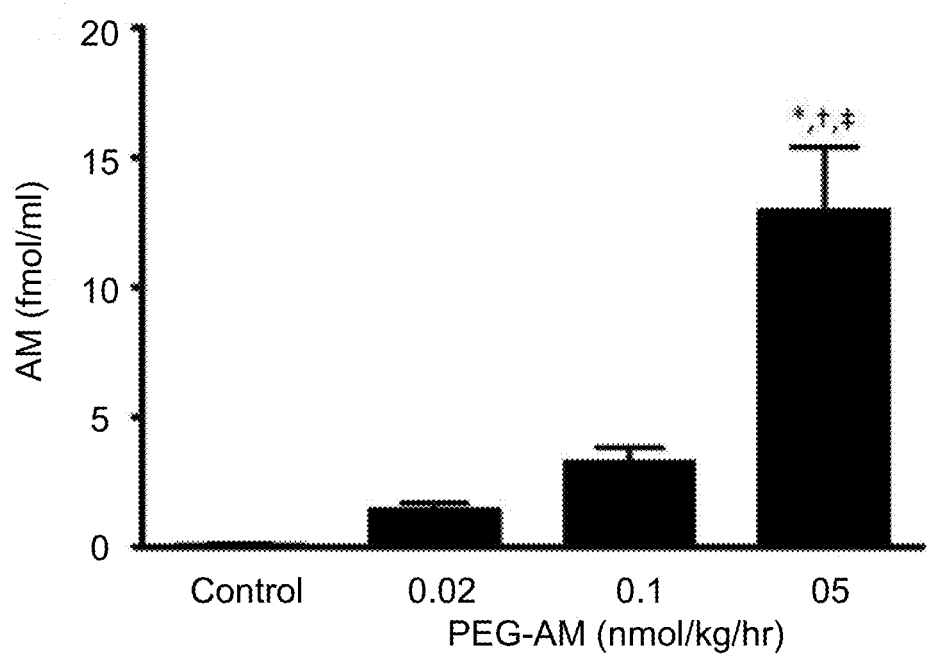
FIG. 6 shows AM concentrations in blood plasma in the control group and administration groups of 0.02, 0.1, and 0.5 nmol/kg/hr PEG5000-h.AM (1-52).

The AM concentration in the plasma measured by the procedures described above is indicated by mean±standard deviation. The AM concentrations in the plasma of the control group and the 0.02, 0.1 and 0.5 nmol/kg/hr PEG5000-h.AM(1-52) administration groups were 0.091±0.036, 1.430±0.242, 3.289±0.525 and 12.96±2.432 fmol/ml, respectively. The AM concentrations in the plasma of the control group and the 0.02, 0.1 and 0.5 nmol/kg/hr PEG5000-h.AM(1-52) administration groups are shown in FIG. 6.

(2) Score Evaluation

Figure 7:
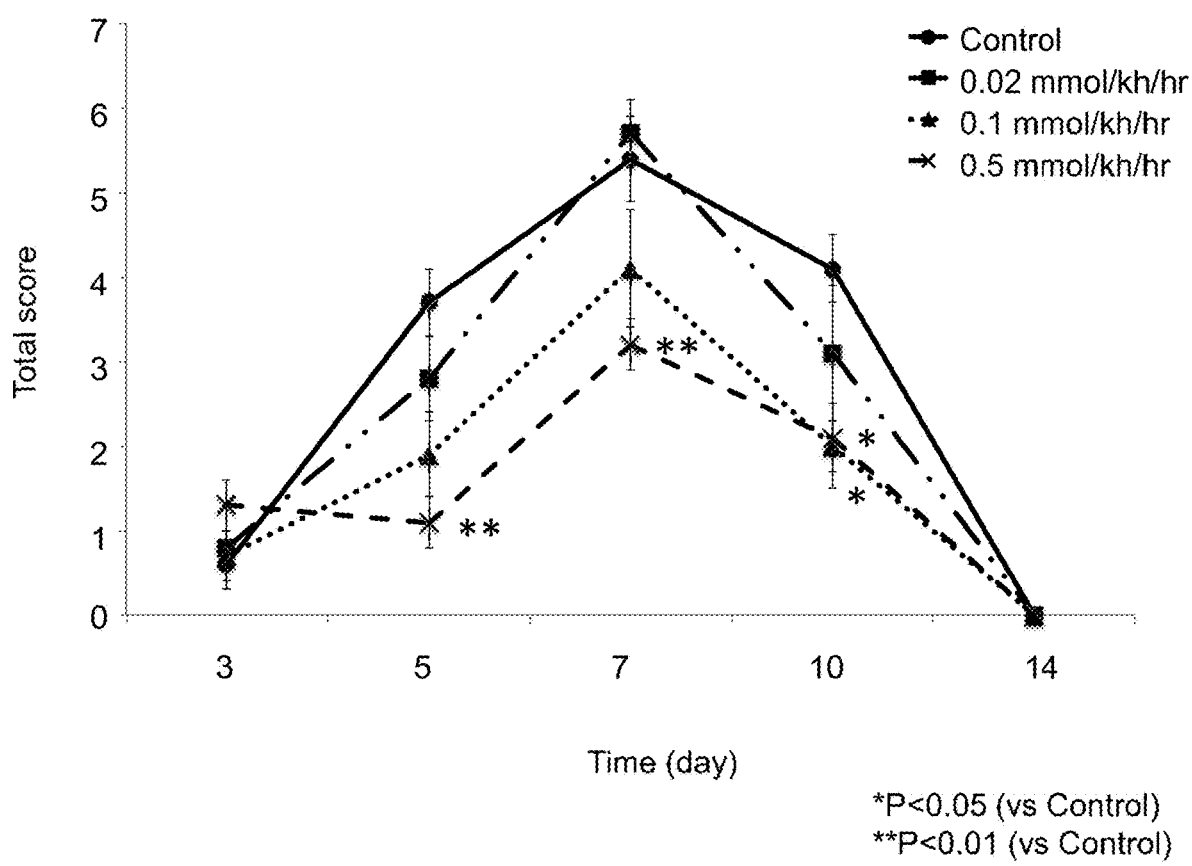
FIG. 7 shows the relationship between the duration of time from the start of administration of PEG5000-h.AM (1-52) and the total scores in the control group and each administration group.

The total score evaluated by the procedures described above is indicated by a median value [mean±standard deviation]. The total scores of the control group obtained 3, 5, 7, 10 and 14 days after the start of the administration were 0.0 [0.6±0.3], 4.0 [3.7±0.4], 6.0 [5.4±0.5], 3.5 [4.1±0.4] and 0.0 [0.0±0.0], respectively. The total scores of the 0.02 nmol/kg/hr PEG5000-h.AM(1-52) administration group obtained 3, 5, 7, 10 and 14 days after the start of the administration were 1.0 [0.8±0.2], 2.5 [2.8±0.5], 5.5 [5.7±0.4], 2.5 [3.1±0.8] and 0.0 [0.0±0.0], respectively. The total scores of the 0.1 nmol/kg/hr PEG5000-h.AM(1-52) administration group obtained 3, 5, 7, 10 and 14 days after the start of the administration were 0.0 [0.7±0.3], 1.5 [1.9±0.5], 5.0 [4.1±0.4], 2.0 [2.0±0.5] and 0.0 [0.0±0.0], respectively. The total scores of the 0.5 nmol/kg/hr PEG5000-h.AM(1-52) administration group obtained 3, 5, 7, 10 and 14 days after the start of the administration were 1.0 [1.3±0.3], 1.5 [1.1±0.3], 3.0 [3.0±0.3], 2.0 [2.1±0.4] and 0.0 [0.0±0.0], respectively. The relationship between the duration of time from the start of the administration of PEG5000-h.AM(1-52) and the total scores of the control group and each administration group is shown in FIG. 7. As shown in FIG. 7, the total scores obtained 10 days after the start of the administration in the 0.1 nmol/kg/hr PEG5000-h.AM(1-52) administration group, and the total scores obtained 5, 7 and 10 days after the start of the administration in the 0.5 nmol/kg/hr PEG5000-h.AM(1-52) administration group, as compared with the total scores of the control group, were all found to exhibit significant decrease (Steel's multiple comparison test, p<0.05 or P<0.01).

(3) Length of Intestinal Tract

Figure 8:
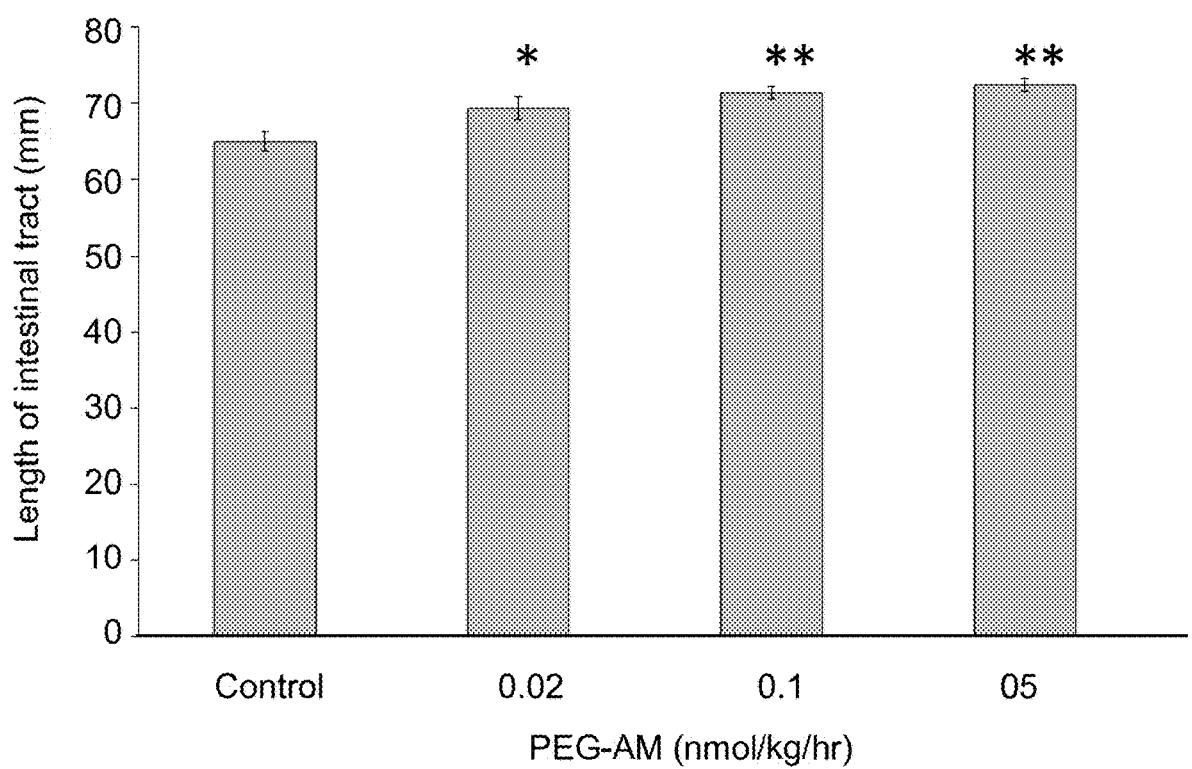
FIG. 8 shows the lengths of intestinal tract in the control group and the administration groups of 0.02, 0.1, and 0.5 nmol/kg/hr PEG5000-h.AM (1-52).

The length of the intestinal tract measured by the procedures described above is indicated by mean±standard deviation. The lengths of the intestinal tracts of the control group and the 0.02, 0.1 and 0.5 nmol/kg/hr PEG5000-h.AM(1-52) administration groups were 65.0±1.3, 69.4±1.5, 71.4±0.9 and 72.4±0.9 mm, respectively. The lengths of the intestinal tracts of the control group and the 0.02, 0.1 and 0.5 nmol/kg/hr PEG5000-h.AM(1-52) administration groups are shown in FIG. 8. As shown in FIG. 8, the lengths of the intestinal tracts of all the PEG5000-h.AM(1-52) administration groups treated at the concentrations were confirmed to be significantly different from the length of the intestinal tract of the control group (Dunnett's multiple comparison test, P<0.05 or P<0.01).

All publications, patent and patent applications cited herein are incorporated herein by reference in their entirety.

The invention claimed is:

1. A compound represented by formula (I):

A-L$_n$-B    (I)

wherein
A is a polyethylene glycol group having an average molecular weight of from 500 to 40,000,
L is a divalent linking group,
n is an integer of 0 or 1, and
B is a peptide derived from adrenomedullin or a modified form thereof with adrenomedullin activity, said B comprising
  (i) a peptide that consists of an amino acid sequence of the adrenomedullin, has a disulfide bond formed by two cysteine residues in the amino acid sequence, and has a C-terminus that is amidated, or
  (ii) a peptide wherein 1 to 15 amino acids in the peptide of (i) are deleted from a N-terminus and that has the adrenomedullin activity, wherein the peptide B is bound to the polyethylene glycol group A or the linking group L only via an N-terminal α-amino group of the peptide B or a salt thereof, or a hydrate thereof.

2. The compound according to claim 1, wherein said B comprises a peptide selected from the group consisting of:
  (a) a peptide consisting of the amino acid sequence of SEQ ID NO: 1, having a disulfide bond formed by the cysteine residues at positions 16 and 21, and having a C-terminus that is amidated;
  (b) a peptide consisting of the amino acid sequence of the SEQ ID NO: 4, having a disulfide bond formed by the cysteine residues at positions 16 and 21, and having a C-terminus that is amidated;
  (c) a peptide consisting of the amino acid sequence of SEQ ID NO: 6 having a disulfide bond formed by the cysteine residues at positions 16 and 21, and having a C-terminus that is amidated;

(d) a peptide consisting of the amino acid sequence of SEQ ID NO: 8, having a disulfide bond formed by the cysteine residues at positions 16 and 21, and having a C-terminus that is amidated;

(e) a peptide consisting of the amino acid sequence of SEQ ID NO: 10, having a disulfide bond formed by the cysteine residues at positions 14 and 19, and having a C-terminus that is amidated;

(f) a peptide consisting of the amino acid sequence of SEQ ID NO: 12, having a disulfide bond formed by the cysteine residues at positions 14 and 19, and having a C-terminus that is amidated; and (g) a peptide wherein 1 to 15 amino acids in any of the peptides of (a) to (f) are deleted from a N-terminus and the disulfide bond formed by the cysteine residues is conserved and the peptide of (g) has the adrenomedullin activity.

3. The compound according to claim 1, wherein the polyethylene glycol group has an average molecular weight of from 10,000 to 40,000.

4. The compound according to claim 1, wherein n is 1 and the divalent linking group is a substituted or unsubstituted divalent aliphatic hydrocarbon group, a substituted or unsubstituted divalent cycloaliphatic group, or a substituted or unsubstituted divalent aromatic group.

5. The compound according to claim 1, wherein n is 1 and the divalent linking group is a substituted divalent aliphatic hydrocarbon group.

6. The compound according to claim 1, wherein n is 1 and the divalent linking group is a substituted or unsubstituted $C_1$-$C_{10}$ alkylene group, a substituted or unsubstituted $C_2$-$C_{10}$ alkenylene group, or a substituted or unsubstituted $C_2$-$C_{10}$ alkynylene group.

7. The compound according to claim 1, wherein n is 1 and the divalent linking group is a substituted $C_1$-$C_{10}$ alkylene group.

8. The compound according to claim 2, wherein said B is the peptide of (a).

9. The compound according to claim 1, wherein said B is the peptide of (i).

10. The compound according to claim 9, wherein n is 1.

11. The compound according to claim 10, wherein the divalent linking group is a substituted or unsubstituted divalent aliphatic hydrocarbon group, a substituted or unsubstituted divalent cycloaliphatic group, or a substituted or unsubstituted divalent aromatic group.

12. The compound according to claim 11, wherein the divalent linking group is a substituted divalent aliphatic hydrocarbon group.

13. The compound according to claim 10, wherein the divalent linking group is a substituted or unsubstituted $C_1$-$C_{10}$ alkylene group, a substituted or unsubstituted $C_2$-$C_{10}$ alkenylene group, or a substituted or unsubstituted $C_2$-$C_{10}$ alkynylene group.

14. The compound according to claim 13, wherein the divalent linking group is a substituted $C_1$-$C_{10}$ alkylene group.

15. The compound according to claim 8, wherein n is 1.

16. The compound according to claim 15, wherein the divalent linking group is a substituted or unsubstituted divalent aliphatic hydrocarbon group, a substituted or unsubstituted divalent cycloaliphatic group, or a substituted or unsubstituted divalent aromatic group.

17. A method for producing the compound according to claim 1, comprising linking a precursor of said B, a precursor of the polyethylene glycol group A, and a precursor of the divalent group $1_-$, to form the compound represented by formula (I).

18. A method for producing the compound according to claim 2, comprising linking a precursor of said B, a precursor of the polyethylene glycol group A, and a precursor of the divalent group $L_n$ to form the compound represented by formula (I).

19. A method for treating hypertension or inflammatory bowel disease, comprising administering to a subject in need thereof an effective amount of the compound according to claim 1 or a pharmaceutically acceptable salt thereof, or a pharmaceutically acceptable hydrate thereof.

20. A method for treating hypertension or inflammatory bowel disease, comprising administering to a subject in need thereof an effective amount of the compound according to claim 2 or a pharmaceutically acceptable salt thereof, or a pharmaceutically acceptable hydrate thereof.

\* \* \* \* \*

UNITED STATES PATENT AND TRADEMARK OFFICE
CERTIFICATE OF CORRECTION

PATENT NO. : 11,414,474 B2
APPLICATION NO. : 15/127202
DATED : August 16, 2022
INVENTOR(S) : Kazuo Kitamura et al.

It is certified that error appears in the above-identified patent and that said Letters Patent is hereby corrected as shown below:

In the Claims

Column 76, Line 25, the portion of Claim 17 reading "divalent group 1_" should read --divalent group Ln--.

Signed and Sealed this
Twenty-seventh Day of December, 2022

Katherine Kelly Vidal
*Director of the United States Patent and Trademark Office*